US012723967B2

(12) United States Patent
van Zee et al.

(10) Patent No.: US 12,723,967 B2
(45) Date of Patent: Sep. 1, 2026

(54) DEGRADABLE HOLLOW SHELL PARTICLES FOR HIGH-THROUGHPUT SCREENING AND SORTING OF CELLS

(71) Applicant: THE REGENTS OF THE UNIVERSITY OF CALIFORNIA, Oakland, CA (US)

(72) Inventors: Mark van Zee, Los Angeles, CA (US); Dino Di Carlo, Los Angeles, CA (US); Joseph de Rutte, Los Angeles, CA (US); Sohyung Lee, Pasadena, CA (US); Robert Damoiseaux, Los Angeles, CA (US); Cayden Williamson, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 742 days.

(21) Appl. No.: 18/006,382

(22) PCT Filed: Aug. 4, 2021

(86) PCT No.: PCT/US2021/044557
§ 371 (c)(1),
(2) Date: Jan. 20, 2023

(87) PCT Pub. No.: WO2022/031857
PCT Pub. Date: Feb. 10, 2022

(65) Prior Publication Data

US 2023/0257732 A1 Aug. 17, 2023

Related U.S. Application Data

(60) Provisional application No. 63/061,416, filed on Aug. 5, 2020.

(51) Int. Cl.

| | |
|---|---|
| ***G01N 15/10*** | (2024.01) |
| ***C12N 5/00*** | (2006.01) |
| ***C12N 11/04*** | (2006.01) |
| ***G01N 15/14*** | (2024.01) |
| ***G01N 21/64*** | (2006.01) |
| ***G01N 33/48*** | (2006.01) |

(52) U.S. Cl.
CPC .............. *G01N 15/10* (2013.01); *C12N 5/00* (2013.01); *C12N 5/0012* (2013.01); *C12N 11/04* (2013.01); *G01N 15/14* (2013.01); *G01N 21/6486* (2013.01); *G01N 33/48* (2013.01); *C12N 2509/00* (2013.01); *C12N 2537/10* (2013.01)

(58) Field of Classification Search
None
See application file for complete search history.

(56) References Cited

U.S. PATENT DOCUMENTS

| | | | |
|---|---|---|---|
| 8,361,415 B2 | 1/2013 | Di Carlo et al. | |
| 8,693,762 B2 | 4/2014 | Di Carlo et al. | |
| 10,144,911 B2 | 12/2018 | Di Carlo et al. | |
| 10,690,290 B2 | 6/2020 | Di Carlo et al. | |
| 10,912,860 B2 | 2/2021 | Griffin et al. | |
| 10,967,296 B2 | 4/2021 | Di Carlo et al. | |
| 2005/0153306 A1 | 7/2005 | Harris et al. | |
| 2009/0232901 A1 | 9/2009 | Walt et al. | |
| 2010/0003666 A1 | 1/2010 | Lee et al. | |
| 2014/0127290 A1* | 5/2014 | He | A61K 9/5089 435/178 |
| 2016/0257990 A1 | 9/2016 | Di Carlo et al. | |
| 2018/0036732 A1 | 2/2018 | Di Carlo et al. | |
| 2018/0056294 A1 | 3/2018 | Di Carlo et al. | |
| 2018/0161774 A1 | 6/2018 | Di Carlo et al. | |
| 2018/0258403 A1 | 9/2018 | Lutolf et al. | |
| 2019/0352591 A1* | 11/2019 | Steemers | A61K 47/58 |
| 2020/0305773 A1 | 10/2020 | Di Carlo et al. | |

(Continued)

FOREIGN PATENT DOCUMENTS

| | | | |
|---|---|---|---|
| WO | WO 2005/007678 A2 | 1/2005 | |
| WO | WO-2009003492 A1 * | 1/2009 | A61P 31/00 |

(Continued)

OTHER PUBLICATIONS

Zhao et al., "Hydrogel Encapsulation Facilitates Rapid-Cooling Cryopreservation of Stem Cell-Laden Core-Shell Microcapsules as Cell-Biomaterial Constructs", Advanced Healthcare Materials, vol. 6, 1700988, pp. 1-13 (Year: 2017).*
PCT International Preliminary Report on Patentability (Chapter I of the Patent Cooperation Treaty) for PCT/US2021/044557, Applicant: The Regents of the University of California, Form PCT/IB/326 and 373, dated Feb. 16, 2023 (14 pages).

(Continued)

*Primary Examiner* — Michelle F. Paguio Frising
(74) *Attorney, Agent, or Firm* — VISTA IP LAW GROUP LLP

(57) ABSTRACT

Degradable hollow shell particles are disclosed that can encapsulate cells within the hollow inner cavity that allows for the high-throughput screening and sorting of the encapsulated cells based on their phenotypic properties. The solid-phase of the particle is porous such that solution exchange can occur between the external environment and the interior cavity. Further, the solid-phase contains degradable crosslinkers and can be degraded to release enclosed biological entities. An example embodiment consists of encapsulating a cell within the hollow shell particle, allowing the cell to accumulate biomass, selecting hollow shell particles based on accumulated biomass, and degrading the hollow shell particles to release the cells and develop hyper-producing cell lines. Exemplary cell types include microalgae, mammalian cells, bacteria, yeast, and fungi.

14 Claims, 30 Drawing Sheets

Specification includes a Sequence Listing.

(56) References Cited

U.S. PATENT DOCUMENTS

| | | | |
|---|---|---|---|
| 2021/0268465 | A1 | 9/2021 | Di Carlo et al. |
| 2021/0403649 | A1 | 12/2021 | Sheikhi et al. |
| 2022/0233413 | A1 | 7/2022 | Di Carlo et al. |
| 2022/0370686 | A1 | 11/2022 | Di Carlo et al. |

FOREIGN PATENT DOCUMENTS

| | | | |
|---|---|---|---|
| WO | WO 2015/058103 | A1 | 4/2015 |
| WO | WO 2018/156935 | A1 | 8/2018 |
| WO | WO 2020/037214 | A1 | 2/2020 |
| WO | WO 2021/262312 | A2 | 12/2021 |
| WO | WO 2022/016013 | A1 | 1/2022 |
| WO | WO 2022/056020 | A1 | 3/2022 |
| WO | WO 2022/240655 | A1 | 11/2022 |
| WO | WO 2022/240656 | A1 | 11/2022 |

OTHER PUBLICATIONS

PCT International Search Report for PCT/US2021/044557, Applicant: The Regents of the University of California, Form PCT/ISA/210 and 220, dated Feb. 25, 2022 (7 pages).

PCT Written Opinion of the International Search Authority for PCT/US2021/044557, Applicant: The Regents of the University of California, Form PCT/ISA/237, dated Feb. 25, 2022 (12 pages).

Mi-Sung Yim et al., A novel selective growth medium-PCR assay to isolate and detect Sphingomonas in environmental samples, J. Microbiol Methods, Jul. 2010; 82(1):19-27.

Robert Visse et al., Matrix Metalloproteinases and Tissue Inhibitors of Metalloproteinases, Structure, Function, and Biochemistry, Circ Res. 2003; 92:827-839.

Ye-Jin Eun et al., Encapsulating bacteria in agarose microparticles using microfluidics for high-throughput cell analysis and isolation, ACS Checm Biol. Mar. 18, 2011; 6(3):260-266.

Joseph Michael de Rutte et al., Scalable High-Throughput Production of Modular Microgels for In Situ Assembly of Microporous Tissue Scaffolds, Adv. Funct. Mater. 2019, 29, 1900071 (10 pages).

Joseph de Rutte et al., Massively parallel encapsulation of single cells with structured microparticles and secretion-based flow sorting, (Mar. 2020) DOI:10.1101/2020.03.09.984245; https://www.researchgate.net/publication/339852221.

Toru Hoshi et al., Encapsulation of Micro- and Milli-Sized Particles with a Hollow-Type Spherical Bacterial Cellulose Gel via Particle-Preloaded Droplet Cultivation, Int. J. Mol. Sci. (2019) 20, 4919; doi:10.3390/ijms20194919.

P. Hyka et al., Flow cytometry for the development of biotechnological processes with microalgae, Biotechnology Advances 31 (2013) 2-16.

Ming Li et al., A Gelatin Microdroplet Platform for High-Throughput Sorting of Hyperproducing Single-Cell-Derived Microalgal Clones, Small 2018, 14, 1803315 (9 pages).

Annamaria Mocciaro et al., Light-activated cell identification and sorting (LACIS) for selection of edited clones on a nanofluidic device, Communications Biology (2018) 1:41; DOI:10.1038/s42003-018-0034-6; www.nature.com/commsbio.

Cristina Parola et al., Antibody discovery and engineering by enhanced CRISPR-Cas9 integration of variable gene cassette libraries in mammalian cells, MABS, 2019, vol. 11, No. 8, 1367-1380.

Takaichi Watanabe et al., Microfluidic Formation of Hydrogel Microcapsules Microcapsuleswith a Single Aqueous Core by Spontaneous Cross-Linking in Aqueous Two-Phase System Droplets, Langmuir, Feb. 12, 2019;35(6):2358-2367. doi: 10.1021/acs.langmuir.8b04169. Epub Jan. 22, 2019.

Koji Yamada et al., Efficient selective breeding of live oil-rich Euglena gracilis with fluorescence-activated cell sorting, Scientific Reports, 6:26327; DOI:10.1038/srep26327 (2016).

* cited by examiner

3D Structure

10

Cross section plane

FIG. 1A

Cross Section

Actual Image

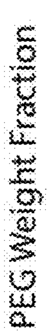
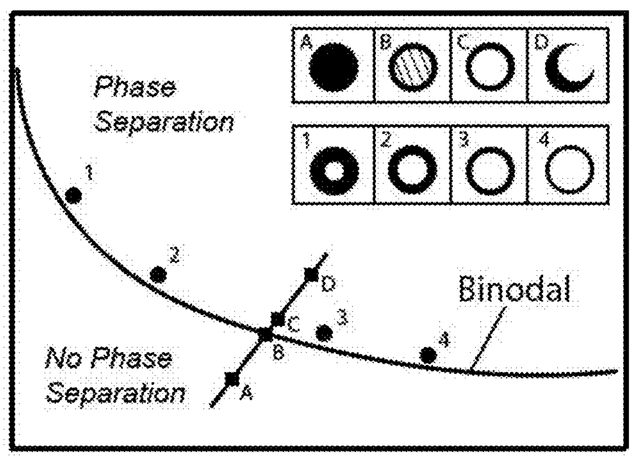
FIG. 3
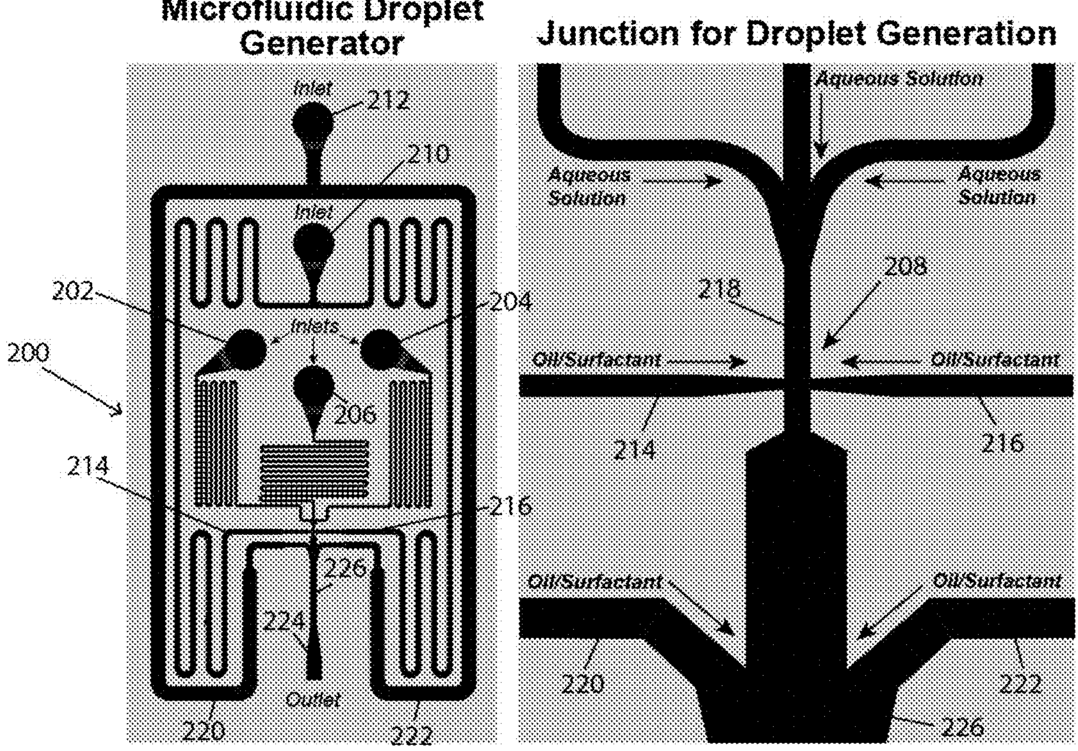
FIG. 4A FIG. 4B

6% PEG, 2.5% DEX 6.5% PEG, 2.5% DEX

7% PEG, 2.5% DEX

100 μm

No Phase Separation

Binodal

Turbidity

Phase Separation

Interface

General pH-Based Gelling and Breakdown Mechanisms

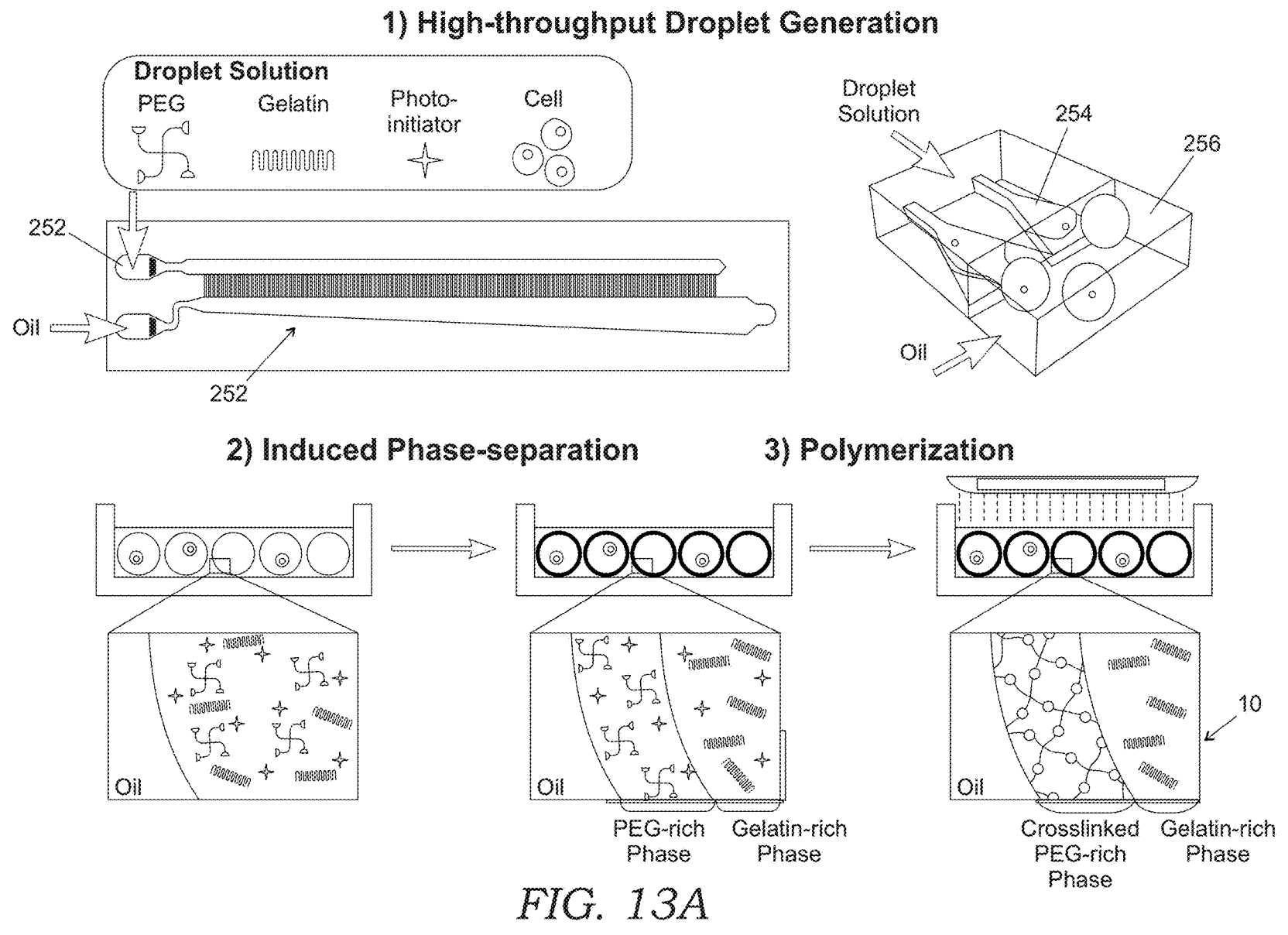

1) High-throughput Droplet Generation

Droplet Solution
PEG
Gelatin
Photo-initiator
Cell 252
252
Oil

Droplet Solution
Oil
254
256

2) Induced Phase-separation

Oil
Oil
PEG-rich Phase
Gelatin-rich Phase

3) Polymerization

10
Oil
Crosslinked PEG-rich Phase
Gelatin-rich Phase

FIG. 13A

Water-in-oil Emulsion

Holow Shell Particle

Channel Height

Crosslink and Wash

Enclosed Cavities

Exposed Cavities

DEGRADABLE HOLLOW SHELL PARTICLES FOR HIGH-THROUGHPUT SCREENING AND SORTING OF CELLS

RELATED APPLICATION

This Application is a U.S. National Stage filing under 35 U.S.C. § 371 of International Application No. PCT/US2021/044557, filed on Aug. 4, 2021, which claims priority to U.S. Provisional Patent Application No. 63/061,416 filed on Aug. 5, 2020, which are hereby incorporated by reference. Priority is claimed pursuant to 35 U.S.C. §§ 119, 371 and any other applicable statute.

STATEMENT REGARDING FEDERALLY SPONSORED RESEARCH AND DEVELOPMENT

This invention was made with government support under N00014-16-1-2997, awarded by the U.S. Navy, Office of Naval Research. The government has certain rights in the invention.

TECHNICAL FIELD

The technical field generally relates to degradable particle-based systems for encapsulating living cells. More specifically, the technical field relates to systems and methods for the encapsulation of cells within a degradable particle containing a hollow inner cavity.

BACKGROUND

With the heightened interest in cell-derived bioproducts (recombinant therapeutic proteins, antibody therapies, high-energy lipids) and cell-therapies (e.g., Chimeric antigen receptor T (CAR T) cell and stem cell therapies), the characterization of selection of desired cells based on their particular phenotypic properties has become increasingly important. For example, Chinese hamster ovary (CHO) cells accumulating a desired recombinant therapeutic protein needs to be separated from non-producers in order to maximize production yields. In another example, the receptor and secretion profile of stem cells need to be fully characterized and understood before injecting them into patients for therapeutic purposes.

Unfortunately, current macroscale techniques to select out desired cells or to enrich populations are severely limited. For example, secretions from or biomass accumulation properties of cells have traditionally been characterized using well-plate ELISA and imaging techniques that have very low throughputs (<10,000 cells/screen), requires a lot of labor or costly automated equipment, can take several weeks to months to perform, and are limited in the number cell features that can be characterized. These limitations are largely a result of the large microliter range volumes that are required to perform such assays. In order to obtain a detectable signal for secretion or biomass assays, a large amount of secretions and/or number of cells need to be present in the wells. If a researcher wants to start with a single cell per well, it will take several weeks to months to obtain a detectable signal. In order to reduce the amount of time required to perform a full screen a researcher must start with many cells in each well, making it extremely challenging to select out rare cells that exhibit phenotypic properties of interest or characterize the individual strategies to elicit a desired trait. Turbidostats and other bioreactors can also be used to enrich populations based on cell properties (particularly growth rate). However, enrichment using these tools can take several months to perform and tend to have selection pressures that result in the development of undesired properties (e.g., cell clumping, algae with large photosynthetic antennae, etc.).

To enhance throughput, engineers and researchers have developed high-throughput cytometry systems that can screen and select cells with desired phenotypic properties. Very popular tools that researchers use are flow cytometers that use fluorescence-based readouts to characterize and sort cells of interest. Fluorescent labels that target particular regions of cells can be added to cell populations and the quantity of such labels on each individual cell can be quantified using flow cytometers at throughputs up to 70,000 cells/s. Cells can be sorted based on the binary presence or quantity of such fluorescent labels. Magnetic activated cell sorting (MACS) has enhanced the throughput to ~10 million cells per second. However, systems cannot easily quantify the amount of labels present and are unable to distinguish between labels with different targets (e.g., not able to multiplex). Mass cytometry has enabled researchers to characterize cells based on 60+ different quantifiable parameters at throughputs up to 2000 cells/s, significantly improving the multiplexing capabilities that are possible with such flow systems. Image cytometry has enabled researchers to characterize the spatial location of elements on and within cells at throughputs of ~5000 cells/s. Unfortunately, an important and critical limitation of all of these high-throughput cytometry systems is that they are only capable of characterizing and selecting based on surface biomarkers and internal cellular components. They cannot characterize very relevant phenotypic properties such as secretion rate, affinity/specificity of secretions, and growth rate or growth of colonies.

Microscale methods such as microwell, microcapillary, droplet, and gel microdrop technologies are capable of compartmentalizing single cells into nanoliter-sized compartments, allowing cells to grow and/or accumulate secretions inside such compartments over a desired period of time and researchers to select clones based on these properties. Due to the significantly small volume sizes of the compartments, it only takes a few hours to obtain a detectable signal from secretions from a single cell or a few days to characterize the growth of a single clonal colony. These approaches generally also have automated high-throughput screening mechanisms that make it possible to screen at throughputs of ~100°-5000 cells/s. These microscale technologies have also enabled certain multiplexing capabilities not possible with previously described methods (e.g., growth and secretion rate, secretion of multiple proteins, presence of a specific biomarker and particular secretion).

While these technologies are widely used as a means to select cells based on desired phenotypic properties, droplet technologies often do not allow for solution exchange, creating potential issues for long term studies. For example, the small volume of a droplet (typically less than 1 nL) can lead to rapid nutrient depletion and accumulation of cytotoxic substances that may affect cell behavior during long term culture. Additionally, cellular respiration and release of acidic materials from mammalian cells result in the lowering of pH in the surrounding solution. This will likely create non-ideal conditions for characterizing particular phenotypic properties such as biomass accumulation and may affect protein-protein interactions important for secretion assays. Lastly, cell behavior is oftentimes dependent on its interactions with other cell's secretions (e.g., growth factors, paracrine factors, quorum sensing factors). Such interactions are limited to cells within the encapsulated water-in-oil emulsions given the lack of transport out of droplets. Therefore, screening and selection with these microscale technologies are limited in the ability to investigate cell-cell communication while being able to sort out one cell population independent of the communicating cell population. While it is technically possible to change/alter media with these microscale technologies, it will require the de-compartmentalization and re-compartmentalization of cells, a process that is difficult and is likely to have negative consequences on the desired assay. Nanopen technology (e.g., from Berkeley Lights, Inc.) does feature nanoliter-sized compartments that can have continuous solution exchange and have their solution replaced without dislodging cells; however, it requires light-based manipulation to isolate desired cell/colonies that has a limited throughput of ~30,000 cells/screen.

SUMMARY

In one embodiment, to mitigate the issues resulting from the lack of solution exchange present in droplet technologies, a platform involving 'hollow shell' particles are provided that are capable of compartmentalizing cells inside the hollow void or compartment of the particle. The hollow shells are made from a hydrogel (such as polyethylene glycol (PEG)) that is resistant to external mechanical pressures, creating a stable environment for encapsulated cells and their potential growth. The hydrogel-based shell is also selectively porous, allowing for solution exchange between the interior environment and the external environment and transport of molecular species below a molecular weight cut-off. These hollow shell particles can be easily transferred from one solution to another and allow for biological materials or reagents (e.g., proteins, dyes, etc.) to enter and exit the interior compartment. The hollow shell particles are also sized and manufactured from non-adhesive materials that are compatible with traditional flow cytometers or fluorescence activated cell sorters (FACS) for analysis and sorting. Typical sizes for hollow shell particles are between 5-500 micrometers in outer diameter. The hydrogel material is also optionally crosslinked with a degradable crosslinker (peptide sequences, di-sulfide linkages, etc.) that can be degraded via added biocompatible degradation reagents (enzymes, reducing agents, DTT, TCEP, etc.). Another degradation reagent includes sodium periodate ($NaIO_4$) which can degrade some hollow shell particles 10 (e.g., PEG-MAL/DTT) due to presence of a diol in DTT. Unfortunately, $NaIO_4$ can be toxic and likely kills or has large negative impacts on many cell types. The particular crosslinker and degradation reagent should be selected on the particular cell that is encapsulated. The hydrogel material may also optionally be degraded via physical methods that do not significantly affect the viability of cells. In particular, the hollow shell particles can be opened by directly applying a shearing force that degrades the hollow shell particles and allows for cells to be released. Cells may also grow past the carrying capacity of the inner cavity, causing the outer shell to stretch to the point of rupture. Therefore, the hollow shell particles can be broken down following analysis, screening, or selection to release interior components, such as cells, for further studies or re-growth.

While other 'hollow-shell' or 'core-shell' particles at a similar scale have been demonstrated, the particles and methods are not biocompatible and therefore would not maintain cell viability or may have undesired effects on cell phenotype during a potential cell-encapsulation step. For example, a previous method to form such particle shapes rely on atom transfer radical polymerization (ATRP) for the solidification of the outer shell. This is well suited for drug delivery applications; however, such a solidification mechanism is genotoxic to cells that a user may try to encapsulate into the particles. By using chemistries and methods that are biocompatible, hollow shell particles can be used for cell assay applications. In particular, the hollow shell particle systems disclosed herein are designed for high-throughput cell screening and selection based on cell function or growth or genotypic or phenotypic properties.

The mechanism to form hollow shell particles using a similar method has also been shown. However, such fabricated particles have not been involved in any applications or use cases for high-throughput screening nor have been used for the encapsulation of cells. For example, high-throughput analysis and screening using flow cytometers and FACS systems. Additionally, previous methods and systems do not describe a biocompatible mechanism to release the cells from the particles following an assay or sorting process. Breakdown of the previous particles requires extreme physical or chemical methods that are likely to damage any cells that were enclosed within the particles. The system disclosed herein is preferably used for the sorting of desired cell lines that can afterwards be re-cultured or further processed. Therefore, an important feature of the system is that the particles can be physically or chemically broken down in a biocompatible way such that selected/screened cells can remain undamaged and viable after release.

In one exemplary embodiment, living cells (e.g., microalgae, mammalian cells, bacteria, yeast, fungi) are incorporated into the inner cavity of the hollow shell particles during manufacture and placed into the cell's native media. Cells are allowed to exhibit one or more phenotypic properties (e.g., biomass accumulation, growth, cell division, secretion, adherence, biomolecule accumulation) over a period of time ranging from several minutes to several months. In several embodiments, cells (generally suspension cells such as microalgae, lymphocytes) remain suspended within the inner cavity and have little to no interaction with the solid phase of the particle shell. In another embodiment, the solid phase of the particle contains cell-binding agents (peptide sequences, proteins, nucleic acids, charged substances, antibodies) to which cells can attach (generally adherent cell types such as adherent CHO cells, stem cells). In yet another embodiment, biomolecules released from the enclosed cells (via secretion, lysis, pores) are retained within the particle via size exclusion (desired biomolecules are larger than the pore size of the matrix), via binding to capture agents within the solid phase of the particle (proteins, peptide sequences, nucleic acids), or via binding to capture agents that are co-suspended within the inner cavity (functionalized objects, cells, other multivalent affinity agents). Assays can also involve any combination of the previous embodiments. Following an incubation time, cells or released biomolecules within the particle may be labeled via detectable biomarkers (e.g., fluorescent biomolecules or stains, magnetic biomolecules or stains, metal-labeled entities) that can enter the inner cavity of the particle from the environment external to the solid phase of the particle. Cells within the inner cavity may also be lysed via lytic agents (enzymes, detergents) that can enter from the external environment through the solid phase.

Cell- or cell genome-containing particles can then be screened, sorted, or selected using high-throughput screening or sorting tools (e.g., flow cytometry, image cytometry, microscopy, magnetic devices, mass cytometry) based on the presence of the previously added detectable biomarkers or recognizable properties of the cells or released biomolecules (autofluorescence intensity, spatial location of biomolecules within a particle, spatial location of cell(s) interior components, scatter signal). Viable cells or cell colonies can then be released from the particle via the addition of agents (proteins, enzymes, chemicals, light) that can cleave components of the particle's solid phase (peptide sequences, di-sulfide bridges, synthetic linkers) or addition of physical stress/mechanical force to disrupt the particle.

Hollow shell particles are uniquely designed to both compartmentalize cells and allow for solution exchange between the interior compartment within the shell and the external environment. Droplet-based technologies are a common method to compartmentalize cells; however, the compartments are enclosed within an external oil layer such that only some types of small molecules can diffuse between the compartment and the external environment (gases, water). Larger biomolecules cannot be released from the interior compartment nor can large biomolecules enter from the external environment without destabilizing the droplet. As such, cells can metabolically consume important materials in the encapsulated solution (sugars, metals, amino acids, proteins, etc.) that are important for the cells proper functioning and survival. In addition, cytotoxic agents (e.g., lactic acid, etc.) normally released by cells can accumulate within the compartment, affecting their function and viability during longer incubation times. Also, cells generally lower the pH of their external solution over time due to metabolic activity and release of carbon dioxide, potentially causing other issues for longer term studies. Phenotypic properties of cells are often affected by cell density because of the release of biomolecules (growth factors, quorum sensing molecules, etc.) by surrounding cells. When droplets are used to encapsulate single cells, there is no interchange of these factors between cells and so the cells may exhibit different phenotypic properties when compartmentalized within droplets then if they were present in a more commercially relevant condition (e.g., bulk culture).

The lack of solution exchange with droplet technologies also presents limitations on the potential assays that can be performed. For example, assays requiring that cells be resuspended in different types of media intermittently throughout the incubation time, or be exposed to a bulk culture of similar or different cells, cannot be done without having the cells be released from droplets and re-encapsulated. Additionally, droplets generally cannot be stored in environments that normally require physical stimuli (e.g., flask on a shaker) because such physical stress is likely to destabilize the droplet. Also, lack of cell-cell communication in droplet-based assays makes it difficult to perform assays where desired cells are compartmentalized and yet interact with factors released by other external cell types (e.g., a B-cell compartmentalized in a particle within a solution that contains T-cells, NK cells, conditioned media, etc.). Such solution exchange can be performed when cells are compartmentalized via other microfluidic technologies (optofluidic platforms, microwell technologies, microcapillaries); however, these technologies can have low throughput or risk compartmentalized components being displaced during a solution exchange process.

In one embodiment, a particle system for containing live cells therein is disclosed and includes a plurality of hollow shell particles formed from a biocompatible and a chemically or physically degradable crosslinked hydrogel, each hollow shell particle having a void or cavity formed therein and surrounded by a shell of crosslinked hydrogel with one or more live cells contained in the void or cavity.

In another embodiment, a method of using the particle system includes subjecting the plurality of hollow shell particles to screening and/or sorting by one of: flow cytometry, fluorescence-activated cell sorter (FACS), image activated cell sorting (IACS), microscopy, mass spectrometry, filtering, or a magnetic sorter device.

In another embodiment, a method of using the particle system includes incubating the plurality of hollow shell particles to grow the one or more cells contained therein. In some embodiments, the plurality of hollow shell particles are then chemically or physically degraded or otherwise opened to release their contents. This may include opening only those desired hollow shell particles that have been subject to screening and/or sorting.

In one embodiment, another method of using a particle system includes providing plurality of hollow shell particles formed from a biocompatible and chemically or physically degradable crosslinked hydrogel, each hollow shell particle having a void or cavity formed therein and surrounded by a shell of crosslinked hydrogel and having a single cell contained in the void or cavity of at least some of the plurality of particles. The plurality of hollow shell particles are incubated in a growth media for a time period to obtain multicellular colonies contained in the void or cavity of at least some of the plurality of hollow shell particles. The cells and/or the hollow shell particle are optionally labelled with a fluorescent label or fluorogenic substrate. The plurality of hollow shell particles are then passed through a fluorescence activated cell sorter and sorting hollow shell particles containing multicellular colonies based on a fluorescence and/or scatter signal of each hollow shell particle.

In another embodiment, a method of forming biocompatible and degradable hollow shell particles loaded with one or more cells includes the operations of: providing a microfluidic device having first, second, and third inlet channels that converge into a droplet generation region that is intersected by a pair of pinch channels, the droplet generation region further coupled to an outlet channel; flowing polyethylene glycol (PEG) in the first inlet channel; flowing dextran in the second inlet channel; flowing a crosslinker in the third inlet channel; and flowing an oil phase in the pair of pinch channels; wherein cells are co-flowed in one of the first, second, and third inlet channels and wherein droplets form in the droplet generation region and continue into the outlet channel and the droplets undergo phase separation and crosslinking to form hollow shell particles containing one or more cells therein. In another embodiment, only two inlet channels are used with the crosslinker and dextran are combined the flow of one of the inlet channels.

BRIEF DESCRIPTION OF THE DRAWINGS

FIGS. 1A-1C illustrates the general shape of hollow shell particles. Hollow shell particles are formed from a solid polymer matrix which has an outer shell and hollow inner cavity which does not contain a solid polymer matrix. FIG. 1A illustrates the three-dimensional structure and a cross-sectional plane taken along a diameter. FIG. 1B illustrates a cross-sectional view taken along the plane of FIG. 1A. FIG. 1C illustrates an actual microscopic image of a hollow shell particle. Scale bar=50 μm.

FIG. 3: Hollow shell particle morphologies can be fine-tuned by adjusting PEG and dextran in the droplets. At low concentrations, there is no phase separation between PEG and dextran, resulting in a solid particle without a shell. High concentrations of PEG and/or dextran results in full separation and the formation of Janus particles. Concentrations at the binodal results in a region where the phases slightly phase separate but there is still some PEG within the center of the droplet/particle. At slightly higher concentrations above the binodal, the two phases fully separate but the surface tensions between the phases are balanced out, resulting in dextran localizing in the center of the droplet and resulting in hollow shell particles. The cavity size and shell thickness can be adjusted by changing the ratio of dextran and PEG just above the binodal. A higher dextran to PEG ratio results in a larger cavity size and a lower ratio results in a smaller cavity size.

FIGS. 4A and 4B illustrate the design of microfluidic droplet generator device (FIG. 4A) and junction for droplet generation (FIG. 4B) for droplet-based collection of the binodal curve data and formation of hollow shell particles. The device consists of five (5) inlets, three (3) for aqueous solutions and two (2) for oil/surfactant mixtures. The oil/surfactant inlet furthest away (downstream) from the point of droplet generation can be optionally used to add additional oil/surfactant or adjust pH.

FIGS. 8A-8B show examples of two chemistries that can be used to gel and breakdown the hollow shell particles during cell encapsulation and release, respectively. The particles may be gelled with cystamine and multi-arm PEG maleimide at basic pHs and broken down with thiol-cleaving substances such as DTT and TCEP (FIG. 8A). Particles may be gelled with a peptide sequence that contains thiols (can be from cysteine) that allows it to crosslink multi-arm PEG maleimide at acidic pHs. These peptide sequences can comprise matrix metalloproteinase (MMP) degradable peptide sequences and be cleaved with the addition of MMPs. The peptide sequence can also be designed to allow cleavage by bio-orthogonal enzymatic reactions (e.g., TEV protease with sequence ENLYFQG [SEQ ID NO: 10] or ENLYFQS) [SEQ ID NO:11]) (FIG. 8B).

FIG. 12A *Chlorella* growth after incubation with 20 kDa dextran for 2 h showing no difference from control media. FIG. 12B *Chlorella* growth after incubation with 20 kDa 4-arm PEG-maleimide, 20 kDa 4-arm PEG-vinyl sulfone, or 20 kDa 4-arm PEG-orthopyridyl disulfide for 10 min. FIG. 12C *Chlorella* growth after incubation with cystamine, peptide, or DTT. FIG. 12D *Chlorella* growth after incubation with 20% or 100% (v/v) perfluoro-octanol for a 10 min period.

FIG. 13A schematically illustrates overview of high-throughput production of hollow shell particles. 1) Monodisperse droplets are generated with high-efficiency using a parallelized step-emulsification device. 2) Phase-separation of the droplets are induced by a number of methods, including: changing temperature, pH and chemical composition. 3) Following the phase separation of droplets, the droplets are exposed to a stimulus (e.g., pH, temperature) to cross-link phase separated droplets to form hollow shell particles.

FIG. 14A shows the binodal curves for solutions of gelatin and different molecular weight PEG. The binodal curves (lines) were estimated based on the experimental phase separation behavior of solutions for different concentrations of PEG and gelatin (points). FIG. 14B shows that when PEG and gelatin are mixed in aqueous solution, a solution with higher MW PEG have stronger tendencies to partition into two distinct phases, leading to phase-separation at lower concentration of PEG and gelatin. A droplet, whose chemical composition is denoted by ✹ in FIG. 14B, is homogeneous when the PEG MW is 700 Da. As the PEG component is partially crosslinked into a higher MW PEG (~1500 Da), the position of the droplet relative to the binodal curve switches from the below to the above. Therefore, the droplet is partitioned into two distinct phases where one phase is completely enclosed by another. FIG. 14C illustrates how multi-arm PEG with heterogeneous functional groups, which therefore require different crosslinking methods, can be used to increase the MW of PEG. For example, 4-arm PEG with a pH dependent VS group and three photocrosslinkable groups undergoes partial cross-linking upon increasing the pH of droplets as pH reactive VS groups form crosslinks each other. This results in an increase in MW of PEG and triggers the phase separation between PEG and gelatin component in the droplet.

allowed for more complete phase separation and formation of hollow shell particles (right) as observed.

Figure 16A:
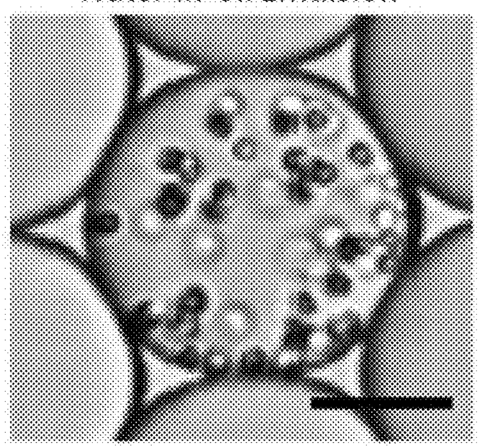
Figure 16B:
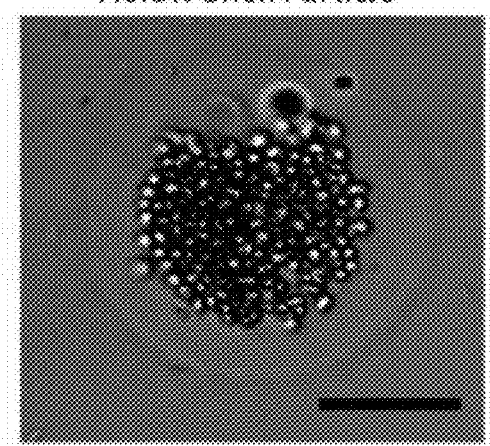

FIGS. 16A and 16B illustrates the effects of solution exchange on overall *Chlamydomonas* growth. FIG. 16A shows reduced growth in a water in oil emulsion compared to increased growth in a hollow shell particle in FIG. 16B. The particle's solid matrix is composed of 20 kDa 4-arm PEG-maleimide that is crosslinked with a di-cysteine peptide sequence containing an MMP degradable sequence synthesized at Genscript (Ac-GCRDGPQGIWGQDRCG-$NH_2$, [SEQ ID NO: 1]). The solution within the droplet (FIG. 16A) and surrounding/within the hollow shell particle (FIG. 16B) is Tris-acetate-phosphate (TAP) medium supplemented with Kropat's trace elements solution at a pH of 7. Both images were taken in similarly sized compartments after 72 h of growth. Provided images were taken at the point where the algae reached carrying capacity and are images of the most densely packed clonal colonies within each respective population. Scale bars=50 μm.

Figure 17:
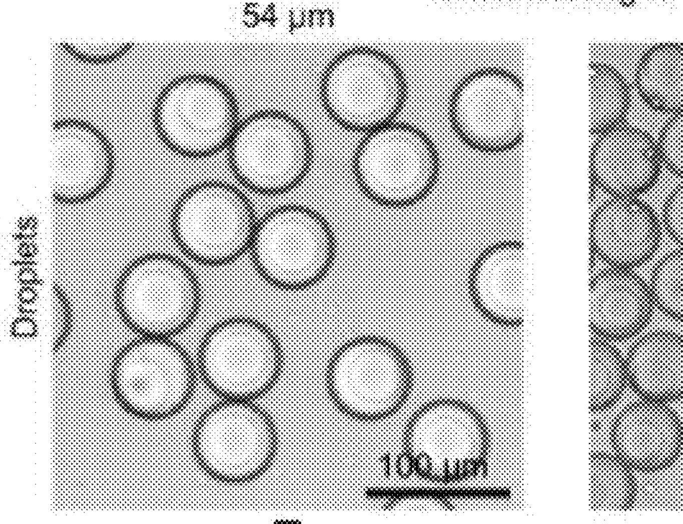
Figure 17:
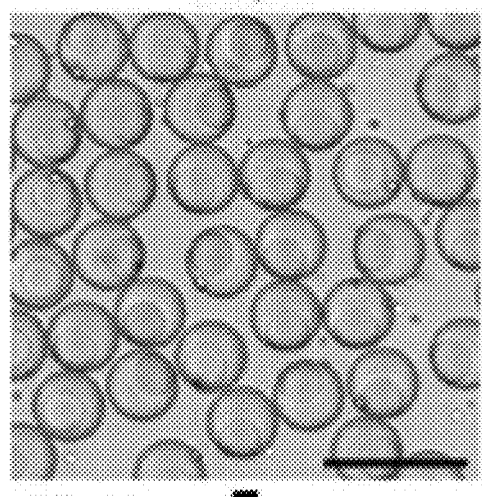
Figure 17:
Figure 17:
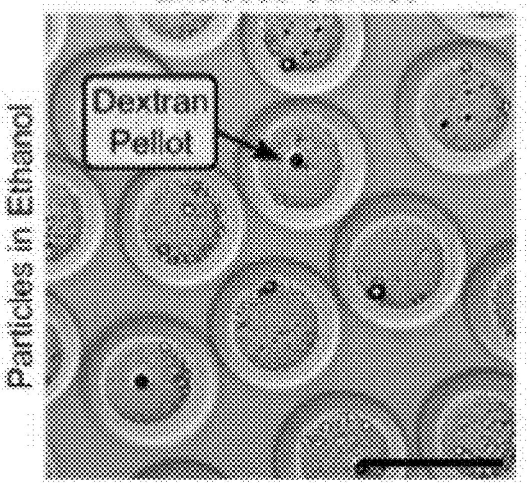
Figure 17:
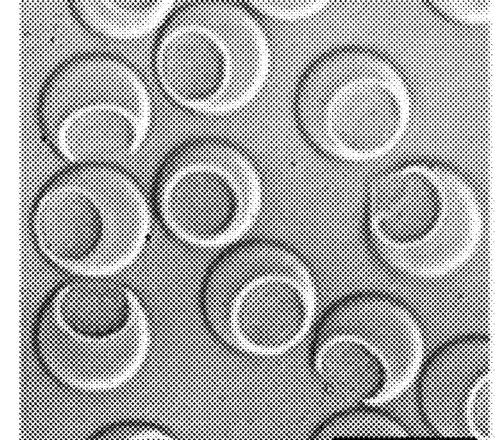

FIG. 17: Illustrates the effect of channel height on enclosed hollow shell particle fabrication. Depicted are 50-55 micron droplets composed of 13.15% w/w 4-arm PEG norbornene (10 ka) and 5% w/w 40 kDa Dextran confined in two separate microfluidic channels. In the device with channel height close to the droplet size (54 microns) it was noted that the dextran phase stayed centered in the droplet. In the device with a significantly larger channel, it was noted that the dextran phase localizes to the edge of the droplet. After crosslinking with UV light in the channels and washing, the particles extracted from the 54-micron channels had mostly fully enclosed cavities (as revealed by dextran pellets localized in the cores when suspended in ethanol). For the particles fabricated in the larger channel device, nearly all the particles had a cavity exposed to the outside of the particle.

Figures 18A, 18B:
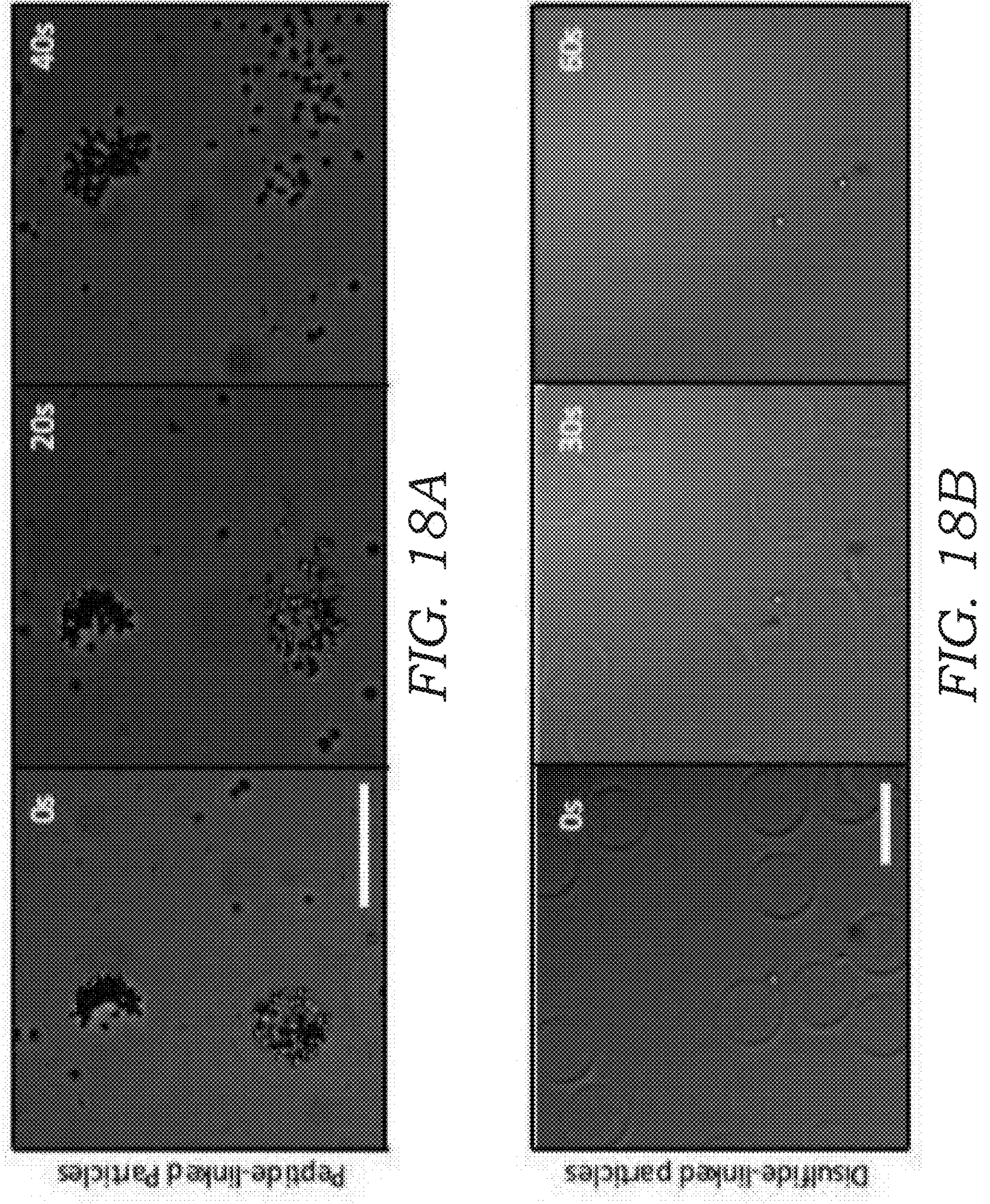

FIGS. 18A-18B are photographs showing the degradation of hollow shell particles. FIG. 18A shows images of the breakdown of hollow shell particles made of 20 kDa 4-arm PEG maleimide crosslinked with di-cysteine modified MMP-degradable peptide (Ac-GCRDGPQGIWGQDRCG-$NH_2$, [SEQ ID NO: 1]). Hollow shell particles contain *Chlamydomonas reinhardtii* that had been accumulating biomass within the hollow shell particles for 3 days. 0.05% (w/v) trypsin was added to the particles at 0 s to induce breakdown of hollow shell particles and release of enclosed algal cells. Hollow shell particles degrade after ~40 s. FIG. 18B shows the breakdown of di-sulfide crosslinked hollow shell particles. Hollow shell particles were made by crosslinking 20 kDa 4-arm PEG-orthopyridyl disulfide (OPSS) with dithiolthreitol (DTT). Crosslinking ratio of DTT to OPSS was 0.8. The hollow shell particles were broken down with the addition of 1 mM DTT. Particles fully degrade after ~60 s. Scale bar=100 μm.

Figure 19:
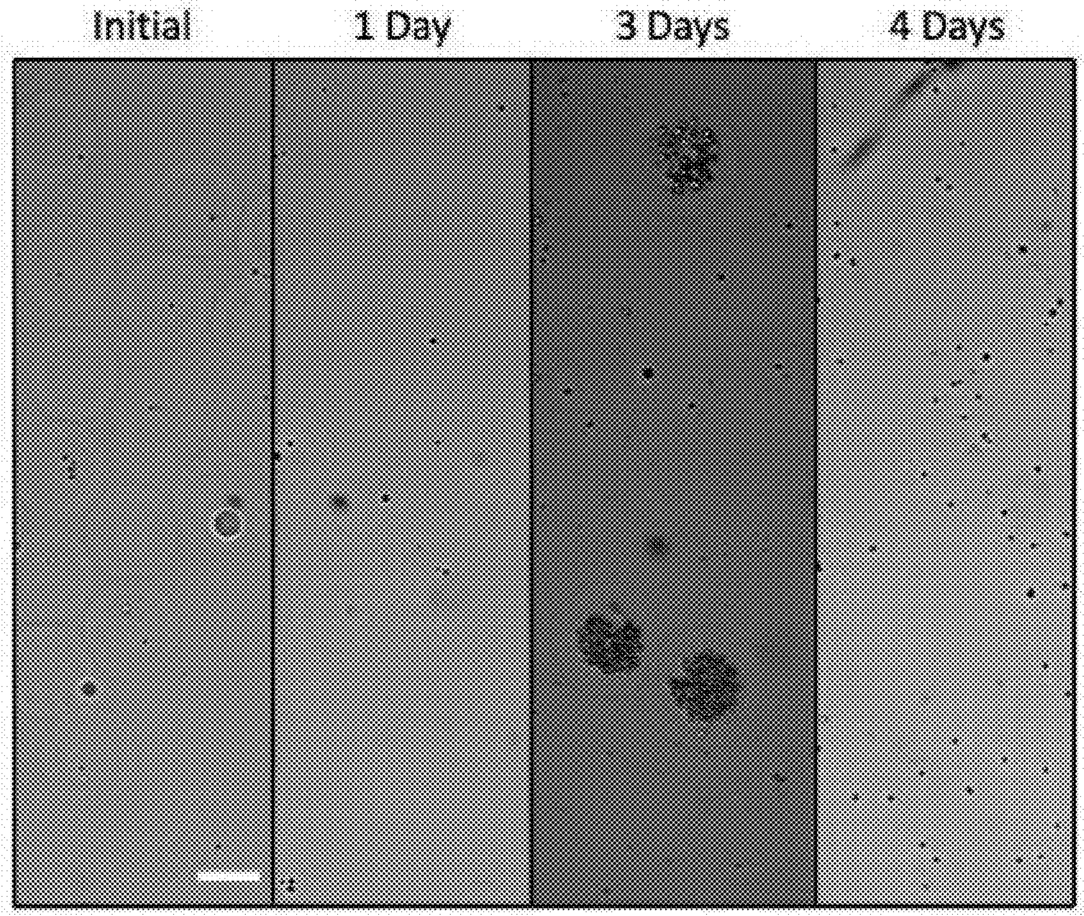

FIG. 19 illustrates algae self-degradation of MMP-degradable hollow shell particles. *Chlamydomonas reinhardtii* were encapsulated into hollow shell particles crosslinked with a di-cysteine modified matrix metalloproteinase (MMP) degradable peptide sequence (Ac-GCRDGPQGIWGQDRCG-$NH_2$, [SEQ ID NO: 1]). Algal cells were initially encapsulated at roughly one cell per particle and cell-containing particles were incubated in standard culture conditions for *Chlamydomonas* (TAP media, 25° C., 120 RPM, 2000 μmol $m^{-2}$ $s^{-1}$ light) to allow cells to accumulate biomass. After 4 days of incubation, algal cells were able to release themselves from the particles by fully degrading the solid matrix. This self-release may result from MMPs or other proteases that are naturally secreted from the algal cells that cleave the MMP-degradable peptide sequence. Scale bar=50 μm.

Figure 20A:
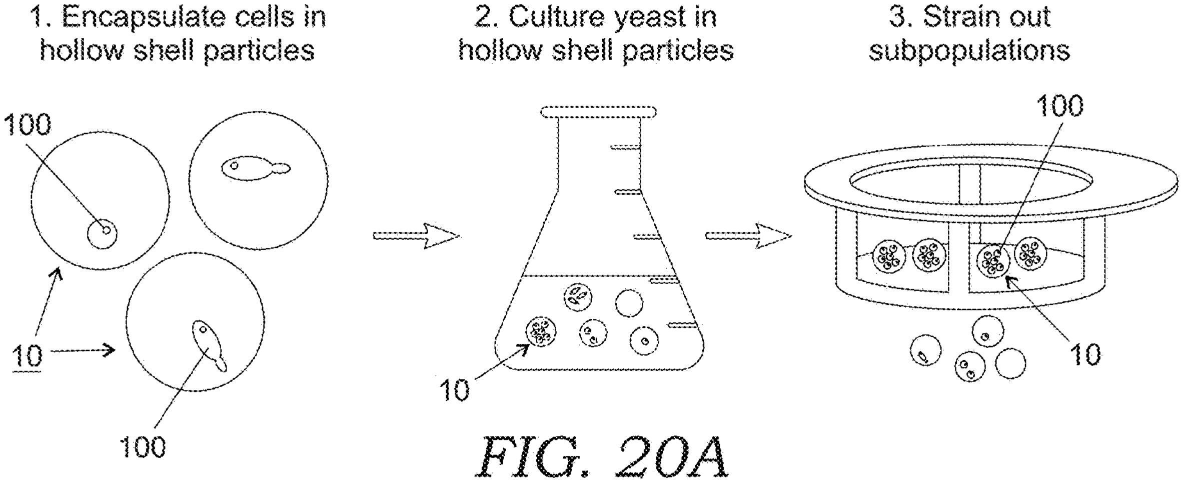
Figure 20B:
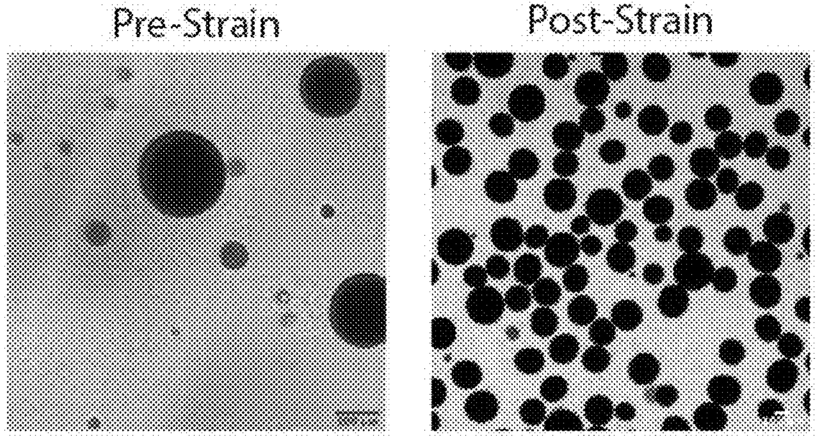

FIGS. 20A-20B: Illustrate using a cell strainer/filter device to isolate fast-growing yeast colonies. FIG. 20A is a schematic illustrating general hollow shell particle workflow using a 100 μm cell strainer to isolate high-growing mutants from an initial yeast population. *Saccharomyces cerevisiae* were encapsulated into hollow shell particles crosslinked with PEG-OPSS and DTT. Cells were initially encapsulated at a concentration such that 10% of hollow shell particles contained a single cell and cell-containing particles were incubated in standard culture conditions for *S. cerevisiae* for 24 hours. Hollow shell particles were then pipetted through a 100 μm cell strainer. The hollow shell particles that had expanded in size to a diameter greater than 100 μm in diameter due to yeast colony growth were captured and retained, while empty and partially-filled hollow shell particles passed through the strainer. FIG. 20B shows representative pre- and post-strain images illustrating the enrichment of fast-growing subpopulations of *S. cerevisiae* from an initial population.

Figure 21A:
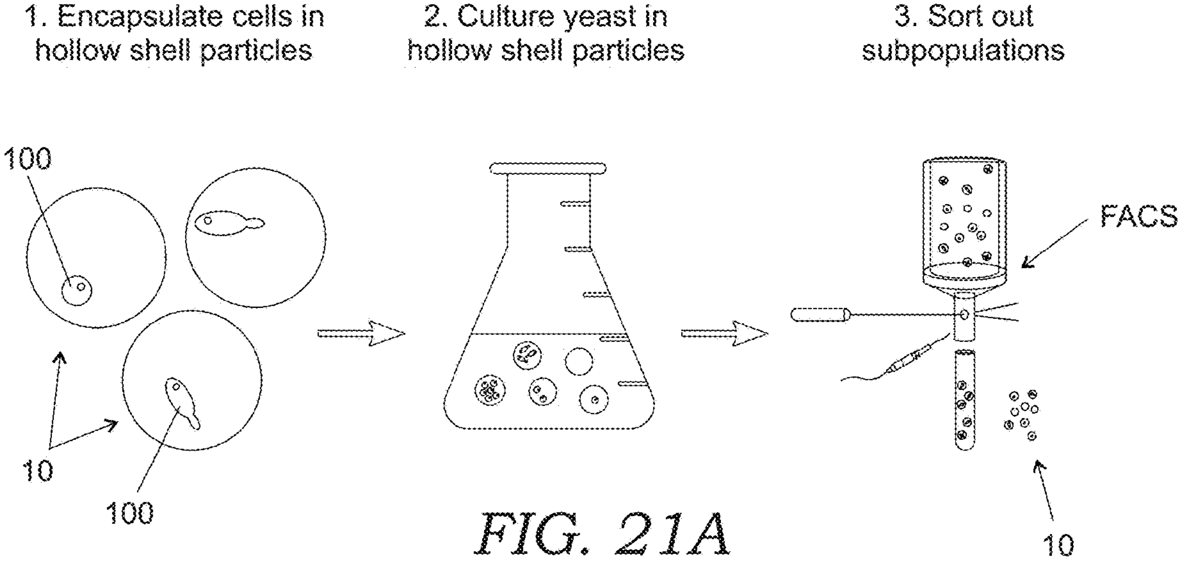
Figure 21B:
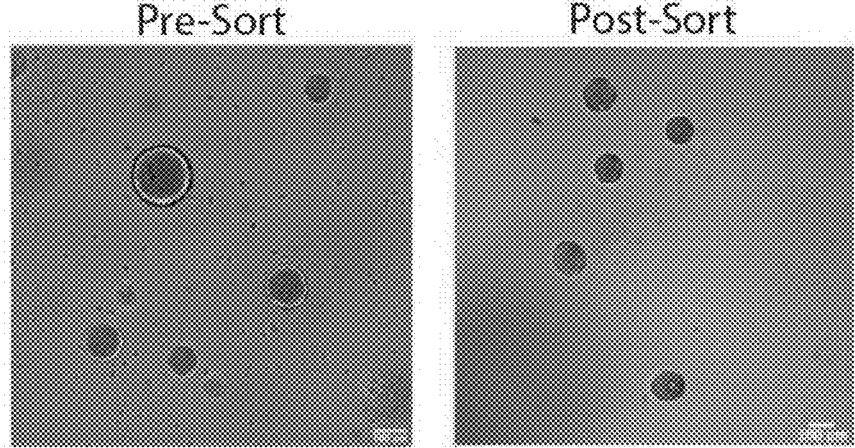

FIGS. 21A-21B: Illustrate FACS of yeast colonies in disulfide-linked hollow shell particles. FIG. 21A is a schematic illustrating general hollow shell particle workflow using FACS to isolate high-growing mutants from an initial yeast population. *Saccharomyces cerevisiae* were encapsulated into hollow shell particles crosslinked with PEG-OPSS and DTT. Cells were initially encapsulated at a concentration such that 10% of hollow shell particles contained a single cell and cell-containing particles were incubated in standard culture conditions for *S. cerevisiae* for 18 hours. Hollow shell particles were then run through a SONY SH800S cell sorter. Hollow shell particles containing the fastest growing colonies were selected and sorted out from the bulk sample based on a combination of GFP fluorescence and forward/side scatter. FIG. 21B shows representative pre- and post-sort images illustrating the FACS-mediated enrichment of fast-growing *S. cerevisiae* colonies.

Figures 22A, 22B:
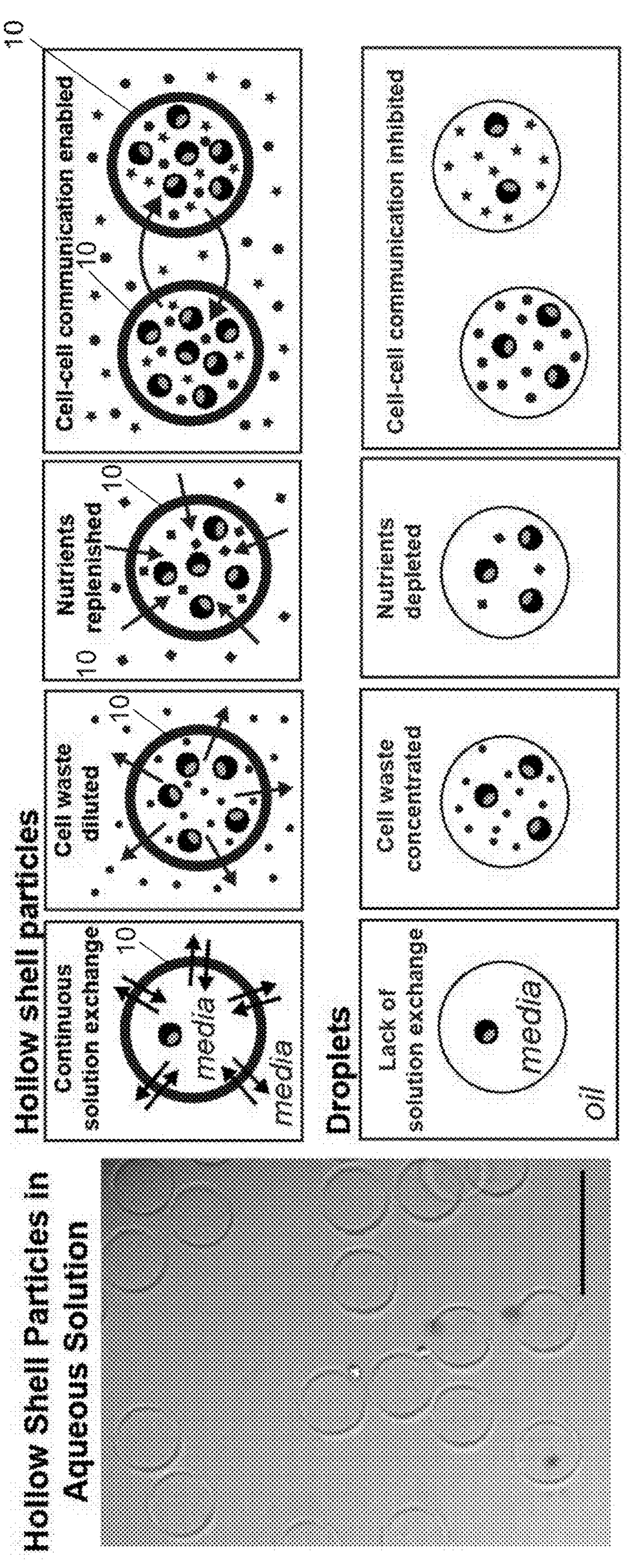
Figures 22C, 22D:
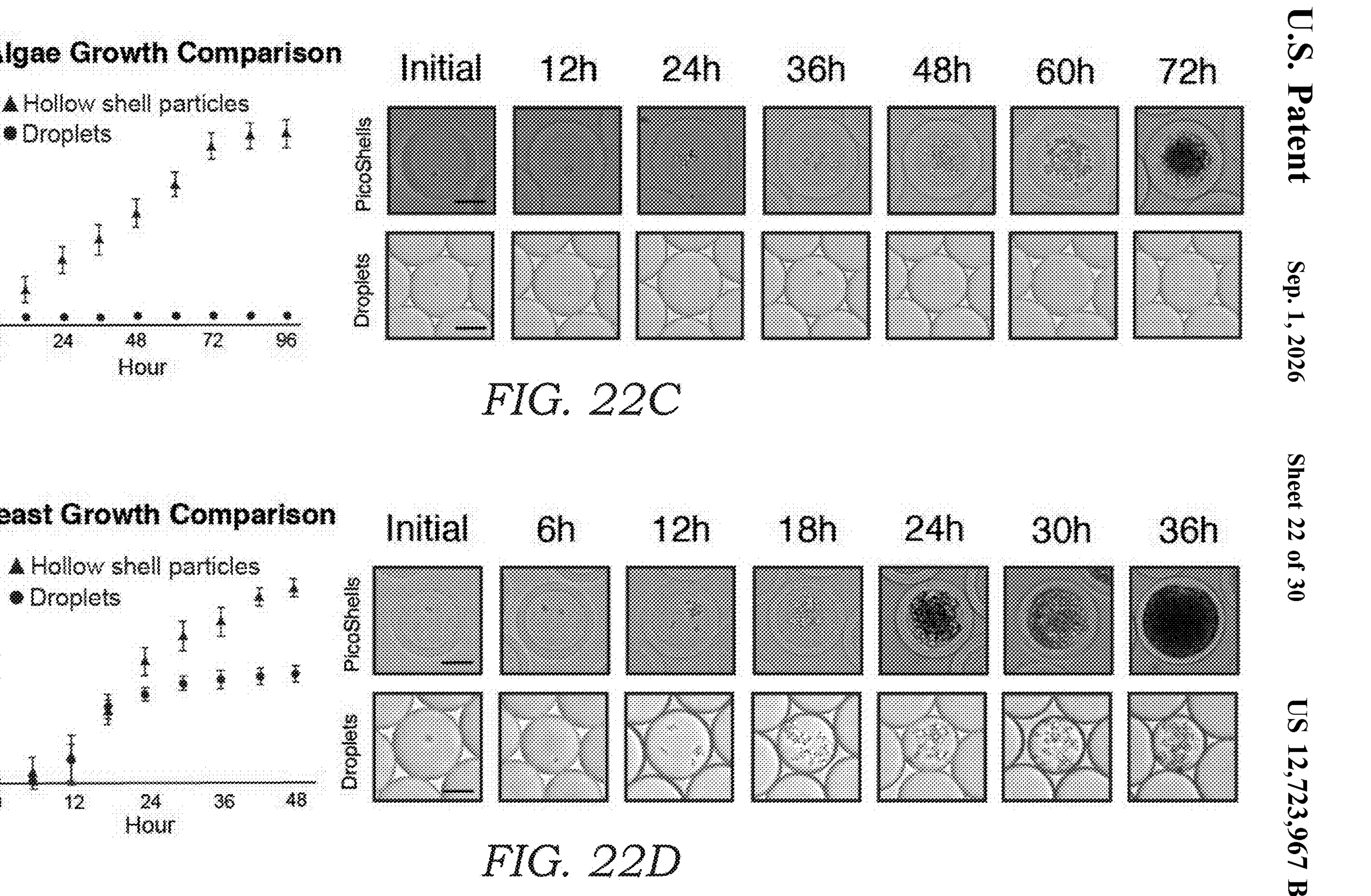
Figures 22E, 23A, 23B:
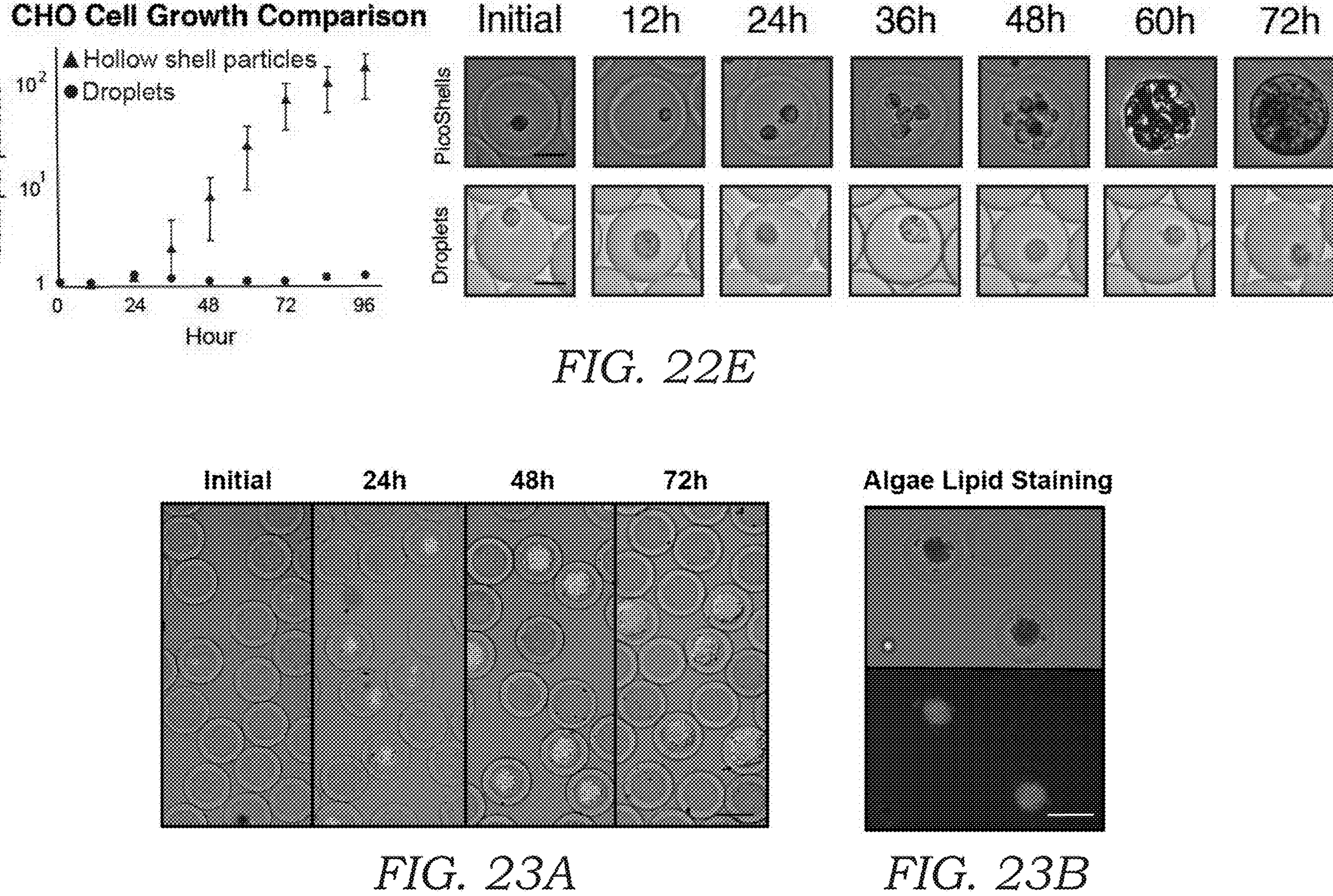

FIGS. 22A-22E illustrate the growth comparison between hollow shell particles and emulsion droplets. FIG. 22A illustrates hollow shell particles that are solid spherical particles that contain a hollow inner cavity and a porous outer shell. Scale bar=200 μm. FIG. 22B shows schematically how hollow shell particles allow for continuous solution exchange with the external environment such that cell waste can be diluted, nutrients replenished, and cell-cell communication factors can pass between adjacent hollow shell particles and with the surrounding environment. FIG. 22C illustrates the results of *Chlorella* cells that were encapsulated into hollow shell particles and droplets to compare growth rates in each compartment. Results show that the microalgae do not grow in droplets but grow readily in the particles. Scale bars=50 μm. FIG. 22D shows results for *S. cerevisiae* cells that were also encapsulated into hollow shell particles and droplets to compare growth rates. The yeast initially grow at the same rate in both compartments but growth eventually slows down in droplets. Scale bars=50 μm. FIG. 22E shows results for CHO cells in both hollow shell particles and droplets. Scale bars=50 μm.

FIGS. 23A-23E illustrate the screening and sorting characterization of microalgae loaded into hollow shell particles. FIG. 23A illustrates hollow shell particles that were loaded with *Chlorella* at lambda=0.1 and allowed to grow for 48 h. The biomass of *Chlorella* can be characterized via the chlorophyll autofluorescence that appears in the Cy5 channel. FIG. 23B shows the lipids in encapsulated *Chlorella* cells were stained with the addition of BODIPY 505/515.

Figure 23C:
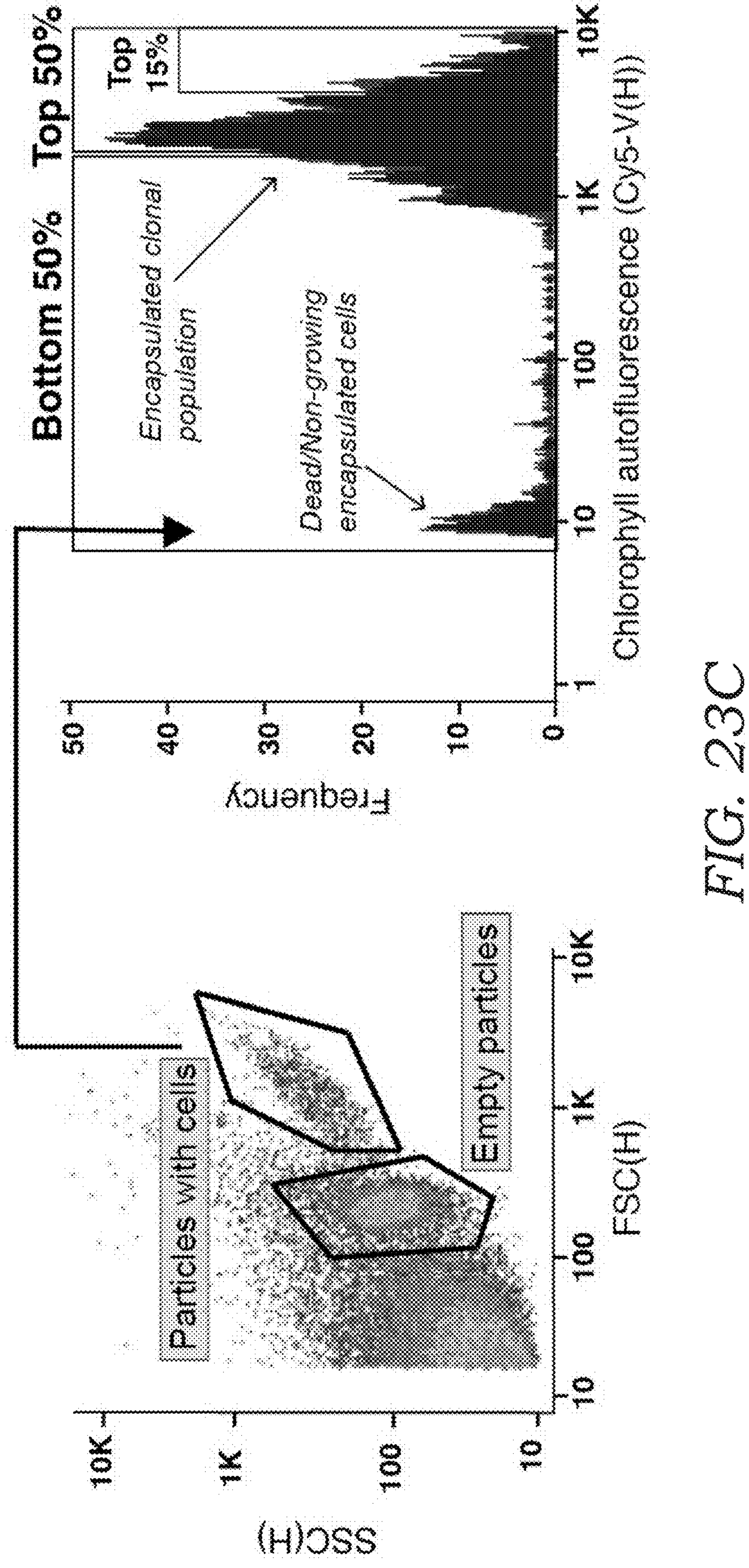
Figures 23D, 23E:
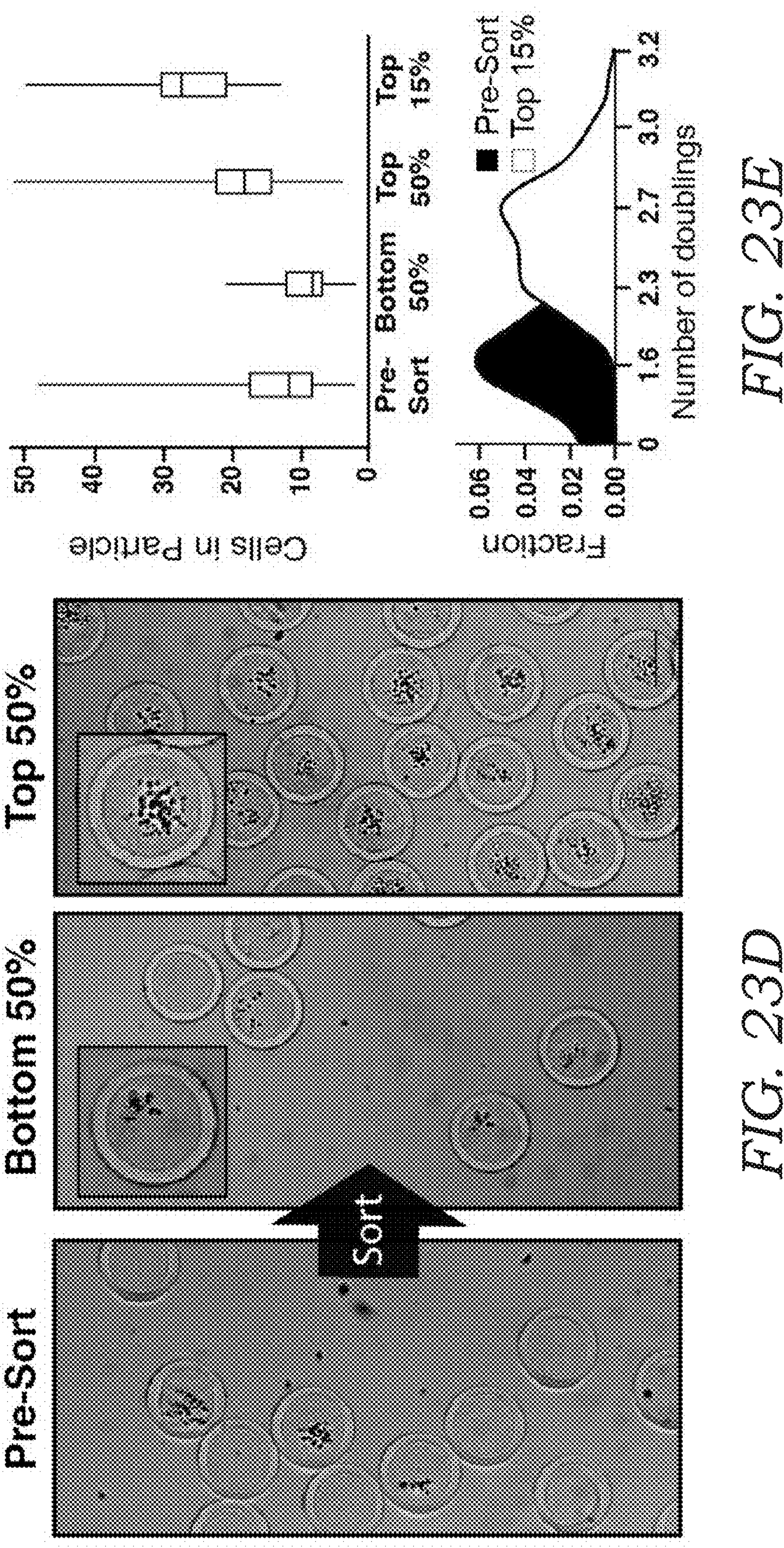

Localization of the stain were observed in the FITC channel. After allowing *Chlorella* to accumulate biomass in hollow shell particles, the particles were screened using an On-Chip Biotechnologies Cell Sorter (FIG. 23C). Particles that contain colonies and cells can be distinguished from empty particles using scatter readouts. Colony-containing particles produce an observable Cy5 fluorescence distribution via the colony's chlorophyll autofluorescence. The colony-containing particles that produced the lowest 50%, highest 50%, and highest 15% Cy5 fluorescence readouts were sorted with 94.0% purity and 72.7% yield (FIG. 23D). 200 particles were sorted in each sample. Selection of colony-containing hollow shell particles from different regions of the Cy5 distribution corresponds to particles containing different amounts of algal biomass, with particles with higher Cy5 fluorescence readouts containing more cells than those with lower Cy5 fluorescent readouts (FIG. 23E). Particles sorted from the higher end of the Cy5 distribution contain colonies that have undergone more doublings and have accumulated more biomass during the incubation period. Scale bars=50 μm.

Figures 24A, 24B:
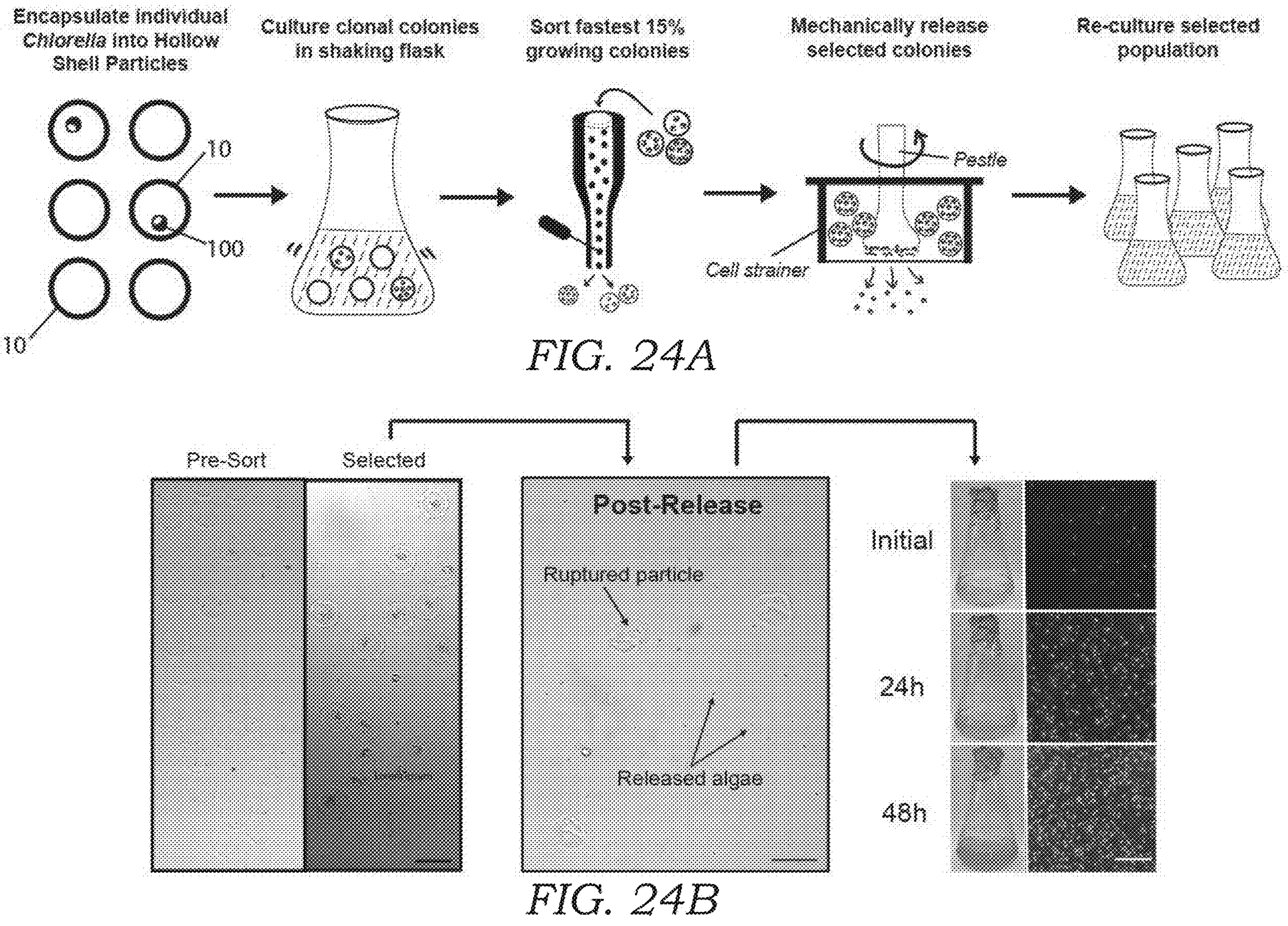
Figures 24C, 24D, 24E:
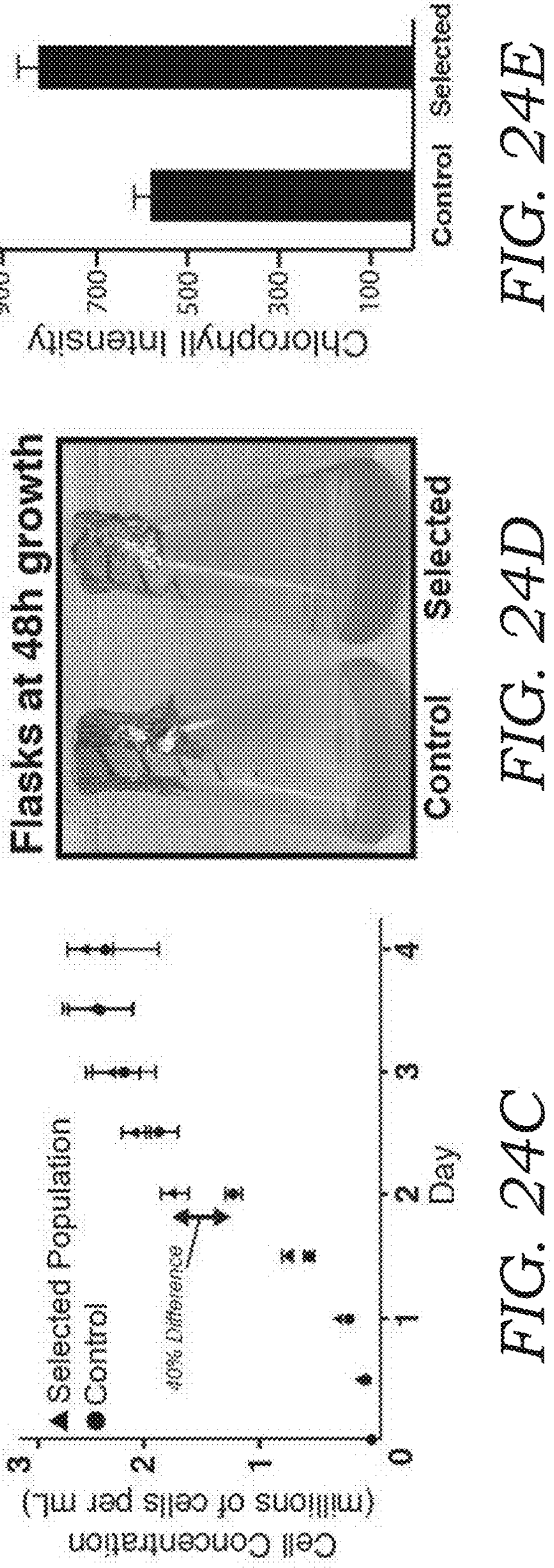

FIGS. 24A-24E illustrates the selection of a hyper-performing *Chlorella* sub-population based on biomass accumulation rate. FIG. 24A illustrates the workflow. Single *Chlorella* were encapsulated into hollow shell particles and incubated under standard culturing conditions in a shaking flask to allow cells to accumulate biomass. Colony-containing hollow shell particles from the top 15% of the Cy5 fluorescence distribution were selected by FACS and mechanically released from particles. Released cells were then re-cultured for further analysis. From a particle population of 121,213 particles (3839 containing colonies), 425 particles were selected. Selected particles were ruptured on top of a cell strainer, causing selected algae to be released into fresh culture media. This sample was re-grown in an Erlenmeyer flask under standard culturing conditions for several days (FIG. 24B). The selected population and an un-selected population were seeded in separate flasks at the same concentration and their cell concentrations were tracked for 4 days (FIG. 24C). The selected population had an 8% faster growth rate (10.2 h doubling times) than the un-selected population (11.2 h doubling time) for the first 48 h after seeding before slowing down as the culture reached carrying capacity. The largest difference in biomass accumulation was observed at 48 h after seeding (~40% difference in cell concentration), a difference that can be visibly seen in the green color of the cultures (FIG. 24D). The difference in biomass accumulation was verified by measuring the chlorophyll density of each sample with a well plate reader at 48 h after seeding (FIG. 24E). The selected population was measured to have a 27.6% higher chlorophyll density (P<0.05). Scale bars=100 μm.

Figure 25:
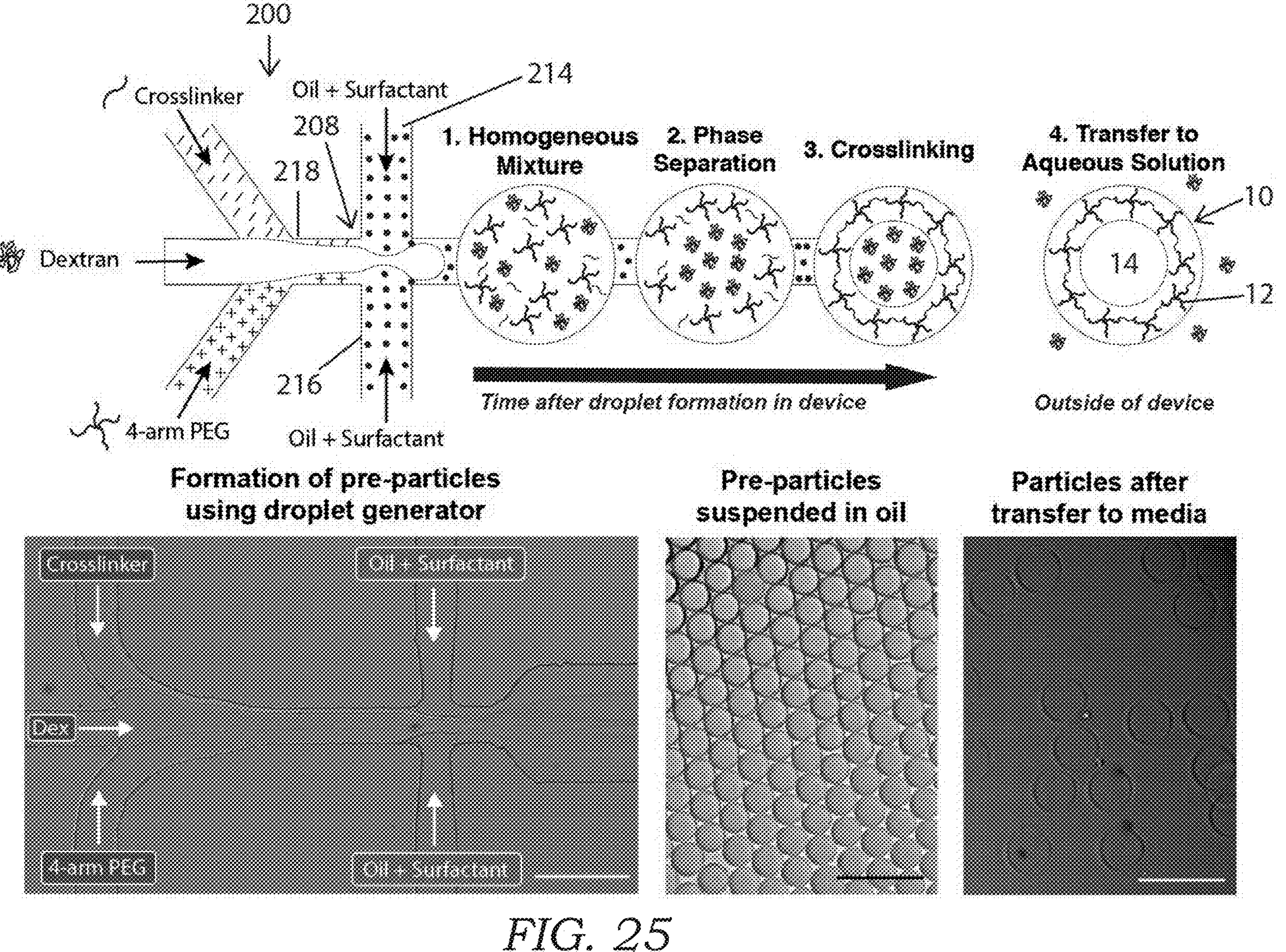

FIG. 25 illustrates the microfluidic fabrication of hollow shell particles. Hollow shell particles are formed by mixing together crosslinker, dextran, and 4-arm PEG to form a water-in-oil droplet emulsion. The reagents are mixed in the microfluidic droplet generator immediately before droplet formation to reduce premature gelation. After droplet generation, the 4-arm PEG and dextran phase separate as the droplet travels down the channel. As 4-arm PEG and dextran separate, the crosslinker and 4-arm PEG react. Following gelation, the hollow shell particles are phase transferred from oil to aqueous solution and dextran leaks out of the hollow shell particles via pores in the outer shell. The outer diameter of hollow shell particles is larger than that of pre-particles (~90 μm and ~70 μm respectively) due to the expected swelling of the PEG hydrogel in aqueous solutions. Scale bars=200 μm.

Figure 26:
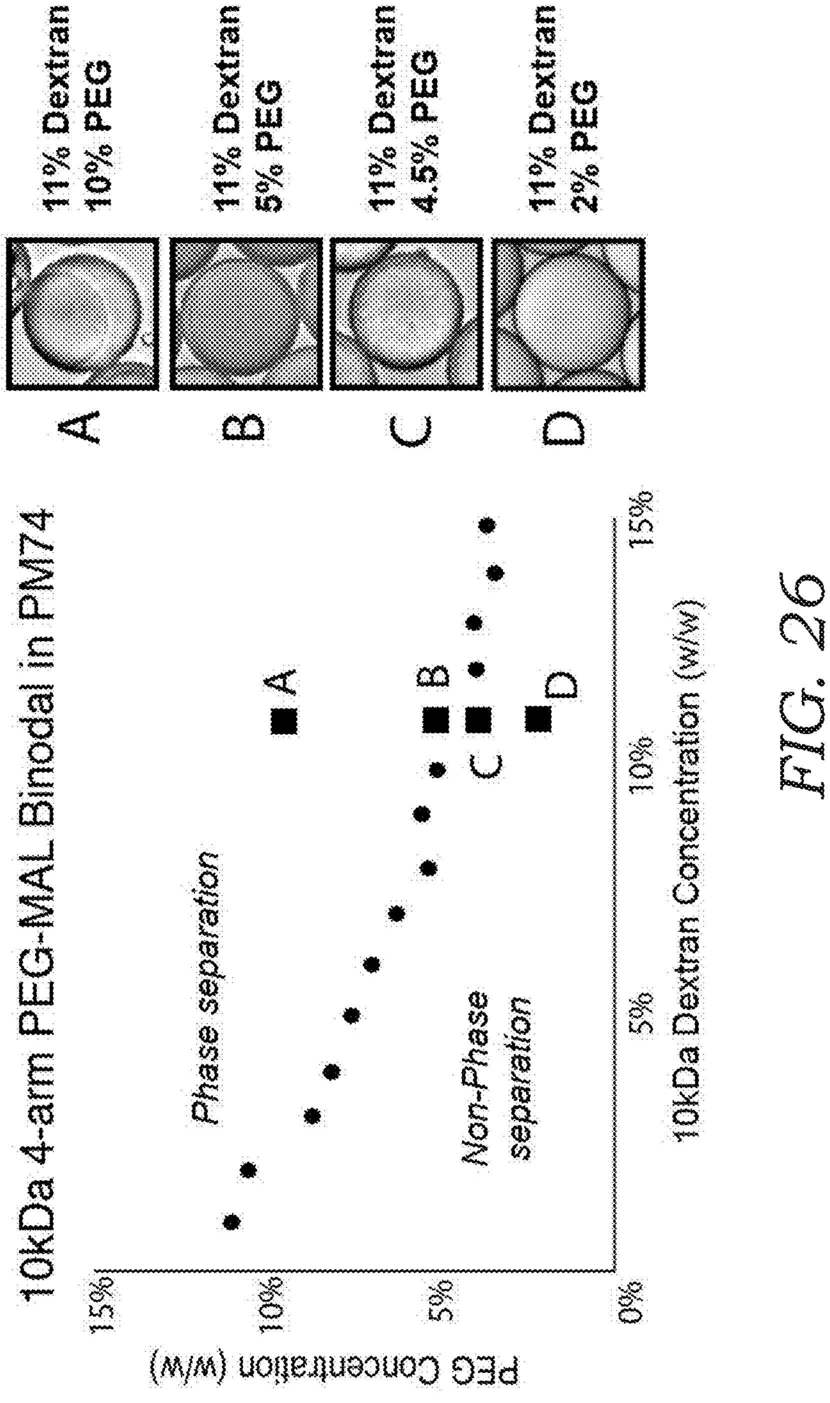

FIG. 26 illustrates the phase diagram of 10 kDa 4-arm PEG-maleimide and 10 kDa dextran in PM74 seawater medium. Black dots represent concentrations that were experimentally determined where the binodal is located through visual observation of droplets with varying concentrations of PEG and Dextran. PEG and dextran concentrations below the binodal curve do not result in phase separation. PEG and dextran concentrations above the curve result in noticeable phase separation. Hollow shell particles are formed by mixing PEG and dextran at in-droplet concentrations within 0.5-2% above and to the right of the points on the binodal curve.

Figures 27, 28:
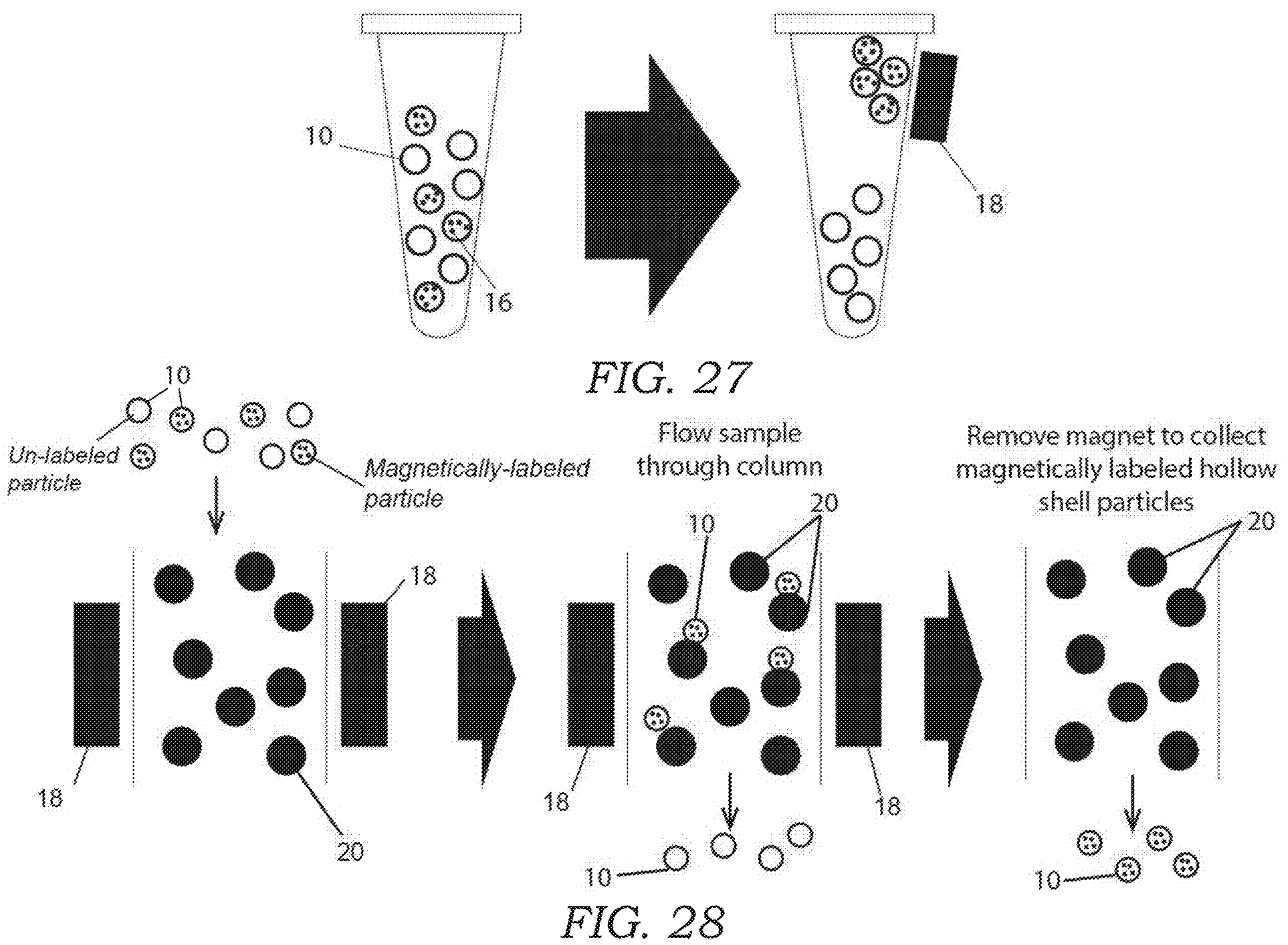

FIG. 27 illustrates one embodiment of using magnetic forces to separate or sort hollow shell particles using a magnetic label that is incorporated into the hollow shell particles.

FIG. 28 illustrates another embodiment of using magnetic forces to separate or sort hollow shell particles using a magnetic label that is incorporated into the hollow shell particles. In this embodiment, sample containing the magnetically labelled hollow shell particles are flowed through a column containing reversibly magnetized (e.g., ferromagnetic) microspheres.

DETAILED DESCRIPTION OF ILLUSTRATED EMBODIMENTS

Hollow Shell Particle Specifications

Figures 1A, 1B, 1C:
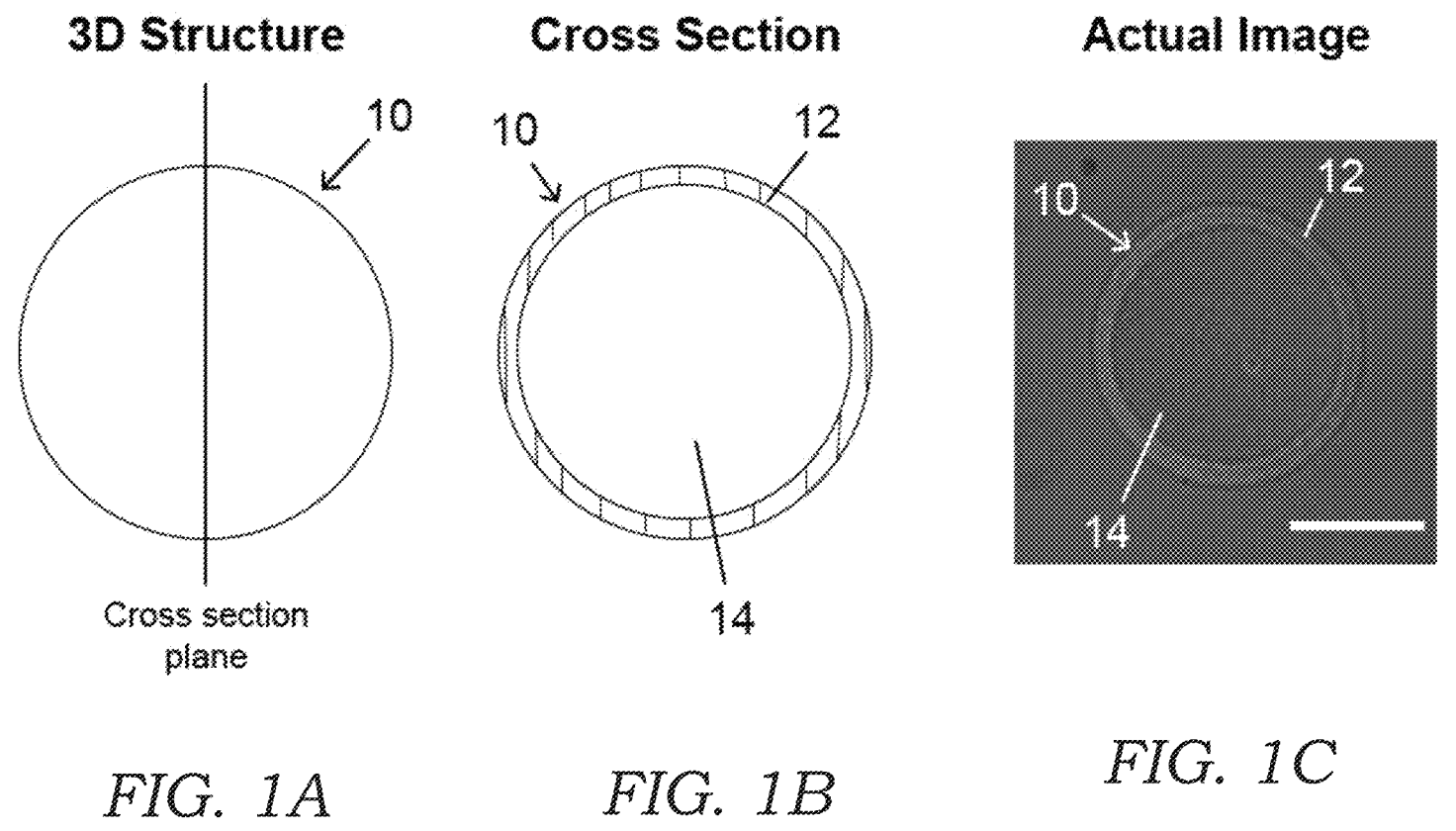

The hollow shell particles 10 have spheroidal shapes and include a solid exterior shell 12, and a hollow inner cavity 14 that contains little to no solid material (FIGS. 1A-1C). The overall size of the hollow shell particles 10 generally ranges from 5-500 μm. Hollow shell particles 10 suitable for enclosed cells 100 such as yeast, mammalian cells, or microalgae are preferably >30 μm in outer diameter. For use with flow cytometers or fluorescence activated cell sorters hollow shell particles 10 are preferably also <60 μm in diameter or <100 μm in diameter for large particle flow cytometers and sorters. The diameter of the inner cavity 14 can range from 1 μm to 499 μm. The hollow shell particles 10 within a particular batch can either be uniform in size (CV<10%) or non-uniform in size (CV>10%). Such variation of sizes within a batch may be dependent upon the method of particle fabrication (e.g., microfluidic droplet techniques vs bulk emulsifiers). The thickness of the solid exterior shell 12 does not have to be uniform and can have a CV ranging from 0-25%. The volume of the inner cavity 14 can take up 1-99% of the total particle volume. The hollow shell particles 10 are circular or elliptical in at least one cross-sectional plane. The hollow shell particles 10 are stable in aqueous solution for at least 30 min without any chemicals that degrade structurally stabilizing elements within the solid phase or physically adverse conditions such as high shear or pressure. The hollow shell particles 10 are made from biocompatible materials, preferably hydrogel materials, that induce little to no damage to enclosed cells 100 and organisms desired for the assay of interest. The system of hollow shell particles 10 may include large numbers of hollow shell particles 10 that may include thousands or tens of thousands (e.g., more than 10,000 hollow shell particles 10), hundreds of thousands of hollow shell particles 10, or more.

General Particle Fabrication Strategy

Figure 2:
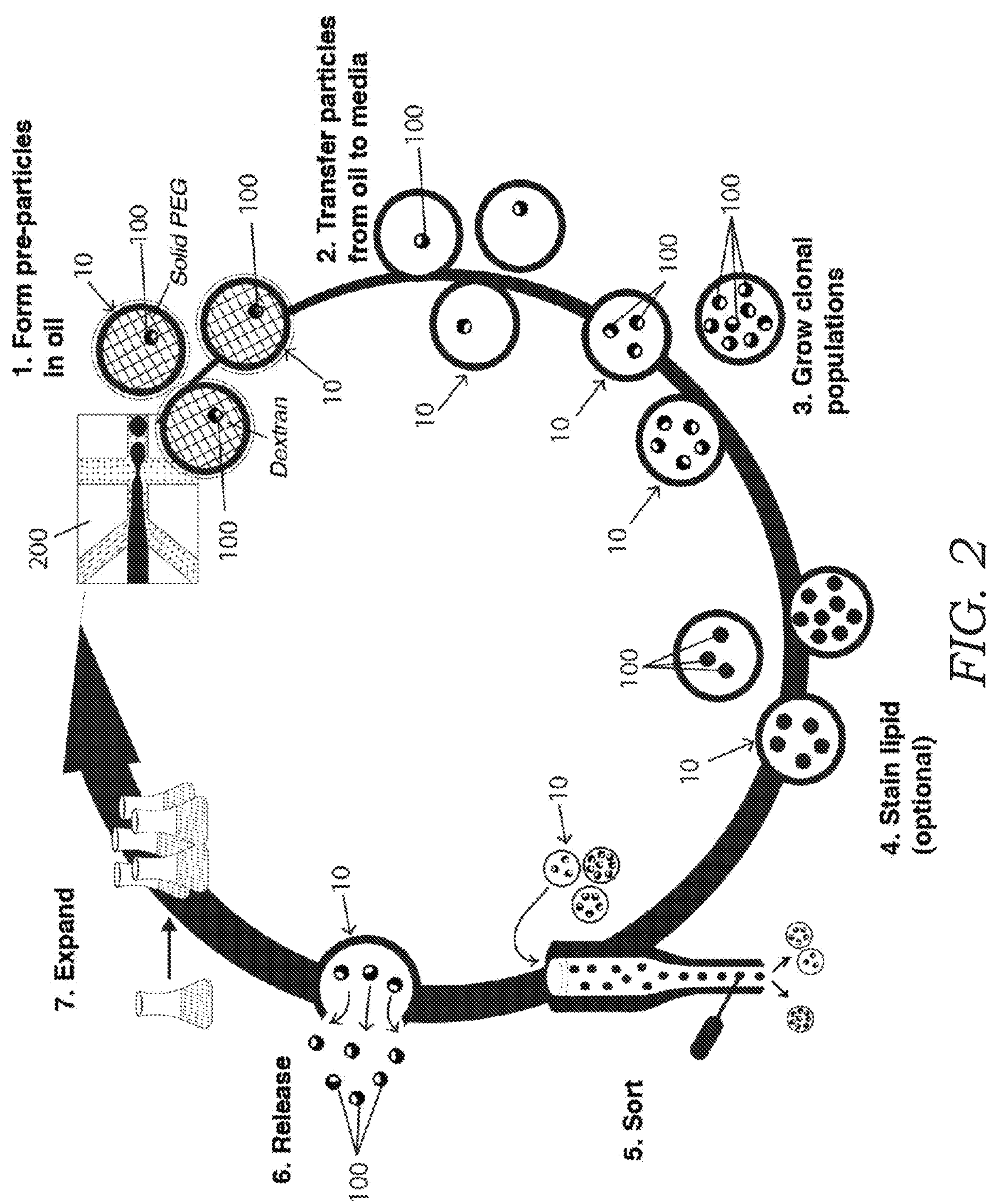
FIG. 2: Workflow to screen cells using hollow shell particles. (1) Particles are formed using droplet microfluidics, aqueous two-phase systems (ATPS), and polymer chemistry. Particles are initially formed within an aqueous droplet surrounded by oil. Cells are within the inert polymer phase, which is surrounded by a solid polymer matrix. (2) Soon after particle formation, the particles are transferred into the cell's native media. Pores in the outer solid shell allow for inert, un-solidified polymer to leak out. Pores also allow for continuous solution exchange between the inner cavity and the external aqueous environment. (3) Cells may grow within particles over multiple days to form clonal populations or exhibit some other phenotypic property over a desired time frame. (4) Pores in the solid matrix allow for enclosed components to be labeled with fluorescent stains, magnetic labels, metallic labels, etc. (5) High-performing populations can be sorted using FACS with scatter and/or fluorescent readouts or magnetic separation approaches. (6) Sorted particles can be broken down by adding reagents that cleave degradable motifs in the solid polymer matrix of the particle. Particles may also include motifs that allow for photocleavage or mechanical breakdown of particles. Such breakdown is designed to release cells from the particles (7) Released cells remain viable and/or have very little damage and can be re-cultured for further analysis, culture, and/or processing.

Hollow shell particles 10 are formed via a combination of droplet technology, aqueous two-phase systems (ATPS), and polymer chemistry. In one exemplary approach, cells 100, oil, emulsification stabilizers (surfactants), and precursors materials (biocompatible pre-polymer and biocompatible inert material) are mixed collectively or separately to form water-in-oil emulsions. Non-uniform emulsions (CV>10%) can be formed by manually agitating (e.g., pipetting, mixing, vortexing) the previously mentioned reagents together or by emulsifying the reagents together in an automated bulk emulsification system. Uniform (CV<10%) or non-uniform emulsions can be formed using microfluidic droplet generators 200 such as those illustrated in FIGS. 4A, 4B, 5A, 7A, 13A (step emulsification device 250), 25 that form droplets using droplet generation principles such as flow-focusing, cross-flow, step-emulsification, and co-flow. The precursor materials should be able to partition into two or more phases and one of the phases, that is rich in pre-polymer, should localize to the outer radius of the droplet to form an outer layer and should be capable of crosslinking to form a solid polymer matrix. To form hollow shell particles 10, the concentration of the pre-polymer should be sufficiently low in the inner phase(s), such inert materials in the inner phase(s) do not crosslink or have a polymerization process that is kinetically hindered. Following phase separation within the droplet the crosslinkable pre-polymer material structured in the phase-separated configuration is crosslinked using a biocompatible polymerization chemistry. The hollow shell particles 10 are then transferred out of the oil phase into an aqueous phase. The crosslinking material or pre-polymer contain one or more motif(s) that can be degraded using a biocompatible mechanism, inducing a destabilization of the hollow shell particles 10 and release of enclosed materials (e.g., cells 100). Alternatively, the crosslinked polymer shell is degradable through mechanical means, such as pressure, fluid shear stress, mechanical stretch, etc. Encapsulated cells 100 or cell colonies are allowed to exhibit a desired phenotypic property, labeled, if necessary, sorted/screened, and released from the hollow shell particles 10, and then certain cells 100 or subpopulations are analyzed and/or expanded. FIG. 2 illustrates an example of this workflow.

Aqueous Two-Phase System (ATPS)

ATPS systems are broadly defined as a combination of water-soluble polymers, polymer and salts, or multiple salts that are immiscible at specific concentrations/temperatures, etc. By mixing various components of an ATPS system within water-in-oil droplets at or near these immiscible conditions, the various ATPS components phase separate into distinct regions creating unique multi-material morphologies (FIG. 3). In some embodiments, such as PEG-dextran ATPS systems, the morphology of the resulting droplets can be described using a phase diagram. The phase diagram typically contains a binodal curve which defines a boundary as a function of the concentration of the ATPS components. At concentrations above the binodal for either of the two components phase separation occurs (two-phase), while concentrations below the binodal lead to a single phase. The phase diagram depends on a number of properties such as: type of polymers used (PEG, Dextran, gelatin, etc.), molecular weight of those polymers, functional groups present on the polymers (maleimide, vinyl-sulfone, thiols), buffer/salt concentrations, pH, temperature, etc. Shell thickness and cavity size is controlled by the ratio of the ATPS components. A higher ratio of pre-polymer material to non-polymerizable components results in a larger shell thickness and smaller cavity size and a lower ratio results in a smaller shell thickness and larger cavity size (FIG. 3).

It was found that the appropriate morphology forms when the concentrations of the ATPS components are above and to the right of the binodal line but within a close vicinity (e.g., within <0.25-2% weight fraction). For example, for PEG/dextran materials used as ATPS components, it was found that when droplets contain PEG/dextran concentrations within 1-2% into the phase separation region above and to the right of the binodal, the dextran orients in the center of the droplet with PEG uniformly surrounding the dextran at the aqueous-oil interface. Crosslinking the PEG phase at these concentrations results in formation of the PEG-based hollow shell particles 10 that can remain stable when transferred out of oil and into aqueous solution (e.g., Dulbecco's Phosphate-Buffered Saline (DPBS), media, etc.).

Materials within the droplets can be polymerized to form hollow shell particles 10 if the droplets contain a pre-polymer material. Janus-shaped droplets or single phase-droplets form outside of the vicinity of the binodal (FIG. 3). In some embodiments hollow shell particles 10 can be fabricated at regions further away from the binodal line by optimizing the physical confinement of the droplets during polymerization. That is, when the droplets are sized to be similar or larger than the size of the channel in which they are polymerized, formation of hollow shell particles 10 is more preferred.

Collecting a Binodal Curve

Obtaining the binodal curve before optimizing the particle development makes it much easier to determine the ideal polymer concentrations to form hollow shell particles 10 using an ATPS. The ATPS binodal curve is affected by many parameters (e.g., buffer, polymer type, polymer molecular weight, salt concentration, pH, etc.). By collecting the binodal curve every time the parameters are changed, a greater understanding of the system is obtained that allows one to more rapidly determine the appropriate ATPS conditions (e.g., polymer concentrations) to obtain hollow shell particles 10.

Traditional collection of the binodal curve involves placing different concentrations of the desired polymers in test tubes and visually determining phase separation. While thoroughly developed and widely used, this traditional method is limited for the ATPS application. First, collection of a large number of points along the curve requires a significant amount of labor and uses large amounts of reagents that are potentially expensive. Second, behavior of the ATPS in bulk may be different than that in water-in-oil droplet emulsions, potentially making it difficult to translate the collected binodal curve from one environment to the other.

Figures 5A, 5B, 5C:
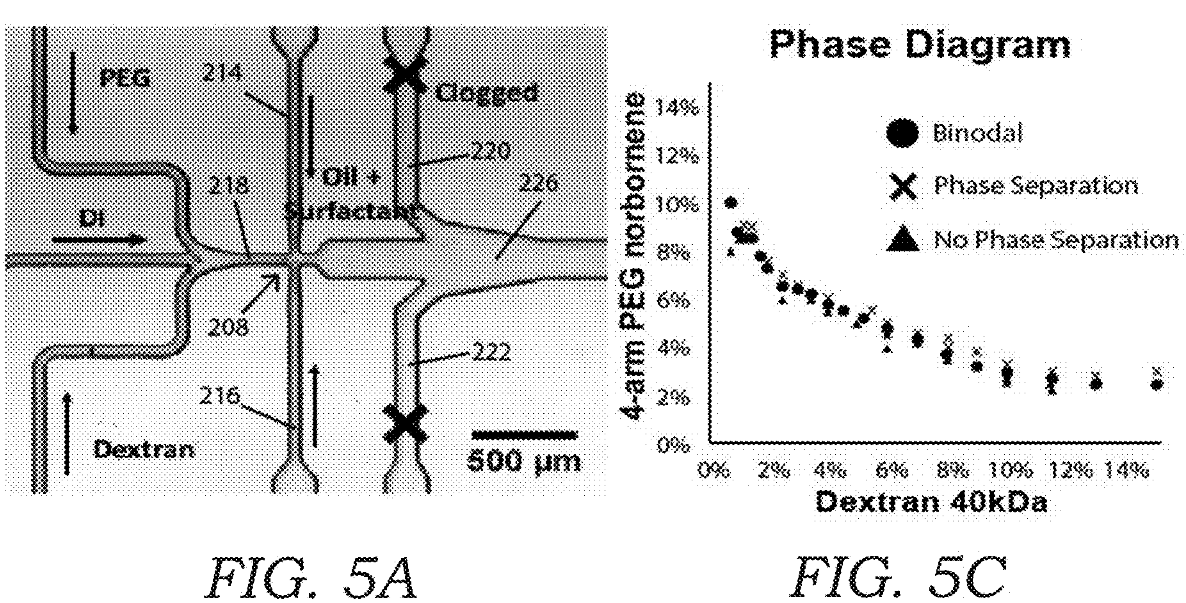
FIG. 5A shows the microfluidic droplet generator device highlighting materials entering different inlets and droplet generation point for DI water as the sample. PEG, DI water, and dextran can be switched in any order. DI water can be changed for other solutions such as cell media or PBS.
FIG. 5B illustrates images of different types of PEG-dextran interactions within droplets that can be observed at different concentrations. In the case of no phase separation, there is no distinct difference between the dextran and PEG phases. Concentrations where phase separation is seen results in two distinct solutions with a clear interface. In between concentrations resulting in phase separation and no phase separation, there is a regime where there is a turbid solution within the droplet that is distinguishable from the rest of the droplet solution but does not have a clear interface.
FIG. 5C a phase diagram that shows that by visually determining no phase separation, phase separation, or binodal at different concentrations, one can plot out regimes where each exists within a diagram. Using this information, one can estimate the location of the binodal curve and optimal regions above the binodal for hollow shell particle formation.
Figures 6A, 6B, 6C, 6D:
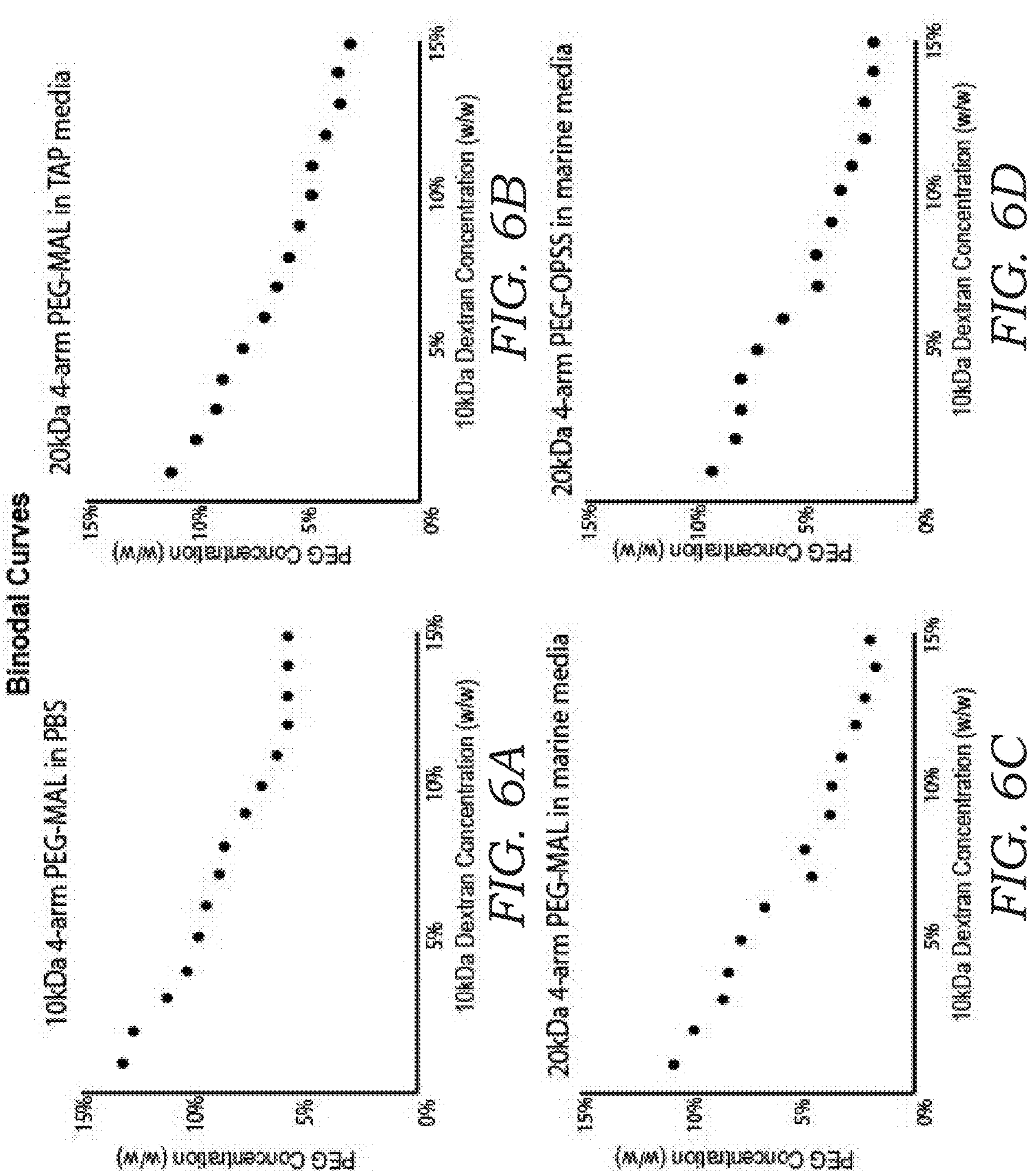
FIGS. 6A-6D illustrate binodal diagrams for various PEG types/media and dextran conditions at dextran concentrations between 1 and 15% in increments of 1%. Changes in media, molecular weights, and PEG precursor chemistries and molecular weights can result in shifts of the binodal curve.

To address the above limitations, a novel droplet-based method was developed to rapidly calculate binodal curves for the desired ATPS. The desired media, potential pre-polymers and inert materials dissolved in the desired media, and oil with surfactant are loaded into separate inlets of a 3-inlet flow focusing microfluidic droplet generator 200. Design of the microfluidic droplet generator 200 and an example system involving 4-arm PEG-Norbornene (10 kDa), dextran (40 kDa), and PBS are shown in FIGS. 4A, 4B and FIG. 5A respectively. In this particular example, 4-arm PEG-Norbornene is a potential pre-polymer and dextran is a potential inert material. In this embodiment, the three phases are co-injected with syringe pumps into separate channels of the microfluidic droplet generator 200. The microfluidic droplet generator 200 includes three inlets 202, 204, 206 that deliver the aqueous-based solutions to a droplet generation region 208. Two other inlets 210, 212 are provided that carry the oil phase and surfactants. Droplets are formed at the droplet generation region 208 where the pair of channels 214, 216 carrying the oil/surfactant interface with a merged channel 218 (FIG. 4B) carrying the aqueous-based solutions (and cells 100). Two additional downstream channels 220, 222 carry the oil phase and surfactants which can aid in droplet generation within the microfluidic droplet generator 200. It should be appreciated that these two additional downstream channels 220, 222 and the inlet 212 may be omitted in some embodiments. An outlet is provided 224 that carries the droplets/hollow shell particles 10 via a channel 226 fluidically coupled to the droplet generation region 208. In addition, it is possible to reduce the number of inlets 202, 204, 206 to just two inlets by having the crosslinker and dextran in the same inlet.

The three channels are merged together prior to a cross junction that introduces an oil phase (e.g., Novec™ 7500+0.5% Pico-Surf™) which pinches off the three combined aqueous phases into droplets. After droplet formation, the various polymer components mix together in an outlet channel and depending on the concentration of components will undergo phase separation. The final concentration of PEG and Dextran, or other ATPS system being studied, can be rapidly adjusted by adjusting the relative flowrates of the PEG, dextran and PBS solutions being injected. As the droplets flow in the channel, the user can visually determine with a microscope (or other imaging device) whether the final concentrations resulted in phase separation, no phase separation, or lies along a binodal. Examples of each of these conditions in droplets are shown in FIG. 5B. A user can plot the pre-polymer concentrations that result in a binodal within the droplets, effectively giving them the binodal curve within a desired region FIG. 5C. Of course, this operation may also be automated using image processing software that processes images obtained of the formed droplets. Due to the smaller volumes of the droplets, phase separation occurs more rapidly than in larger volume systems enabling rapid determination of the binodal curve. This approach requires less reagents which can be critical for more expensive functional polymers. Lastly this approach more closely represents actual conditions used for generation of the hollow shell particles 10.

Using this method, the binodal curves were obtained for the following pre-polymer materials mixed with 10 kDa dextran in the corresponding media: 10 kDa 4-arm PEG maleimide in PBS, 20 kDa 4-arm PEG maleimide in TAP media, 20 kDa 4-arm PEG maleimide in marine media (high salt concentration), and 20 kDa 4-arm PEG orthopyridyl disulfide in marine media (FIGS. 6A-6D).

Droplet Generation

Figures 7A, 7B:
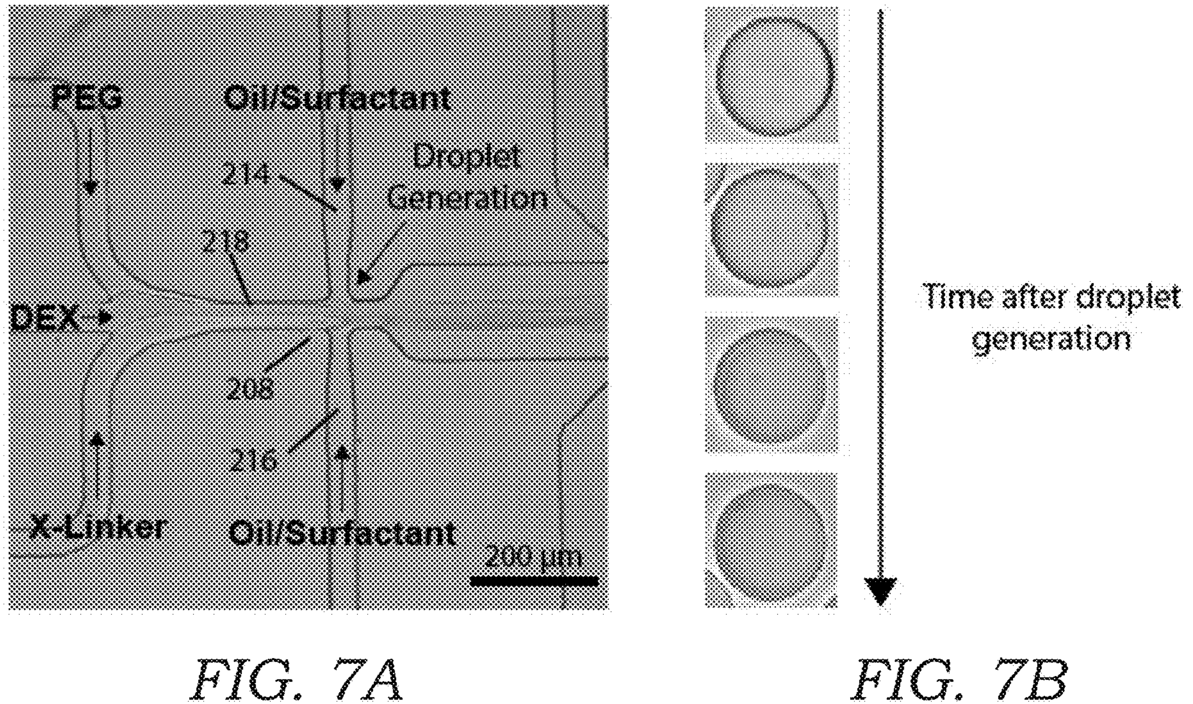
FIG. 7A illustrates the droplet generation region of a microfluidic droplet generator device to form hollow shell particles. Dissolved PEG, dextran (DEX), and crosslinker (x-linker) enter the device via separate channels and mix just prior to droplet generation. Dextran is usually flowed through the center channel to limit premature crosslinking that may occur if PEG and crosslinker mix too early. During cell encapsulation, cells are usually placed into the dextran phase. Emulsification and droplet formation occurs when the oil and surfactant flow "pinches off" the aqueous flow.
FIG. 7B illustrates time lapse images showing hollow shell ATPS in a channel. At first, there is no phase separation but the dextran and PEG phase separate over time as the polymer solutions are allowed to interact with each other. Crosslinking also occurs during this time.

In one embodiment, uniform droplets are formed and pre-polymers are mixed with inert material using a microfluidic droplet generator 200 (flow focusing, T-junction, co-flow, step-emulsification) that is made of PDMS, made of glass, or 3D-printed. In a particular embodiment, the microfluidic droplet generator 200 is designed such that various aqueous phases (including one or more phases that include cells 100) intersect right before the droplet generation region (FIG. 25). Generally, this is done to limit premature phase separation or crosslinking. In one example, PEG (pre-polymer) containing reactive functional groups, dextran (inert material), and chemically reactive crosslinker enter the device via three separate channels and mix before droplet generation (FIG. 7A). Phase separation of the PEG/dextran ATPS and crosslinking of PEG pre-polymer occurs following emulsification (FIG. 7B). Any of the aforementioned reagents may be mixed together before entering the device, assuming that premature crosslinking does not occur. Examples of oils that can be used for droplet generation include Novec™ 7500, mineral oil, hydrocarbons, and fluorocarbons. Examples of emulsification-stabilizing agents (surfactants) include Pico-Surf™, Ran Surfactant, Span80, and BioRad surfactant.

Solidification

Figures 8A, 8B:
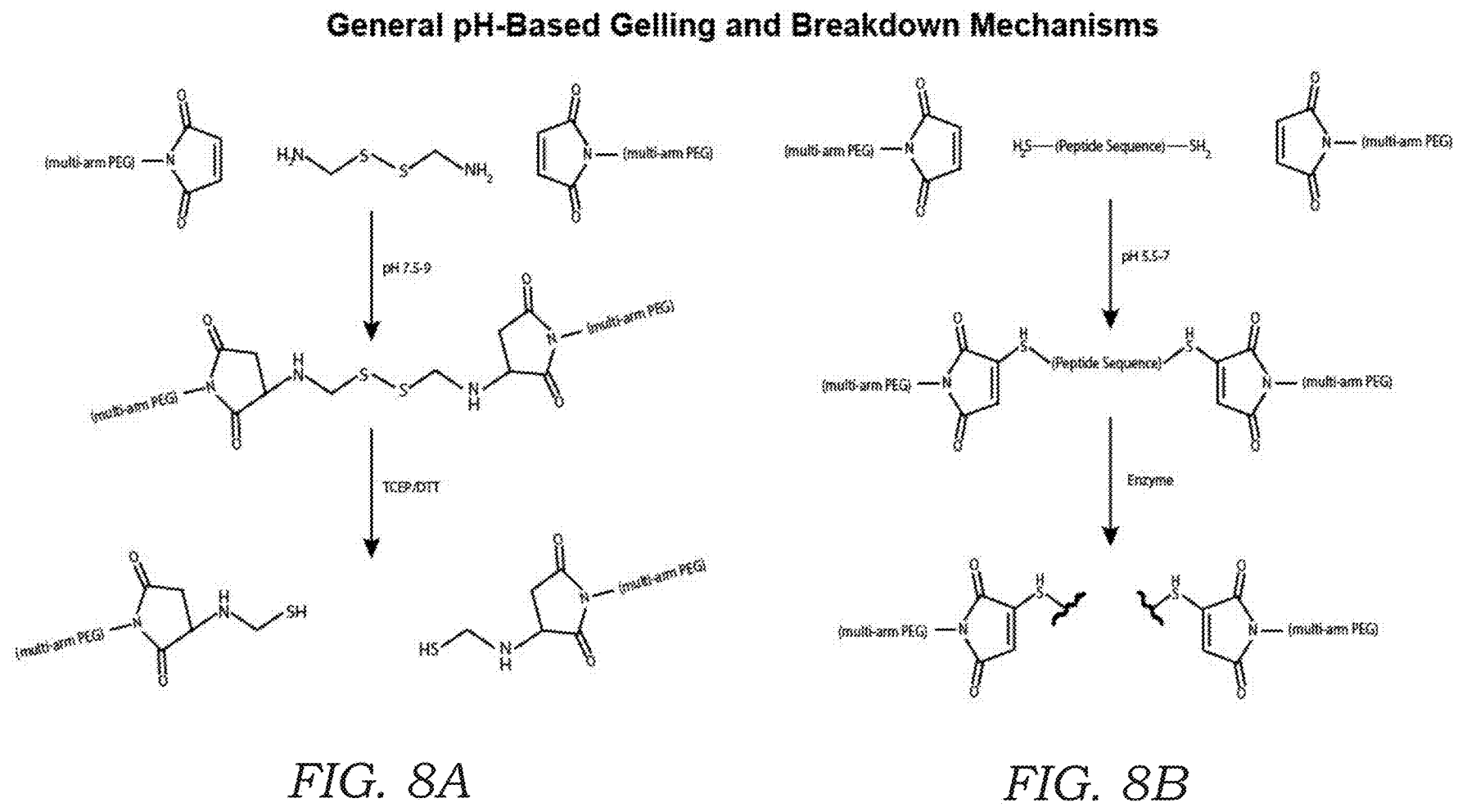
Figures 9A, 9B, 10A, 10B:
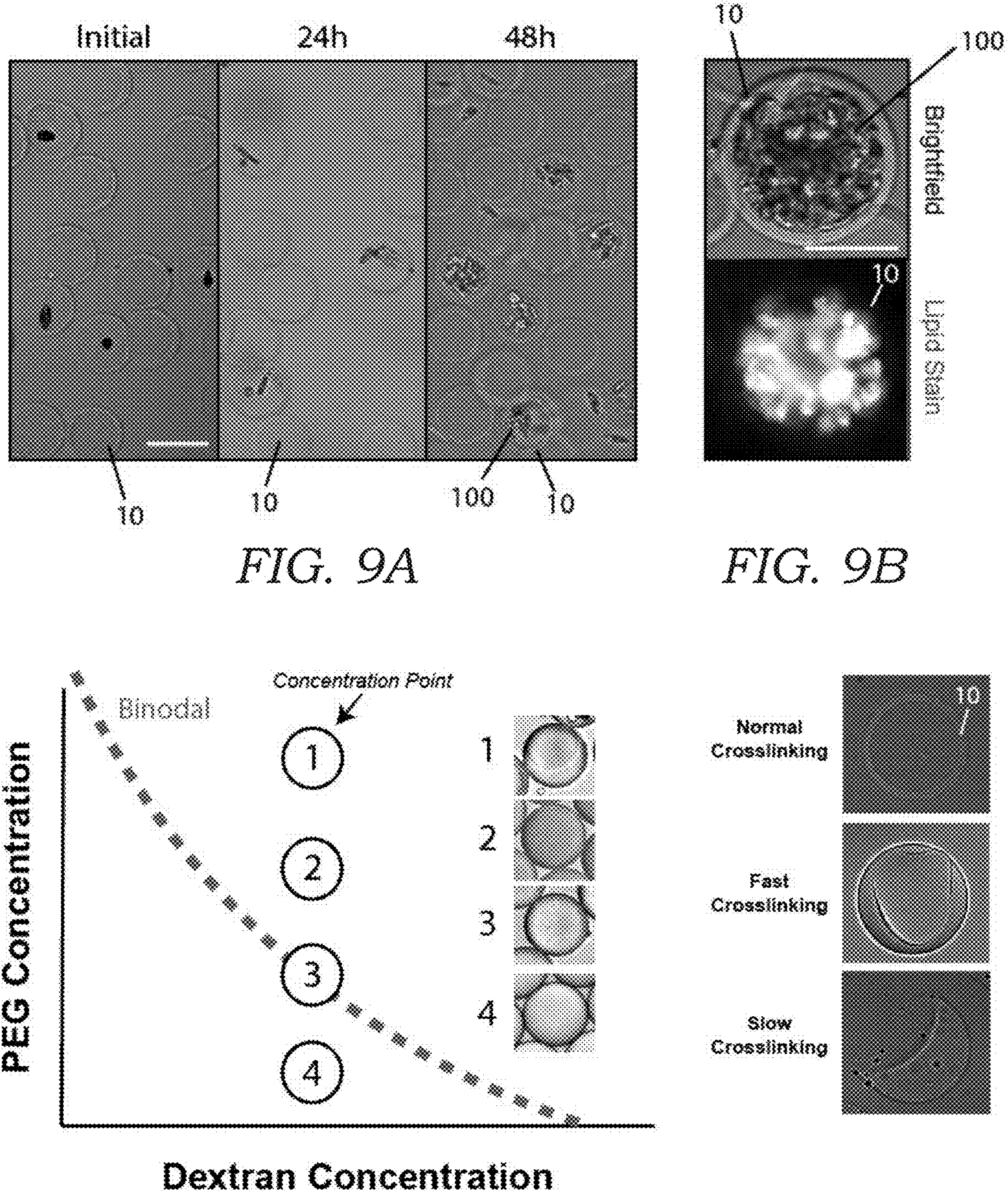
FIG. 9A shows images of *Euglena* biomass and lipid accumulation within hollow shell particles. *Euglena* cells were encapsulated into non-degradable hollow shell particles and allowed to grow over a 2-day period. The solid phase of the particles is composed of 10 kDa 4-arm PEG maleimide that has been crosslinked with dithiolthreitol (DTT). Hollow shell particles were formed using cell concentrations that resulted in ~90% of cell-containing particles enclosing no more than on cell. It was demonstrated that *Euglena* are viable and can accumulate biomass within hollow shell particles over a 2-day period. Scale bars=100 μm.
FIG. 9B illustrates stained images of hollow shell particles that were exchanged into a solution with BODIPY after the 2-day incubation period to fluorescently label lipids within the encapsulated algae. Stains were able to transport through the solid polymer matrix of the hollow shell particles and label cells without sticking a significant amount to the particle's PEG surface.
FIG. 10A illustrates a phase diagram showing the location on the binodal where hollow shells are formed. At concentrations below the binodal, there is no phase separation which results in a solid particle. At the binodal, there is slight phase separation but not enough to create a hollow inner cavity. Concentrations directly above the binodal result in full phase separation and is within a regime that results in a hollow shell after crosslinking.
FIG. 10B: Illustrates the effects of different crosslinking speeds on final particle shape. When crosslinking is too fast, the ATPS system never reaches an approximately equilibrium shape, and the resulting particles either have a non-spherical core or still contain solid cross-linked material in the core region. When crosslinking is too slow, the ATPS morphology can shift significantly as crosslinking occurs. This can lead to formation of Janus shaped particles or cause significant variation in shape between multiple particles. Normal crosslinking speed allows enough time for phase separation to occur and will crosslink rapidly enough such that ATPS morphology does not shift significantly (i.e., go from hollow shell configuration to Janus configuration).

Soon after droplet formation, the reagents within the droplets are given a period of time to phase separate before fully solidifying the pre-polymer materials. Generally, the pre-polymer contains chemically reactive groups (PO-EGMA or PEG with maleimide, vinyl sulfone, norbornene, epoxide, thiols, etc.) that are biocompatible with the particular cell type(s) to be encapsulated and are reactive with a biocompatible crosslinker (DTT, di-thiol linkers, peptide linkers, bio-orthogonal linkers, cystamine) that can be cleaved/degraded via a biocompatible mechanism (addition of an enzyme or reagent, light, thermal cooling or heating) or mechanically disrupted. Example mechanisms are shown in FIGS. 8A-8B.

pH Dependent Crosslinking pH dependent crosslinking can be used to enhance biocompatibility of the system because other crosslinking methods such as UV-based, radical-based, or chemically based may damage the cells 100 during encapsulation as described further herein. The pH that allows for the polymerization of the hydrogel shell 12 can be adjusted such that the encapsulated cells 100 experience little to no negative effect. For example, crosslinking for the encapsulation of mammalian cells 100 can be adjusted to be within a pH range between 6 and 8, a range that is reasonably compatible for mammalian cell systems. Crosslinking for the encapsulation of microalgae such as *Euglena* and *Chlorella* can be done in broader pH ranges (5-9) since these cell lines are more resistant to extreme pH conditions. It was demonstrated that encapsulating *Euglena* at a pH of 6.5 retains cell viability and that those cells can grow within the particle over time (FIG. 9A). Lipids within these algae can also be labeled by adding a fluorescent stain (e.g., BODIPY) that can diffuse through the particle matrix and reach the enclosed cells 100 (FIG. 9B).

In one embodiment, reagents are mixed at a location immediately prior to droplet generation in the microfluidic droplet generator 200 (i.e., on-chip) at a pH that allows for the reaction between the reactive group of the pre-polymer and the reactive group of the crosslinker (maleimide with thiol at pH<7, maleimide with amine at pH>7.5, vinyl sulfone with thiol at pH<7). Of important note, the pH must be adjusted such that crosslinking does not occur too quickly, causing the formation of a solid particle independent of the reagent concentrations (FIGS. 10A-10B). Also, the pH must be adjusted such that crosslinking does not occur too slowly. Crosslinking increases the molecular weight of the pre-polymer, thereby shifting the binodal curve in a way that a pre-set concentration point will enter the full separation region over time resulting in Janus particles (FIG. 10B). Therefore, the pre-polymer must solidify and become stable quickly following phase separation and while the second non-polymerizable component of the ATPS is still centered within the droplet and fully enclosed. Solidification occurs while the reagents, pre-polymers, and cells are still retained within water-in-oil droplet emulsions.

In one exemplary embodiment, to obtain an ideal hollow shell particle 10 shape, the crosslinking time was adjusted by modulating the pH of the formed droplet in the microfluidic droplet generator 200. It was found that repeatable, uniform hollow shell particles 10 could be formed by generating emulsions with in-droplet concentrations of 5% (w/w) 10 kDa 4-arm PEG maleimide (PEG-MAL) crosslinked with dithiothreitol (DTT) and phase separated using 11% (w/w) 10 kDa dextran (FIG. 26). All reagents were dissolved at a pH of 6.25. With this combination of reagents, uniform hollow shell particles 10 could be formed with an outer diameter of 91 μm and shell thickness of 13 μm (CV of 1.7% and 6.9% respectively) at a particle generation rate of 720 particles/s.

Figure 15:
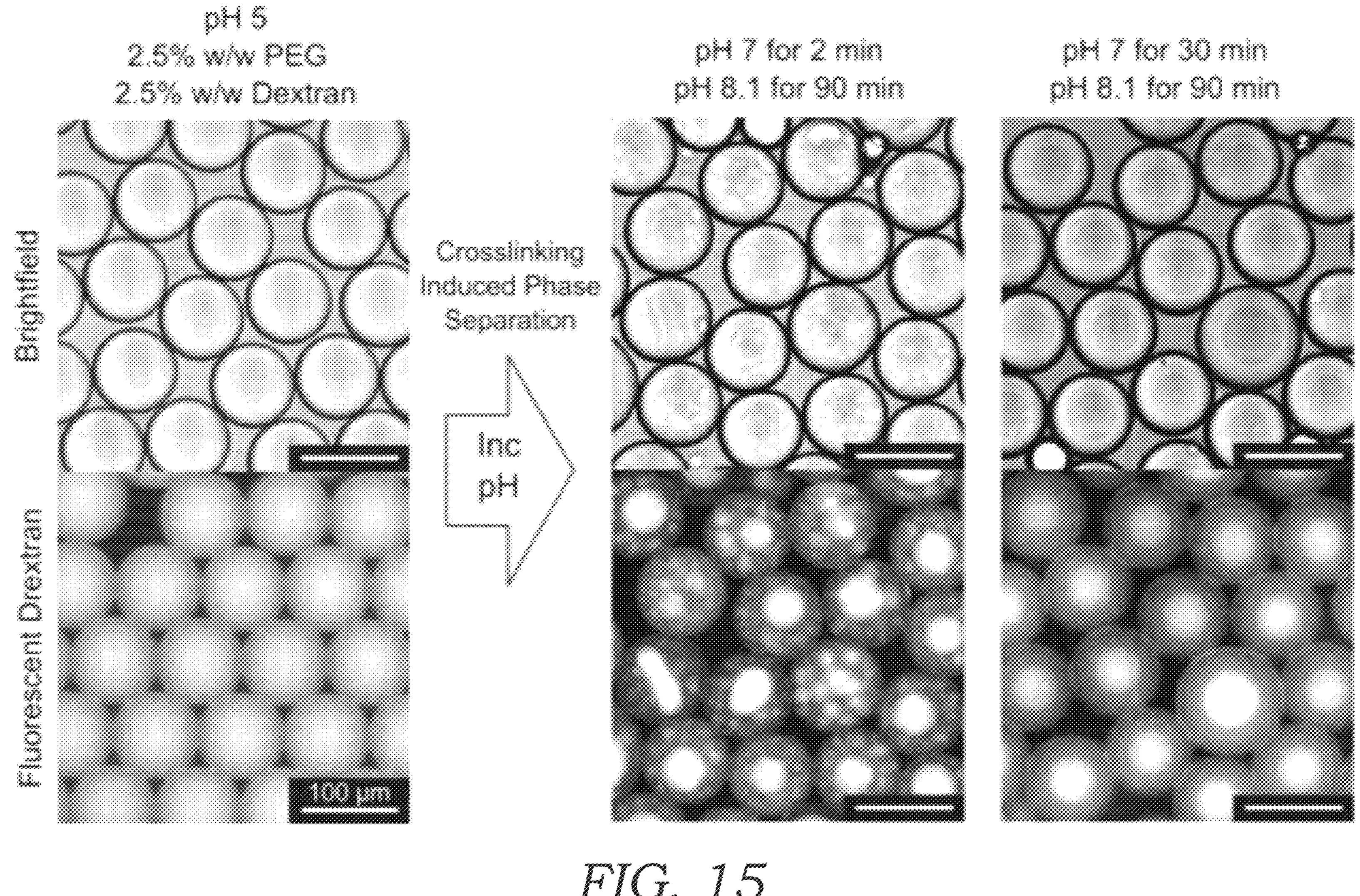
FIG. 15 illustrates crosslinking induced phase separation for formation of hollow shell particles. Here droplets are formed from a precursor solution of 2.5% w/w 8-arm PEG vinyl sulfone (20 kDa), 2.5% w/w dextran (40 kDa), 0.2% w/w FITC dextran (40 kDa), and 8 mM dithiothreitol in 0.3 M triethanolamine buffer (pH 5) using a high-throughput step emulsification device. At this polymer concentration minimal phase separation is observed as shown by both brightfield and fluorescent imaging (left). After generating droplets, Novec™+1% triethylamine is added to the droplet suspension at volume equal to the aqueous phase component (e.g., 100 μL for droplets formed from 100 μL of precursor solution) to increase the pH to 7 to initiate crosslinking via deprotonation of the thiol groups on dithiothreitol. During initial crosslinking, the molecular weight of the PEG molecules increases, inducing phase separation. Additional Novec™+2% triethylamine is added at equal volume to increase the pH to 8.1 to accelerate crosslinking and preserve the resulting particle morphology. In the example shown it was found that shorter incubation times at pH 7 (e.g., 2 min) resulted in incomplete phase separation (middle), while longer incubation times at pH 7 (30 min)

In a parallel embodiment, reagents are first mixed before droplet generation at a pH where the reactive groups of the pre-polymer and the reactive group of the crosslinker do not react. The reagents within the droplets are allowed to phase separate before a biocompatible oil-soluble reagent (e.g., triethylamine, TEMED) is added to the water-in-oil emulsions that changes the overall pH to a range that induces solidification. An example of this is shown in FIG. 15.

Light-Based Crosslinking

In another embodiment, solidification is induced via exposure to light. In one example, the reagents within the droplet are functionalized 4-arm/8-arm/multi-arm PEG (with norbornene, methacrylate, acrylate, acrylamide), dextran, crosslinker (DTT, di-thiol linkers), and a photoinitiator (lithium phenyl-2,4,6-trimethylbenzoylphosphinate, Irgacure, Eosin Y). Solidification is initiated by photopolymerization upon exposure to light (UV, visible, infrared) following phase separation in the droplets. Light-based crosslinking can also solve a problem that may exist in pH-based crosslinking where there is a tendency of crosslinked material to stick to the walls of the droplet generator 200 near the droplet generation region.

Use of UV-induced crosslinking mechanisms can solve this problem since gelation would occur downstream of droplet generation unlike pH-induced mechanisms where mixing of reagents immediately prior to droplet generation often results in gelled material forming in the droplet-generation junction over time that disrupts the overall flow. However, use of UV-induced crosslinking may not be preferred for particular cellular applications as the chemistry and high energy light may damage the encapsulated cells 100 or alter the genome of the cells 100 in an un-desired way. At the same time, UV-induced crosslinking may be used for workflows involving resilient cell types (e.g., bacteria, yeast) or workflows where cells are mutagenized prior to selection, and UV-induced mutations would be potentially beneficial. In another approach, the droplet generator 200 can be made from a material that reduces the amount of gelled material that sticks to the device walls.

Radical scavengers and/or antioxidants may be added to mitigate potential cell damage that may occur with radical-dependent polymerization. Such radical-interactive chemicals can be added at particular concentrations to the non-polymerizable and polymerizable components during particle fabrication that reduce the total number of radicals within the particles to levels that do not significantly damage cells. These radical-interactive chemicals can also be spatially located such that there is a reduction and/or elimination of radicals near the cells but a higher amount within or near regions of radical-dependent polymerization. For example, such radical interactive chemicals can be placed in the non-polymerizable components (e.g., dextran or gelatin phase) that contain cells 100 and are not significantly present in the polymerizable phase (e.g., PEG) that does not contain cells 100. Examples of radical scavengers include tocopherol and naringenin. Examples of antioxidants include ascorbic acid (Vitamin C), glutathione, lipoic acid, uric acid, carotenes, α-tocopherol (Vitamin E), and ubiquinol (coenzyme Q).

Dependence of Hollow Shell Particle Formation on Device Geometry

Figure 13B:
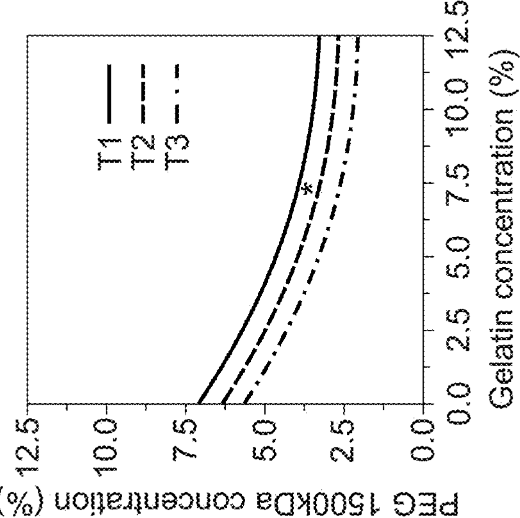
FIG. 13B illustrates how a decrease in the temperature shifts the location of the binodal curves when forming a droplet comprising PEG 1500 Da and gelatin. A droplet, whose chemical composition is denoted by ★, is homogeneous at T1, but as temperature decreases to T2 the droplet is partitioned into two distinct phases where one phase is completely enclosed by another. A further decrease in temperature (T3) increases the degree of separation of the droplet, leading to the droplet with both phases open to the surrounding oil phase.

Formation of hollow shell particles 10 can be improved by optimizing the channel height outlet region of the device where crosslinking is initiated. It was found that having a channel that is close to the droplet size increases the fraction of particles that had fully enclosed cavities. In some embodiments this can be exploited to create hollow shell particles 10 with polymer concentrations far above the binodal curve which would normally form particles with exposed cavities. An example embodiment is depicted in FIGS. 13A-13B. Here, 50-55 micron droplets composed of 13.15% w/w 4-arm PEG norbornene (10 ka), 1.5% Lithium phenyl-2,4,6-trimethylbenzoylphosphinate, 5% w/w 40 kDa Dextran, and 0.325% w/w dithiothreitol in PBS were confined in two separate microfluidic channels. In the device with channel height close to the droplet size (54 microns) it was noted that the dextran phase stayed centered in the droplet when flowing down the channel. In the device with a significantly larger channel (128 microns) it was noted that the dextran phase localizes to the edge of the droplet. See FIG. 17. After crosslinking with UV light (150 mW/cm$^2$) in the outlet region of the channels and washing, the particles extracted from the 54-micron channels had mostly fully enclosed cavities (as revealed by dextran pellets localized in the cores when suspended in ethanol). For the particles fabricated in the larger channel device, nearly all the particles had a cavity exposed to the outside of the particle.

Phase Transfer

After a period of time to allow hollow shell particles 10 to solidify, particles are de-emulsified and removed from oil. In one embodiment, oil is removed via the addition of biocompatible de-emulsifying reagents (perfluoro-octanol, PicoBreak) to the water-in-oil emulsions containing polymerized hollow cell particles 10 that are designed to remove surfactants that are stabilizing the droplet emulsions, a process that destabilizes the emulsions. These de-emulsifying reagents do not inhibit microalgae or other cell 100 viability or growth. Following de-emulsification, hollow shell particles 10 are transferred into a new aqueous solution (PBS, native media). In another embodiment, oil (hydrocarbon, mineral oil, silicon oil) is removed by adding media on top of the droplet layer and centrifuging to mechanically separate the oil from the particles. In a separate embodiment, oil is removed by running the emulsions through a cell strainer. The cell strainer hole size can be chosen to be smaller than the desired average diameter size of the hollow shell particles 10, forcing the hollow shell particles 10 to be captured or blocked by the cell strainer and allowing for oil/surfactant to be washed away via gravity or flow of aqueous solution (media, PBS, solution containing Pluronic™)

Leakage of Non-Polymerized Material Following Phase Transfer

An important feature of the system is that any unsolidified/unbound components (e.g., inert polymer) used in the ATPS mechanism (e.g., dextran) is capable of leaking out of or exiting the hollow shell particles 10 after they are transferred into aqueous solution, creating a completely hollow shell filled with suspending media. Any remaining material within the cavity 14 may have undesired effects on the cells' phenotypic properties (chemical or viscous effects), therefore negatively impacting the assay. To allow for leakage, both the pore size in the polymerized pre-polymer component and molecular weight of the second inert component of the ATPS can be optimized such that the second inert component of the ATPS can diffuse through the solid matrix of the polymerized pre-polymer component and be washed away. It has been demonstrated that 10 kDa dextran can leak through a hollow shell matrix composed of 20 kDa 4-arm PEG that is roughly 20% (w/w) (FIGS. 12A-12D). To allow larger molecular weight dextran to leak through the matrix, the pore size of the solid matrix can be increased. Methods to increase the pore size are discussed herein.

Cytocompatibility of Reagents and Process

A critical feature of the system is that it uses methods that can maintain cell viability throughout the process. Hollow shell particles 10 are made using microfluidic droplet technology, a method that has been well developed for the encapsulation and analysis of cells 100. In particular, microfluidic droplet generator 200 devices are generally fabricated using polydimethylsiloxane (PDMS) that is bioinert and is gas permeable. Oils (fluorinated oil, silicon oil, mineral oil, hydrocarbons) and surfactants (Pico-Surf™, Span80) commonly used for emulsification have been consistently shown to not significantly damage cells 100. In particular, fluorinated oils can dissolve oxygen and small molecules that are important to maintain cell viability during encapsulation. Additionally, the shear stresses exerted on the cells 100 during droplet encapsulation have shown to not significantly damage cells.

Figures 12A, 12B, 12C, 12D:
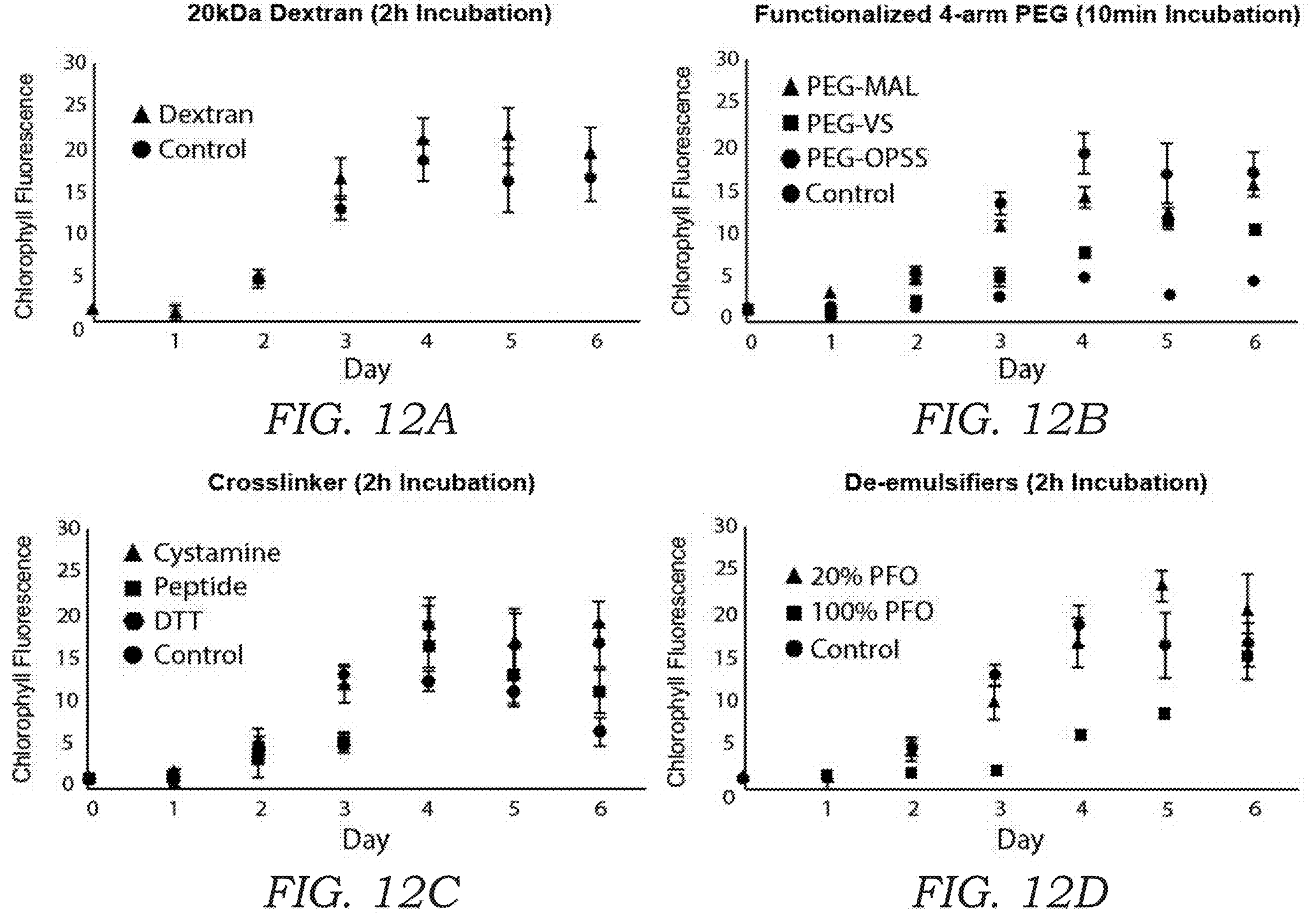
FIGS. 12A-12D illustrate cell compatibility with different reagents for biocompatible hollow shell particle fabrication. Compatibility was characterized by mixing *Chlorella* with the indicated reagent for the specified incubation time, re-suspending the cells in their native media, placing cells in well plates, and characterizing their growth by measuring the chlorophyll autofluorescence via a well plate reader daily for 7 days. The incubation time with the indicated reagent was chosen based on the rough estimate for how long each reagent interacts with cells during particle formation or de-emulsification respectively. Control samples in each plot were incubated for 2 h with standard *Chlorella* media. All indicated polymers and crosslinking agents were dissolved in marine *Chlorella* media at a pH of 6.5.

Various chemicals and chemistries for ATPS, solidification/polymerization, phase transfer, and cell release that maintain cell viability may be used. In particular, it has been demonstrated that dextran used at concentrations for ATPS formation does not inhibit growth of microalgae, yeast, or CHO cells or cause cell death after incubation (FIG. 12A). However, pre-polymer components and cross-linkers may affect cell function. In particular, multi-arm PEG containing orthopyridyl disulfide (OPSS) has been shown to kill microalgae after a short incubation time (FIG. 12B). However, multi-arm PEG containing maleimide and vinyl sulfone groups do not affect microalgae growth or cause cell death following incubation (FIG. 12B). In addition, it was found that by using peptides and cystamine for crosslinking this does not adversely affect *Chlorella* growth post-incubation; however, dithiothreitol has a slight negative effect on *Chlorella* and may induce some cell damage (FIG. 12C). The concentrations of reagents used to degrade the hollow shell particles 10 (trypsin, TCEP) can also be tuned to limit cell damage (FIG. 12D).

De-emulsification agents (perfluorooctanol and Pico-Break) are shown to have little to no effect on microalgae growth with short exposure times (<30 min) and at low concentrations (<20% v/v). However, higher concentrations (>80%) of the de-emulsifying agents at long incubation times (>4 h) are shown to induce some cell damage (FIG. 12D). So, low concentrations of these reagents are used for short incubation times.

The reagents that the pre-polymers and other chemicals are dissolved in have a large effect on cell viability. For example, encapsulating *Chlamydomonas* into hollow shell particles 10 using polymers dissolved in PBS (rather than their native media) results in a lack of cell growth after the hollow shell particles 10 are phase transferred, even if they are transferred back into their native media. The system is uniquely designed such that the pre-polymers can be dissolved in almost any media type (DMEM base, TAP media, yeast broth, marine media, KH media) so that one can choose the aqueous solution that will result in the highest cytocompatibility for the desired encapsulated cells 100 (excluding any effects that the media has on solidification/crosslinking).

Example—Particle Formation

Device Fabrication

In one exemplary embodiment, a microfluidic droplet generator 200 device containing 4 inlet channels with a height of 70 μm can be used to generate uniform droplets. Master molds are fabricated on silicon wafers using a two-layer photolithography process. The first and second layers define the inlet channel and flow focusing junction height and the outlet channel height, respectively. For example, a device with inlet height of 70 microns and outlet height of 130 microns would be fabricated as follows. Spin coat KMPR1050 at a rate of 1800 RPM for 30 seconds and soft bake for 20 minutes at 100° C. Expose the first layer using either a chrome or transparency mask on a mask aligner (e.g., Karl Suss MA6). Expose for 47.5 seconds at 12 mW and follow with a 4-minute post exposure bake at 100° C. Spin coat KMPR1050 directly on top of the first layer at 2500 RPM for 30 seconds and then soft bake for 30 minutes at 100° C. Using the mask aligner align the second mask layer to the first layer using alignment marks and then expose for 95.3 seconds at 12 mW. Follow this with a 5-minute post exposure bake at 100° C. Remove any unexposed photoresist by developing with SU8 Developer for approximately 10 minutes followed by ~1-minute Isopropanol wash and then dry with Nitrogen gas. Molds with different channel heights can be fabricated by adjusting the photoresist types (e.g., KMPR 1005, KMPR 1010) and the spins speeds following general parameters given in the photoresist data sheets.

PDMS devices can be molded from the master molds using poly(dimethyl)siloxane (PDMS) Sylgard 184 kit (Dow Corning). In one example the base and crosslinker were mixed at a 10:1 mass ratio, poured over the mold, degassed, and cured at 65° C. overnight. The PDMS devices and glass microscope slides (VWR) were then activated via air plasma for 30-90 seconds (Plasma Cleaner, Harrick Plasma) and bonded together by placing in contact. The devices are then placed back in the oven for at least 30 minutes. For use with fluorinated oils the channel surfaces are modified to be fluorophilic to achieve proper droplet formation. In one approach the bonded devices were treated with Aquapel™ for 1 min by injecting with a glass syringe and then rinsed with filtered Novec™ 7500 oil (3M). In another approach a solution of Novec™ 7500 oil+1-5% Trichloro(1H,1H,2H,2H-perfluorooctyl)silane is injected into the devices 200 using a syringe. The solution is left to sit for 1-5 minutes and then removed with air and flushed with filtered Novec™ 7500 oil (3M). In both approaches the devices 200 are placed back in the oven at 70° C. for at least 30 min to evaporate residual oil in the channels.

Particle Formation in Droplet Generator

For this embodiment, a detailed example is provided of how to form stable disulfide-linked hollow shell particles 10 in PBS, encapsulate *S. cerevisiae* cells 100, allow enclosed *S. cerevisiae* cells 100 to grow over an incubation time, and release the cells 100 with the addition of TCEP.

Before starting the particle-formation process, the ATPS binodal curve is first obtained for the precursor materials which comprise 20 kDa 4-arm PEG-Ortho-Pyridyldisulfide (OPSS) and 10 kDa dextran dissolved in PBS (FIGS. 6A-6D). Methods for collecting the binodal curve are previously described. Using this curve, hollow shell particles 10 are formed with a final 4-arm PEG maleimide concentration of 3.25% w/w and a final dextran concentration of 10% w/w in PBS at a pH of 6.5. It was found that having a dextran/PEG ratio between 2:1 and 4:1 gives results in an appropriate shell thickness and cavity size for most cell applications.

Before droplet-generation, 13% w/w and 20% w/w 20 kDa 4-arm PEG OPSS and 10 kDa dextran were prepared in PBS at a pH of 6.25, respectively. These concentrations become lowered to desired concentrations (3.25% w/w PEG and 10% w/w dextran, respectively) after they are diluted during mixing and droplet formation. In addition, 2.29 mg/mL DTT in PBS was prepared at a pH of 6.5. This concentration was chosen such that the thiols on the DTT react with 80% of the maleimide groups on PEG maleimide. 0.5% Pico-Surf™ in Novec™ 7500 was prepared that is used as the oil phase for droplet formation. These solutions are placed into separate syringes and attached to separate inlets of a 3-inlet microfluidic droplet generator 200 with a 70 μm channel height at the point of droplet formation. Downstream of droplet generation, the channel height increases to 130 μm. The channel height is chosen to create a droplet size of ~70 μm at the later discussed flow rates. Droplet size can be increased by increasing the device channel height and/or increasing the oil-to-aqueous phase flow rate. Droplet size can be decreased by decreasing the device channel height and/or decreasing the oil-to-aqueous phase flow rate. *S. cerevisiae* cells 100 were placed in the dextran solution at a concentration of 500,000 cells/mL, intended to result in most cell-laden particles having 1 cell/particle. This concentration can be adjusted to create different distributions of the number of cells per particle, generally following Poisson loading statistics.

To form the hollow shell particles 10, the reagents are injected into the microfluidic droplet generator 200 at an oil:PEG:dextran:DTT ratio of 15:1:2:1 (30 μL/min, 2 μL/min, 4 μL/min, 2 μL/min) using a syringe pump (Harvard Apparatus). The oil flow rates can range from about 10-100 μL/min to obtain different droplet/particle sizes. Typically, the dextran phase is used as the middle aqueous phase and the PEG and crosslinker are injected on the outer channels. This arrangement was found to reduce pre-mature crosslinking, and channel clogging. For some embodiments it is possible to include the crosslinker in the dextran phase, in this case both the PEG and dextran phases would be chosen as the outer phase. Phase separation and crosslinking occur simultaneously in the channel. Droplets flow along this region and after ~1-3 minutes will exit the microfluidic droplet generator 200 via outlet tubing and are collected in a conical tube and incubated to allow crosslinking. Crosslinking is slow enough such that phase separation can occur but fast enough such that the change in the molecular weight properties of the PEG doesn't result in the formation of Janus shaped particles. Crosslinking of the hollow shell particles 10 is allowed to occur at room temperature for a 30 min period. This crosslinking time can be increased/decreased based on the pH and the particular chemistry being used. Final droplet size is 66 μm in diameter with 0-10% CV.

Transfer of Particles from Oil to Aqueous Solution and Example Assay

Following crosslinking, the oil and surfactant is removed by adding 20% PFO on top of the droplet layer and transferring the remaining hollow shell particles 10 into yeast broth. Any un-encapsulated cells 100, remaining oil, and/or outlier small particles are removed by running the particle-containing solution through a cell strainer or other filter with a mesh size small enough to capture particles that were larger than a desired size threshold but allow smaller materials to flow through (e.g., mesh size of 40 μm for this example). Hollow shell particles 10 are then transferred into their cell's native media, into a shaking flask, and in 30° C. for *S. cerevisiae* cell 100 growth. Hollow shell particles 10 that have been de-emulsified and suspended in yeast broth have an average size of 103 μm (CV of 3.2%) and an inner cavity size of 89 μm (CV of 2.4%). The overall hollow shell particle 10 size increased from 66 μm to 103 μm when transferred from oil to aqueous solution due to natural swelling of PEG in aqueous solution.

The cell-laden hollow shell particles 10 are allowed to incubate in solution for 5 days, allowing the enclosed *S. cerevisiae* cells 100 to accumulate biomass. The *S. cerevisiae* cells 100 are then released by adding 0.1-100 mM TCEP to particles that break down the di-sulfide linkages structurally holding the hollow shell particles 10 together to release cells 100.

High-Throughput Generation of Hollow Shell Particles

There are many industries that need to understand the activity of cells 100 at the single cells level or benefit from populations derived from a single clone. One of the common challenges faced in the clinical and industrial translation of single-cell analysis is poor scalability. Previously, a parallelized step emulsification device enabled scalable high-throughput generation of monodisperse homogeneous spherical particles. See, e.g., International Patent Application No. PCT/US2021/029167, which is incorporated by reference herein. However, since the step-emulsification device 250 is compatible with a homogeneous solution, hollow shell particles 10 which comprise two distinct phases have not been generated using the device. By starting with two or more reagents which are initially miscible but become immiscible and partition into two phases upon a certain stimulus, hollow shell particles 10 can be produced in a high-throughput manner (FIG. 13A).

High-throughput generation of hollow shell particles 10 can be divided into three steps: 1) high-throughput homogeneous droplet generation with pre-polymer, inert material, crosslinker, and optional cells 100, 2) induced phase-separation of the droplets, and 3) polymerization of the pre-polymer to form hollow shell particles 10.

First, a homogeneous solution consisting of pre-polymer, inert material, and crosslinker is mixed with cells 100 and is injected into an inlet channels 252 of a parallelized step-emulsifier device 250 as illustrated in FIG. 13A. The solution is flowed among hundreds of identical channels 254 (oriented transverse to long axis of channels in FIG. 13A) and intersected by a taller reservoir channel 254 containing an oil, which enables the formation of monodisperse droplets at high rates.

The phase-separation of droplets can be induced through a change in temperature, pH, composition of the droplets or a combination thereof. In a preferred embodiment, droplets contain precursor materials that have temperature-sensitive miscibility and are homogeneous under initial condition but create two distinct phases due to a change in temperature. For example, as described in FIG. 13B, a decrease in the temperature of the system shifts the location of the binodal curves when forming a droplet comprising 7.5 w/w % PEG 1500 kDa and 15 w/w % gelatin. In this particular example, PEG serves as a pre-polymer material that localizes in the outer radius of the droplet and gelatin serves as a gellable inert material that localizes in the center core of the droplet. Gelatin can gel at temperatures lower than 30° C., increasing the effective molecular weight of the material and shifting the binodal curve. Therefore, depending on the position of the droplet relative to the binodal curve, the change in temperature can lead to the droplet with two distinct phases where one phase is completely enclosed by another. By using different concentrations of pre-polymer and inert material, one can obtain different particle morphologies such as hollow shell particles 10, solid spherical particles, or Janus particles. In addition to the PEG/gelatin combination, the change in temperature can induce phase-separation when pre-polymers or inert materials possess a temperature dependent gelation mechanism (e.g., gelatin, agarose, collagen, etc.) Example pre-polymer/inert material combinations include PEG/Dextran, PEG/Agarose, Gelatin/Dextran, PNIPAM/Alginate, PNIPAM/PAAM, Pluronic/Dextran.

In other embodiments, phase-separation occurs due to the changes of pH within the droplets that affect the electric charges of the pre-polymer or inert material. Phase separation in droplets occurs when enthalpic advantages from phase-separation can compensate for entropic loss due to the localizations of droplet components into different phases. Therefore, when pre-polymers or inert materials in droplets are charged species, the phase separation is less favorable as compared to the neutral species because the localization of charged species requires higher entropic costs. The effect that electrostatic properties have on phase-separation can benefit the high-throughput particle fabrication since one can control phase separation of droplets by changing pH which affects charge properties of materials. In one exemplary embodiment, droplets containing homogeneous aqueous solution of 7.5 w/w PEG 1500 Da as pre-polymer, 15% w/w fish gelatin with isoelectric point 6 as inert material and cells 100, are emulsified in Novec™ 7500 fluorinated oil with 0.5% v/v Pico-Surf™ surfactant in pH 4.5. After fabrication of droplets, the pH of droplet is adjusted to pH 6-7 by adding organic bases such as triethylamine (TEA) through the dispersion media. Phase-separation due to a pH change can be achieved with other systems in which one or more of precursor materials are polyelectrolytes whose miscibility is highly dependent on pH. Other example precursor material combinations include Gelatin/Dextran, Gelatin/PEG, Dextran/PEG and Agarose/PEG.

Figures 14A, 14B, 14C:
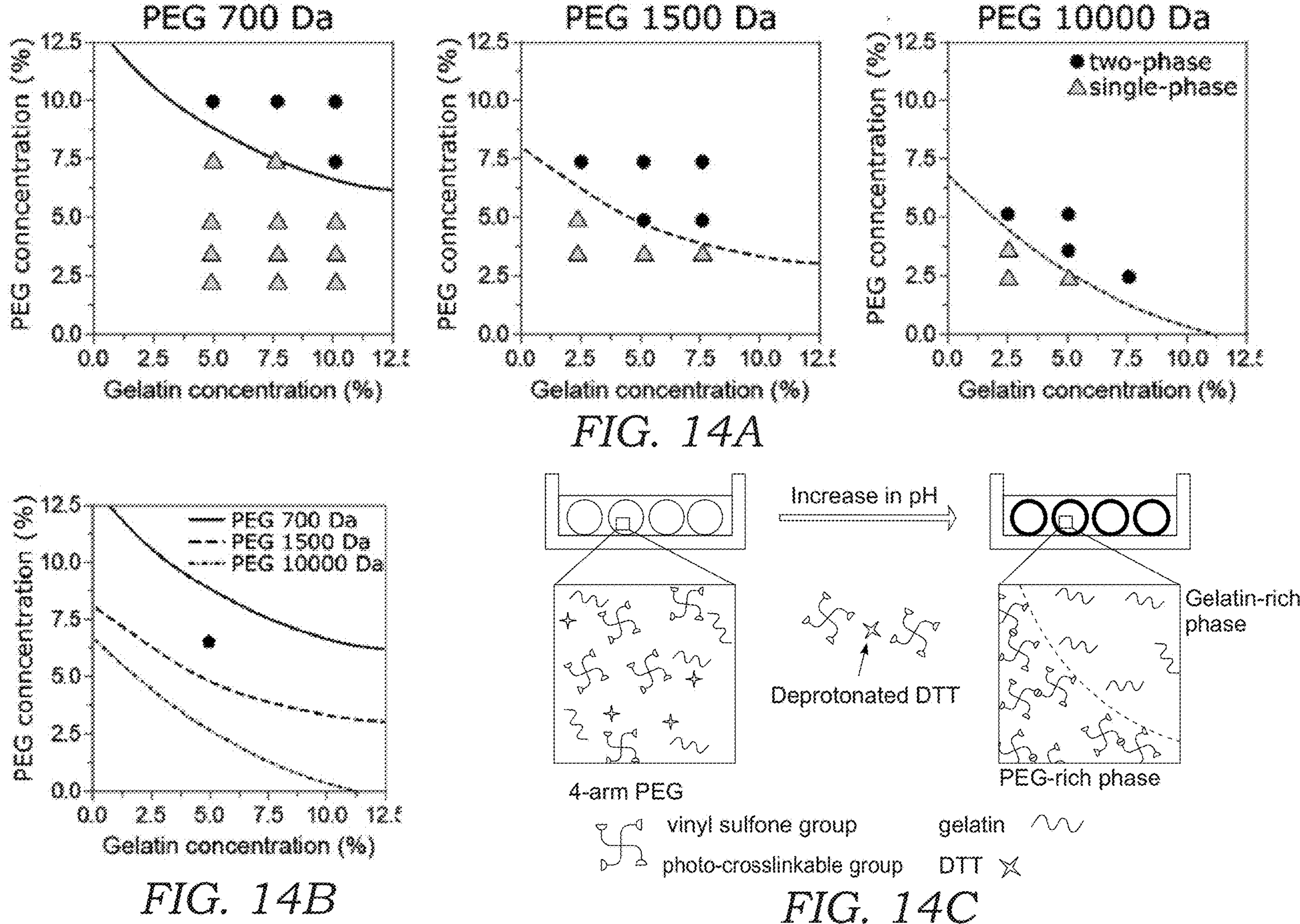
FIGS. 14A-14C illustrate how phase separation between gelatin and PEG is triggered by increase in molecular weight of PEG.

In another embodiment, the phase separation within droplets is triggered by increasing the apparent molecular weight (MW) of the pre-polymer component in droplets. Phase separation of polymer-polymer ATPS systems as well as polymer-salt ATPS systems is sensitive to the molecular weight of the polymers. Polymerization, initiated through a number of approaches such as a temperature change, pH change in the dispersion media, or photoactivation of radical initiators from exposure to light can lead to a change in molecular weight of one or more precursor materials that leads to phase separation as the binodal shifts. An example embodiment of this is shown in FIGS. 14A-14B which describes phase-separation of PEG (pre-polymer) with different MWs and gelatin (inert material), the pre-polymers with higher MWs have stronger tendencies to be separated from inert material, leading to phase-separation at lower concentrated solution. Partial polymerization to increase the MW of the pre-polymer components (e.g., FIG. 14C) in droplets shifts the binodal curve for a pre-polymer and inert material and, as a result, induces phase-separation within the droplets. The polymerization reaction used to trigger phase separation should be sufficiently slow in order to be separate or orthogonal from the polymerization reaction used to fully polymerize the pre-polymer. For example, 5 w/w % gelatin and 7 w/w % 4-arm PEG 700 Da that has a pH-dependent cross-linking group (vinyl sulfone group with DTT as cross-linker) and photo-crosslinkable group are used to generate droplets in pH 6. Once droplets are formed, the pH is increased to >8 in order to initiate the reaction between vinyl sulfone groups and deprotonated DTTs to increase the MW of PEG (FIGS. 14(*b*), 14(*c*)). The partially polymerized PEG which has MW~1500 Da and gelatin are immiscible at the composition, which leads to phase-separation. The photo-crosslinkable groups left unreacted can be used to form a polymer matrix by exposure to light in the following steps.

Another example embodiment is shown in FIG. 15 for a PEG dextran ATPS system. Here droplets are formed from a precursor solution of 2.5% w/w 8-arm PEG vinyl sulfone (20 kDa), 2.5% w/w dextran (40 kDa), 0.2% w/w FITC dextran (40 kDa), and 8 mM dithiothreitol in 0.3 M triethanolamine buffer (pH 5) using a high-throughput step emulsification device 250. After generating droplets, Novec™+ 1% triethylamine is added to the droplet suspension at volume equal to the aqueous phase component (e.g., 100 μL for droplets formed from 100 μL of precursor solution) to increase the pH to 7 initiate crosslinking and induce phase separation. Additional Novec™+2% triethylamine is added at equal volume to increase the pH to 8.1 to accelerate crosslinking and preserve the resulting particle morphology. In the example shown it was found that shorter incubation times at pH 7 (e.g., 2 min) resulted in incomplete phase separation (middle), while longer incubation times at pH 7 (30 min) allowed for more complete phase separation and formation of hollow shell particles 10 (right) as observed.

Polymerization/solidification of the material present in the outer radius of the partitioned droplets can occur via a variety of reaction mechanisms depending on the functional groups present in the reagents. In one embodiment, droplets comprising one or more photopolymerizable materials are crosslinked to form microparticles by exposure to UV, visible light, or other wavelength of light. Photopolymerization generally uses a photoinitiator that has high absorption at a specific wavelength of light to produce radical initiating species. In another embodiment, when the cross-linking kinetics of precursor materials is highly dependent on pH, polymerization of droplets is initiated by a change in pH. For example, an increase in pH deprotonates a thiol and it acts as a nucleophile and donates an electron pair to form a covalent bond with different functional groups including 4-fluorophenyl group, vinyl sulfone group, maleimide group and pyridyl disulfide group.

Importantly this general induced phase separation approach to create hollow shell particles 10 is not limited to step emulsification and can be employed with a variety of droplet generation techniques. Including, but not limited to microfluidic approaches such as flow focusing, T-junction, step emulsification/microchannel emulsification, and other approaches such as membrane emulsification, dispensing processes, spray and electrohydrodynamic spray, vortex mixing. Preferably, the emulsification method creates substantially monodisperse droplets (e.g., with a coefficient of variation in diameter of <10% and more preferably with a coefficient of variation <5%). For certain applications larger variations in diameter can be tolerated (CV>10% and <50%).

Example of High-Throughput Hollow Shell Particle Fabrication

In one embodiment, a parallelized multi-channel step-emulsifier 250 (FIG. 13A) can be used to generate uniform droplets in high-throughput. Master molds are fabricated on silicon wafers using a two-layer photolithography process. The first and second layers define the nozzle channel height and the inlet/outlet reservoir region channel height, respectively. For example, a device with nozzle height of 25 microns and reservoir height of 150 microns would be fabricated as follows. Spin coat KMPR1025 at a rate of 3200 RPM for 30 seconds and soft bake for 12 minutes at 100° C.

Expose the first layer using either a chrome or transparency mask on a mask aligner (e.g., Karl Suss MA6). Expose for 24 seconds at 12 mW and follow with a 2-minute post exposure bake at 100° C. Spin coat KMPR1050 directly on the first layer at 1000 RPM for 30 seconds and then soft bake for 30 minutes at 100° C. Using the mask aligner align the second mask layer to the first layer using alignment marks and then expose for 83 seconds at 12 mW. Then do a 5-minute post exposure bake at 100° C. Remove any unexposed photoresist by developing with SU8 Developer for approximately 10 minutes followed by ~1-minute Isopropanol wash and then dry with Nitrogen gas. Molds with different channel heights can be fabricated by adjusting the photoresist types (e.g., KMPR 1005, KMPR 1010) and the spins speeds following general parameters given in the photoresist data sheets. After fabrication of master molds, PDMS devices are molded from the master molds using poly(dimethyl)siloxane (PDMS) Sylgard 184 kit (Dow Corning) as described herein.

To form the hollow shell particles 10, an aqueous solution composed of 5 w/w % 4 arm PEG-acrylate 5000 Da, 10 w/w % gelatin, 250,000 cells/mL *Chlorella* cells 100 and 2 w/w % lithium phenyl-2,4,6-trimethylbenzoylphosphinate in marine media is prepared. For the oil phase, 0.5% Pico-Surf™ in Novec™ 7500 is prepared. The prepared solutions are loaded into separate syringes and injected into a multi-channel step-emulsifier 250 using syringe pumps (Harvard Apparatus) at oil rate 150 μl/min and aqueous solution rate 75 μl/min. The step-emulsifier 250 with 25 μm channel height and 150 μm reservoir height is used to generate 90 μm droplets (CV<5%). Droplets are collected into a PDMS reservoir and incubated in a 4° C. refrigerator for 1 hour to allow phase separation of PEG and gelatin. After phase separation, the PEG phase was crosslinked with UV light at a power of 10-30 mW/cm$^2$ over an approximate duration of 5 minutes. Crosslinked particles were collected and oil and gelatin were removed using a series of washing steps to create the final hollow shell particles 10. Briefly, excess oil was removed by pipetting and a layer of PBS was added on top of the remaining emulsions. A solution of 20% v/v perfluorooctanol (PFO, Sigma) in Novec™ 7500 was then added to destabilize the emulsions and transfer particles to the PBS phase. Next the hollow shell particle 10 solution is filtered through a cell strainer with mesh size of 40 μm to remove oil. Hollow shell particles 10 are then transferred into marine media and cultured in a shaking incubator under blue light to allow for *Chlorella* cell 100 growth.

Different Incubation Conditions

The ability for the particle's inner cavity to have continuous and free solution exchange with the outer solution is a critical feature of the system and enables incubation conditions for enclosed cells 100 that are not possible with previously developed methods (microwells, droplet technology). Specifically, such conditions allow for cell growth and assays to be performed in more physiologically relevant conditions and makes it possible to perform assays that were not previously possible. In particular, cells 100 do not deplete the nutrients within the compartment because nutrients can be quickly replenished by having the hollow shell particles 10 incubate in a large bulk media or having the bulk solution replaced with new media. Such a process is difficult to achieve with droplet technology and most other microfluidic systems because the cells 100 would need to be de-compartmentalized and re-compartmentalized for the solution to be replenished, a process that is generally not straightforward, leads to loss of a confined clonal population, may require significant labor, and may negatively impact the assay. In addition, the solution exchange allows for cell-cell communication via released factors between enclosed cells 100, cells 100 floating free in the bulk solution, and/or cells 100 enclosed in other hollow shell particles 10, thereby making the conditions more similar to a physiologically or industrially relevant environment, such as a high-density culture. A lack of such an environment during the incubation part of the assay makes it difficult to translate cell behavior within the compartment to behavior in the natural or industrial environment. This is a problem particularly when a user wants to re-culture cells 100 at a large bulk scale following selection at the microscale of specific cells 100 or colonies. Also, active solution exchange makes it easy for a user to change the parameters of the media at any point during the incubation time, allowing for previously un-attempted assays and multi-step assays. Growth and maximum density of *Chlamydomonas reinhardtii* is significantly enhanced when compartmentalized in a hollow shell particle with continuous solution exchange with new media compared to that in an in-oil aqueous emulsion where there is no continuous solution exchange (FIGS. 16A-16B).

Figure 11A:
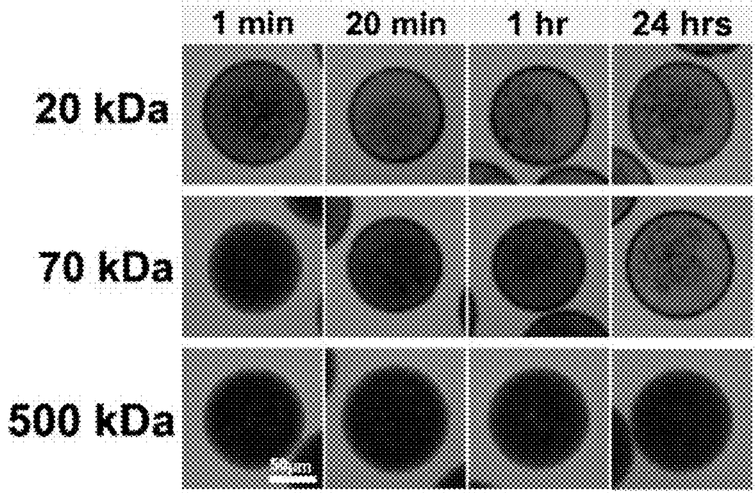
FIG. 11A illustrates the results of a dextran diffusion and leakage study showing that FITC dextran can diffuse through the PEG solid polymer matrix of a hollow shell particle. Hollow shell particles were placed into a solution containing FITC dextran of different molecular weights. 20 kDa FITC dextran almost immediately diffused into the cavity of the particles. 70 kDa FITC dextran took more time to diffuse through and into the cavity of the particles. 500 kDa FITC dextran had very little diffusion into the cavity of the particles even after 24 h, showing a molecular weight cut-off between 70 kDa and 500 kDa for transport across the polymer shell of the hollow shell particle.
Figure 11B:
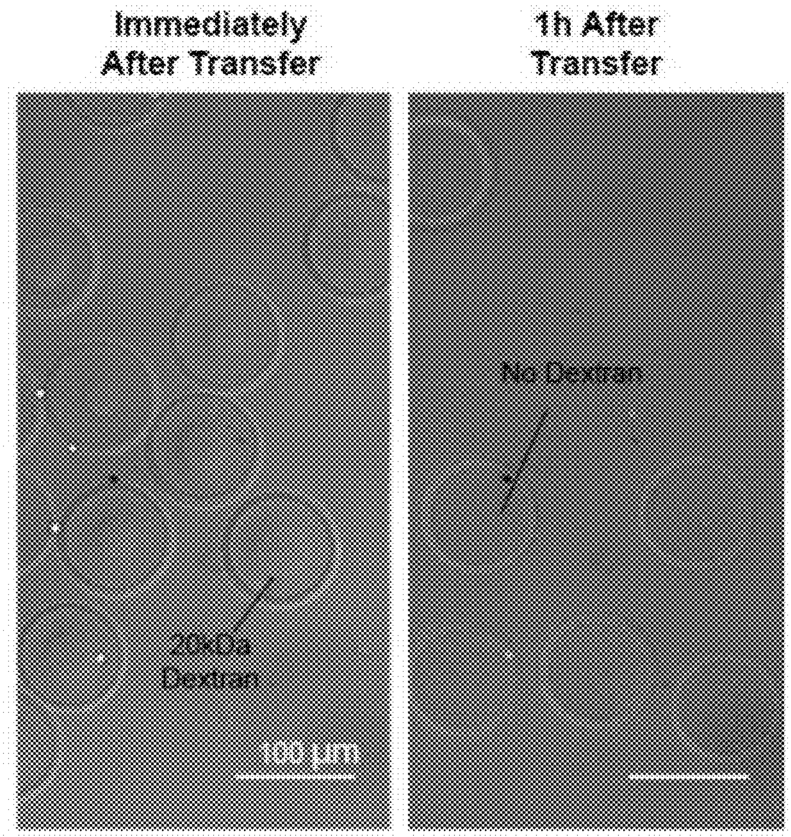
FIG. 11B illustrates images indicating that 20 kDa dextran leaks out of hollow shell particles after hollow shell particles are transferred to solution. Immediately after transfer of hollow shell particles from oil to aqueous solution, the hollow shell particles contain a small amount of visible dextran within the cavity. However, this dextran transports out of the cavity and diffuses away 1 h after transfer of hollow shell particles. The dextran can be visibly distinguished within the hollow shell particle because the PEG phase expands after transfer to aqueous solution.
Figure 11C:
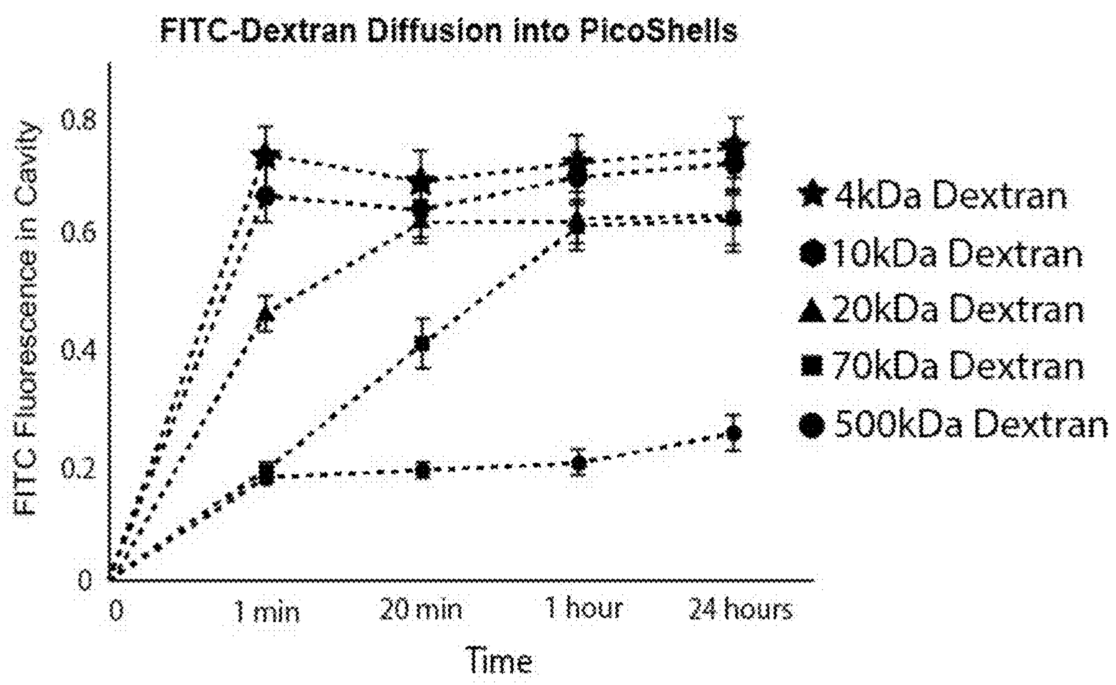
FIG. 11C illustrates a graph of observed FITC fluorescence in the cavity as a function of time for different dextran molecular weights. 500 kDa FITC dextran had very little diffusion into the cavity of the particles even after 24 h while 70 kDa FITC dextran took time to diffuse through and into the cavity showing a molecular weight cut-off between 70 kDa and 500 kDa for transport across the polymer shell of the hollow shell particle.

Enhanced growth was also found with other types of cells 100 in hollow shell particles 10 as compared to droplets. For example, it was found that encapsulated cells 100 (*Chlorella* sp., *Saccharomyces cerevisiae*, and adherent CHO cells 100) grow more rapidly and to higher final densities in the hollow shell particles 10 than in microfluidic droplets in oil (FIGS. 22C, 22D, 22E). Cells 100 were from the same respective culture were encapsulated into hollow shell particles 10 and droplets on the same day. *Chlorella* growth was tracked every 12 h over a 72 h period and *S. cerevisiae* was tracked every 6 h over a 36 h period. Interestingly, it was found that *Chlorella* grow rapidly in hollow shell particles 10 starting with the formation of a first generation of daughter cells following 12 h of incubation but did not grow when encapsulated in microfluidic droplets even over a 72 h period (FIG. 22C). *Chlorella* 100 were encapsulated and incubated in autotrophic media, presumably making cells 100 more susceptible to nutrient and/or gas transport. *Chlorella* 100 were found to double every 12.2 hours and reached a carrying capacity within the 155 pL inner cavity 14 of a hollow shell particle 10 of approximately 250 cells 100 (FIG. 22C). In parallel, it was found that *Saccharomyces cerevisiae* grow both in hollow shell particles 10 and in water-in-oil droplet emulsions (FIG. 22D). However, while the growth rate of the yeast 100 in both types of compartments were not statistically different before the first 18 hours of culture (P=0.28 at 12 h), the growth rate of droplet-encapsulated yeast became significantly slower than hollow shell particle-encapsulated yeast 100 at later times (P<0.001 at times >18 h). The reduction in the growth rate of droplet-encapsulated yeast is likely due to the depletion of essential nutrients and/or accumulation of cytotoxic cellular waste. All nutrients present in both media types were below 200 Da. Such nutrients are freely exchanged through the outer shell 12 of the hollow shell particles 10 given the molecular weights below ~40 kDa (FIGS. 11A-11C). The average number of yeast cells 100 in hollow shell particles 10 is dramatically increased between 24 and 48 hrs after encapsulation to 2900 cells/hollow shell particle 10, ~20× higher than the carrying capacity in droplets (~150 cells/droplet). It was also found that adherent CHO cells 100 can grow within hollow shell particles 10 and not within droplets (FIG. 22E). CHO cells 100 have a reduced growth rate for the first 24 h but after this adjustment period grow with a doubling time of 18 h per doubling starting at 24 h after encapsulation.

CHO cells 100 reach a carrying capacity of ~100 cells/hollow shell particle 10 96 h after encapsulation. The lack of growth of CHO cells 100 in droplets is likely due to the need for adherent cell lines to have a solid surface to attach to in order to elicit proliferation signaling.

Intriguingly, it was also observed that *S. cerevisiae* cells 100 do not stop dividing once they fully occupy the volume of the inner cavity 14 of the hollow shell particle 10 and additional cells 100 actually causes the hollow shell particle 10 to stretch and/or expand, increasing the overall diameter. The diameter of the hollow shell particles 10 can actually expand from an initial diameter of ~90 μm to a maximum size of ~500 μm after 4 days at which point the hollow shell particle 10 ruptures and releases the encapsulated cells 100. This ability for a growing colony to expand the hollow shell particle 10 is advantageous as a growing colony then creates a larger size hollow shell particle 10 which can be separated out using filtration or easily characterize by optical scatter signals for sorting. This phenomenon was not observed for encapsulated *Chlorella* colonies. Instead, the microalgae were observed to stop dividing when the colony reaches the carrying capacity of the hollow shell particle 10.

In one embodiment, cell-containing hollow shell particles 10 are transferred into and incubated in aqueous media for a period of time required for the desired assay. In one application, the hollow shell particles 10 enclose cells 100 (mammalian cells, yeast, microalgae) that are suspended in their native/preferred media (DMEM base with FBS, broth, TAP media, seawater) and are incubated for a desired period of time that allows for the cells 100 to exhibit one or more phenotypic properties (e.g., growth, secretion, accumulation, binding). For example, *Chlorella* cells 100 are encapsulated into hollow shell particles 10, re-suspended into marine media, and allowed to accumulate biomass and lipids over a 2-7 day period. In another example, enclosed hybridoma cells 100 are suspended in DMEM with FBS and Pen-strep and are allowed to secrete antibodies for a 0.5-5 h period. In another application, cell-containing hollow shell particles 10 are re-suspended in aqueous solution that contains desired nutrients (e.g., metals, sugars, salts) or biomaterial (e.g., infectious agents, proteins) additions and/or deficiencies. In one example, *Chlamydomonas reinhardtii* are encapsulated in hollow shell particles 10, suspended in nitrogen deficient TAP media, and are allowed to accumulate biomass and lipid over a 2-7 day period. In another example, yeast cells 100 are encapsulated in hollow shell particles 10, and suspended in leucine deficient media, and are allowed to accumulate biomass to select for yeast colonies competent in producing leucine (e.g., through the introduction of a plasmid encoding genes in the leucine biosynthesis pathway, such as beta-isopropylmalate dehydrogenase).

In one embodiment, the solution contains non-encapsulated cells 100 that can interact with the cells 100 enclosed within the hollow shell particles 10 via released biofactors. The pore size of the solid matrix of the hollow shell particle 10 are tuned such that biofactors (e.g., growth factors, cytokines, antibodies) of interest can diffuse in and out of the interior cavity 14 of the hollow shell particle 10 but initially enclosed cells 100 cannot exit the cavity nor can initially external cells 100 enter into the cavity. In one application, the particle's cavity 14 contains one or more cells 100 prevalent for immunological studies (e.g., B-cells, T-cells, NK cells) and is suspended in a solution containing other cell types (e.g., T-cells, NK cells, B-cells, macrophages, neutrophils, red blood cells, platelets, bacteria). The enclosed and external cells 100 communicate via secretions commonly used in immunological responses (cytokines, inflammatory factors, antibodies). In one example, hollow shell particles 10 contain T-cells 100 and are suspended in a blood plasma solution that contains other white and red blood cells. Secretions from those cells 100 external to the hollow shell particle 10 diffuse through the solid phase and interact with the encapsulated T-cells 100, potentially altering its phenotypic properties (e.g., growth, exhaustion, secretion rate). Parameters of the external solution such as the presence of particular cells 100 or to the nutrient composition can be adjusted to analyze differences in the phenotypic properties of the encapsulated cells 100. In another example, the hollow shell particles 10 contain co-encapsulated NK cells 100 and target cell lines (e.g., cancer cells, infectious agents) and are also suspended in blood plasma containing T-cells 100. Depending on the properties of the external solution or presence of particular T-cells 100 (e.g., differentiated by type, exhaustion point, secretion profile), cytokines from the T-cells 100 may interact with the NK cell 100 and may stimulate the killing of the co-encapsulated target cell line. In another application, the hollow shell particles 10 enclose microalgae lines and are suspended in solution containing other cell types (e.g., other microalgae, protists, bacteria).

In another embodiment, the external solution contains cell types that alter the solution's nutrient composition potentially affecting the enclosed cell's phenotypic properties. In one example, the hollow shell particles 10 enclose microalgae cells 100 (e.g., *Euglena, Chlamydomonas, Chlorella*) and the external solution contains bacteria, protist, or fungal cells lines that deplete the nutrients in the external media (glucose, amino acids, minerals, vitamins). Such depletion may affect the growth or lipid accumulation properties of the enclosed microalgae cells 100.

Solid Polymer Matrix Modifications

Methods of Chemical Modification

The chemical properties of the solid matrix of the hollow shell particles 10 may be altered with the addition of functional groups to the solid phase. Such functional groups include affinity agents (e.g., proteins, antibodies, peptides, aptamers, biotin, streptavidin), cell binding agents (e.g., RGD peptide, fibronectin, positively charged molecules), or chemically reactive groups (e.g., amines, thiols). These functional groups can be added via direct conjugation between the desired functional group and chemically reactive groups within the solid matrix. For example, a peptide sequence containing one or more RGD motifs also contains one or more cysteine (thiol-containing) amino acids that can directly conjugate to maleimide groups within a polymer that forms the solid matrix. Chemical modifications may occur during droplet formation by adding the reactive functional group(s) within one or more of the reagents (dextran, PEG, crosslinker) used for ATPS and droplet formation. Functional groups may also be added after particle solidification and de-emulsification. For example, a hollow shell particle 10 may be functionalized with streptavidin by adding the affinity agent to biotin-coated particles in aqueous solution.

Applications of Chemical Modifications

In one embodiment, the solid phase contains cell binding agents (e.g., peptides, proteins, antibodies, aptamers, charged materials) that enclosed cells 100 can bind to. This allows for adherent cells to attach to the solid substrate within the compartment. For example, the solid matrix of the hollow shell particle 10 may contain peptides with RGD motifs that enclosed cell lines (CHO cells) can attach to. This feature makes the system compatible for adherent cell lines because they will be able to adhere to a solid substrate.

This feature can also be used to bind suspension cells 100 to the solid surface. Charged substances such as poly-L-lysine (PLL) within the solid phase can cause binding of adherent or suspension cell lines. Antibodies specific to particular cell receptors may be useful for selective binding of particular cell lines (e.g., stem cells, adherent CHO cells, or other adherent cell types). In one example, the hollow shell particle 10 encloses multiple cell types but the solid matrix contains a binding motif (e.g., antibody, peptides, or aptamers specific to a surface markers) that allows for binding of only a particular sub-population. In another example, embedded antibodies may stimulate or inhibit particular cell phenotypic properties. In one embodiment, secreting cell lines have their secretions halted before particle encapsulation. Once these cells 100 are placed within the hollow shell particles 10, they can interact with antibodies within the particle that stimulate cell secretions. This feature may reduce the amount of secretion crosstalk that occurs due to secreting cells 100 sifting in bulk solution for a period of time before compartmentalization.

In addition to or in a different embodiment, the solid phase of the hollow shell particle 10 contains agents that can capture biomolecules released from enclosed cells 100. In one example, the affinity agents are composed of antibodies, peptides, proteins, or aptamers that can capture cell secretions before they diffuse through the matrix and into the solution external to the hollow shell particle 10. In one application, cytokine specific antibodies (e.g., anti-IL8, anti-IL2, etc.) are embedded in the hollow shell particle's solid phase that capture desired cytokine secretions from an enclosed T-cell 100. In another application, antibodies secreted from enclosed hybridoma or B-cell lines are captured by antigens present in the solid matrix. In another example, the solid matrix contains nucleotide sequences (e.g., DNA, RNA) that can capture desired released nucleic acids from an encapsulated cell 100. These sequences may serve as primers for nucleic acid amplification processes (e.g., PCR, LAMP) and/or reverse transcription in the case that the released nucleic acids include RNA.

In another embodiment, the solid phase of the hollow shell particle 10 contains chemical modifications that allow the hollow shell particles 10 to bind to each other or to a surface. Allowing the hollow shell particles 10 to bind together may enhance cell-cell communication via released biofactors due to the closer proximity of other cells 100. Features allowing hollow shell particles 10 to bind to a solid surface can be used for applications where there needs to be limited motion of the hollow shell particles 10 or where the user wishes to exchange solutions without any centrifugation steps. Examples of bioconjugation chemistries include maleimide-thiol, thiol-vinyl sulfone, amine-NHS ester, amine-isocyanate, amine-thiocyanate, azide-alkyne, and tyrosine-diazonium salt reactions. Covalent linkage can also be achieved using enzymatic processes such as activated Factor XIII linkage of K and Q peptides. Linkages between hollow shell particles 10 and other particles or another solid surface can include cleavable substrates that allow particles to be released from their bound substrate. Examples of such cleavable substrates include disulfides, enzyme cleavable peptide sequences, light-cleavable substrates, and pH cleavable substrates.

In another embodiment, the hollow shell particles 10 are formed from a material or polymer that incorporate a fluorogenic substrate attached, bound, or otherwise contained in it. There are several suitable fluorogenic scaffolds and substrate types that turn fluorescent through action of an enzyme, e.g., upon cleavage of a peptide from the fluorophore. In the case wherein the fluorogenic substrate is anchored to the material of shell 12, the shell 12 becomes fluorescent during exposure to an active enzyme, i.e., fluorescence of the hollow shell particle 10 indicates the expression and secretion of an active enzyme capable of cleaving the tag off the polymer and thus makes individual cell clone expressing e.g., a desired enzyme selectable. In the case wherein the fluorogenic substrate is contained within the volume of the hollow shell particle 10, the fluorogenic substrate should be attached to large molecular weight molecules to prevent diffusion out of the particle. Upon cleavage of the fluorogenic substrate by an enzyme the volume of the hollow shell particle may become fluorescent. This strategy and this modified shell material could be used to select enzymes for a wide variety of applications, namely for use in e.g., detergents, targeted degradation of arteriosclerotic plaques or other undesired deposits in the body and degradation of toxic contaminants, respectively. U.S. Patent Application Publication No. US20050153306A1, which is incorporated by reference, discloses an example of a usable fluorophore. International Patent Publication No. WO 2005007678, which is also incorporated by reference discloses its synthesis. In this embodiment, a transgene or a library of different mutations of a transgene may be introduced into the cells 100 coding for an enzyme of interest for selection of enzymes with increased or decreased activity or activity in the presence of a specific environment (e.g., high or low pH, high or low temperature, presence of solvents).

In a related embodiment, the cells 100 used in this platform express a diversity generating mechanism like CRISPR or similar that acts on the transgene introduced into the cells 100. This enables the rapid generation and pre-screening of active clones in pooled format libraries that can then be selected for enhanced binding or enzymatic activity of a recombinant product in an arrayed format downstream. An example of a diversity generating technology useful for this purpose is disclosed in Parola, et al., Antibody discovery and engineering by enhanced CRISPR-Cas9 integration of variable gene cassette libraries in mammalian cells, MAbs. 2019 November-December; 11(8): 1367-1380, which is incorporated by reference herein.

Methods of Physical Modifications

It is generally known that the stiffness of the substrate that an adherent cell line is bound to greatly affects the overall cell growth and viability on that substrate. So, in some implementations, is important to control the stiffness of the hollow shell particle 10 for adherent cell applications. The stiffness may be altered using a variety of approaches including, but not limited to adjusting polymer precursor concentration, crosslinker type and or concentration, molecular weight, reaction kinetics, polymer branching properties (e.g., 4-arm vs 8-arm), number of reactive groups per unit polymer length). For example, increasing or decreasing the polymer precursor concentration will typically increase and decrease the matrix stiffness. Low molecular weights or higher degree of branching will increase matrix stiffness. For polymers with many reactive sites (e.g., hyaluronic acid), tuning the relative frequency of reactive sites will affect stiffness. For step-growth hydrogels such as multi-arm PEG-Vinyl sulfone, multi-arm PEG-Norbornene, multi-arm PEG-Maleimide, stiffness is sensitive to the concentration of crosslinkers used (e.g., PEG dithiol, DTT). In general, matching the molarity of reactive groups on the cross-linkers with the polymer precursors will result in more interconnected cross-linking and higher stiffness. Including too little crosslinker can lead to insufficient connections and lower stiffness and including too much crosslinkers can saturate reactive groups on precursors also limiting crosslinking and lowering stiffness. In radical based crosslinking systems stiffness can be adjusted by changing light intensity, light exposure time, photoinitiator concentration, and any combination of the prior. This is particularly the case for polymer systems that have reactive groups that undergo chain growth polymerization (e.g., acrylate, acrylamide, methacrylate, etc.).

The pore size of the solid matrix of the hollow shell particle 10 is an important feature that can be fine-tuned to control the exchange of biomolecules, nutrients, and labels between the particle's inner cavity 14 and the external environment. For example, a pore size that is too small may not allow for fluorescent labels or growth factors to enter the inner cavity 14. In some applications, it may be important for the pore size to be tuned such that certain larger molecules can't enter or exit the cavity 14 but allows for smaller molecules to be actively exchanged. Applications and pore size parameters for certain applications are discussed below.

Pore sizes may be adjusted via a variety of mechanisms. For example, the pore size may be adjusted by the concentration of polymer used to make the solid phase. Higher concentrations of solid polymer generally result in smaller pore sizes and lower concentrations result in larger pore sizes. The pore size may also be adjusted via the molecular weight of the polymer. In the case that the polymer is 4-arm/8-arm/multi-arm PEG, larger molecular weights (and therefore longer arm lengths) generally result in larger pore sizes when polymerized at the same molar concentration as those with smaller molecular weights. Smaller pore sizes can be achieved with polymers of smaller molecular weights. Additionally, the pore size may be increased by including non-reactive material, or more generally material that does not participate in crosslinking during particle solidification, in the PEG phase during particle formation. Examples of such materials that increase the pore size are inert PEG, gelatin, and hyaluronic acid. This method allows one to obtain the desired PEG and dextran concentrations for a particular point on the ATPS binodal curve that gives the desired particle shape and size but allows one to adjust the pore size via the non-reactive/reactive PEG ratio. For example, a ratio of 1:5, 2:5, or 3:5 non-reactive PEG: reactive PEG may be used. A greater proportion of non-reactive PEG relative to the amount of reactive PEG results in larger pore sizes and vice-versa.

Biocompatible Release of Cells

An important feature of the hollow shell particles 10 is that enclosed cells 100 may be released from the hollow shell particles 10 while still maintaining cell viability and function. Specifically, cells 100 are capable of maintaining the majority of their genetic and phenotypic properties for post-analysis and/or further culturing. Cells 100 can be released by the breakdown/cleaving of degradable motifs within the particle's solid phase that results in the destabilization and breakdown of the hollow shell particle 10 or through mechanical rupture of the particle's shell through pressure, shear, stretch and the like. In most cases, the degradable motif (e.g., di-sulfide, peptide sequence) is within the chemically reactive group used to crosslink the solid matrix. In other cases, the degradable motif is not within the crosslinker but rather exists as a group that is incorporated in the pre-polymer that comprises most of the solid matrix (e.g., POEGMA or peptide backbone). In another case, cells 100 are released by physically inducing the opening of the hollow shell particles 10. For example, a shearing stress can be applied to the hollow shell particles 10 in a way that induces the rupture of the hollow shell particles 10. In another example, the colony(s) within the hollow shell particle 10 can grow past the carrying capacity of the particle's inner cavity 14 and causes the outer shell 12 to stretch past its rupture point, causing cells 100 to be released. Selection of an appropriate degradable motif can be non-obvious because it must be biocompatible with the cell line of interest but not be pre-maturely degraded by any factors released by the cell(s) 100 or any supplements within the surrounding solution. For example, hollow shell particles 10 containing matrix metalloproteinase (MMP)-degradable peptide linkers and *Chlamydomonas* was successfully demonstrated. However, the *Chlamydomonas* were able to release themselves from the hollow shell particles 10 after 2-4 days which is prior to a desired time point of 5-7 days, likely due to the release of MMPs or other proteases from the microalgae. To address this, bio-orthogonal linkers (e.g., TEV degradable peptide linker) or di-sulfide linkages were identified that can be incorporated into the particle matrix for long-term (>3 days) studies of *Chlamydomonas*. In another example, di-sulfide linkages cannot be used to structurally hold together the particle's solid phase in applications where the external media contains thiol-containing chemicals. Many cell lines (e.g., mammalian cells 100) require the presence of cysteine in the media for proper cell functioning. Thus, some embodiments may be limited to using other polymer linkers (e.g., peptide linkages for these applications). It is important that the method of cleaving the degradable motif is also biocompatible.

Cleavable Substrate Linkages

In one embodiment, the hollow shell particle 10 contains a degradable motif that is broken down with the addition of a reagent that can cleave a chemical group within the degradable motif. The degradable motif may be a synthetic linker (e.g., di-sulfide linkage) or biomolecular polymer (e.g., peptide sequence, nucleotide sequence, carbohydrate, lipase-degradable substrates). In one example, the solid matrix is structurally held together by di-sulfide degradable motifs that can be cleaved with the addition of thiol-containing reagents (e.g., DTT or TCEP). Particles containing di-sulfide linkages can be made by using di-thiol linkers (e.g., DTT, PEG di-thiol) and multi-arm PEG-OPSS as the crosslinker and solid phase polymer respectively and that these particles can be degraded with addition of 1 mM DTT (FIG. 18A). DTT and TCEP can be added to hollow shell particles 10 at concentrations ranging from 0.1-100 mM. Di-sulfide linked hollow shell particles 10 can be made using cystamine as the crosslinker and PEG-maleimide. In another example, the solid matrix is crosslinked with a peptide linker that incorporates a chosen sequence (GNNQQNY [SEQ ID NO: 3], GPQGIAGQ [SEQ ID NO: 4], IPVSLRSG [SEQ ID NO: 5], QPQGLAK [SEQ ID NO: 6], GPLSLGK [SEQ ID NO: 7], GPLGMHGK [SEQ ID NO: 8], DGPQGIWGQ [SEQ ID NO: 9], ENLYFQG [SEQ ID NO: 10], ENLYFQS [SEQ ID NO: 11] that can be degraded with a desired enzyme (e.g., MMP, TEV protease). This peptide can crosslink the solid matrix by having reactive functional groups within the sequence (e.g., cysteine, lysine) or other functional groups added to the ends or within the sequence (e.g., thiol, amine, maleimide, vinyl-sulfone, biotin). The fabrication of hollow shell particles 10 with MMP-degradable motifs and the breakdown of these hollow shell particles 10 with the addition of 0.05% (w/v) trypsin (FIG. 18B) has been demonstrated. Trypsin and other MMPs or proteases can be added to hollow shell particles 10 at concentrations ranging from 0.001-1% (w/v) to induce degradation of MMP-degradable hollow shell particles 10.

TEV can be used to degrade TEV-degradable peptide sequences at concentrations between 0.1-1,000 units/pt. Biocompatibility and/or bioorthogonality of TCEP, DTT, MMPs, and TEVs have been previously shown within the mentioned reagent concentrations. Other potential proteases that can be used include endoproteinases, Factor Xa Protease, Furin, IdeZ Protease, Proteinase K, Thermolabile Proteinase K, and α-Lytic Protease.

In many situations, the release of biofactors from the enclosed cells 100 that can degrade linkers within the hollow shell particle 10 may negatively affect the intended assay; however, this mechanism can be used as the primary mechanism to release the cells 100 post-processing. This eliminates the possibility that an added reagent, light source, or changed pH affects the phenotypic or genetic properties of the enclosed cells 100 for certain applications. Examples of released biofactors include: proteases, amylases, nucleases, ribozymes, and reduction/oxidative agents. Examples of degradable linkers include: peptides, di-sulfides, polynucleotides.

Cellular Self-Breakdown of Particles

While cellular breakdown of the hollow shell particles 10 may have a negative effect for some assays, it may allow for a natural and biocompatible release of the cells 100 from the hollow shell particles 10. Generally, the cells 100 may take some time or grow above a threshold colony size to release enough factors to structurally destabilize the hollow shell particles 10. So, the cells 100 can exhibit desired phenotypic properties and be selected/screened (if necessary) before the cells 100 self-degrade the particles. Alternatively, the cells 100 that cause the degradation of the hollow shell particles 10 may be selected based on their release while other cells 100 remain within hollow shell particles 10 and can be filtered out by the larger size of the intact hollow shell particles 10, for example using filter membranes or FACS scatter thresholds. As a result, a full assay can be performed and release of the cells 100 does not require the use of reagents that may damage the cells 100.

In one embodiment, the hollow shell particles 10 are crosslinked with peptide sequences and can be cleaved by factors released by enclosed cells 100. Encapsulated cells 100 can release themselves from hollow shell particles 10 several hours (1-24 h) or days (1-10 days) after an analysis, screen, or sort. For example, secreting cells 100 (e.g., T-cells, B-cells, hybridomas, stem cells, CHO cells) are selected or screened based on secretion properties (e.g., secretion rate, affinity, etc.) within minutes (10-60 min) or hours (1-12 h) of initial encapsulation and self-release themselves following the assay. The concentration and/or amount of degradable motifs in the particle's solid matrix can be adjusted to optimize the time it takes for encapsulated cells 100 to release enough factors to destabilize the particle. Lower concentrations or lower amounts of (e.g., 25-50% of crosslinkers) degradable motifs per particle generally increase the amount of time that hollow shell particles 10 take to destabilize and release cells 100. Higher concentrations or higher amounts of degradable motifs per particle generally decrease the amount of time that hollow shell particles 10 take to destabilize and release cells 100 (e.g., 50-100% of crosslinkers). The shell thickness of the hollow shell particle 10 may also be increased to decrease the rate of cell-induced self-degradation. In one example, cells 100 release enzymes that cleave peptides (proteases), nucleotides (nucleases), carbohydrates (glycosylases), or other polymer sequences within the particle's solid matrix. *Chlamydomonas* encapsulated MMP-degradable hollow shell particles 10 can start to and fully release themselves from the hollow shell particles 10 after ~24 h and ~96 h of incubation respectively (FIG. 19). This is likely due to the accumulation of MMPs released from the algae as previously discussed. In another embodiment, the hollow shell particles 10 are cross-linked with di-sulfide linkages that can be broken down with reducing agents released from enclosed cells 100. Examples of such reducing agents include free-thiol containing materials (e.g., proteins), thiol-disulfide oxidoreductases, thioreduxin, glutaredoxin, and gamma-interferon-inducible lysosomal thiol (GILT) reductase.

Other Methods of Breaking Down Particles

Hollow shell particles 10 may be broken down or destabilized via mechanical or physical methods. In some cases, it may be difficult to find a chemical method that does not damage enclosed cells 100 for certain applications. Therefore, it may be necessary to break down the particles using mechanical or physical methods such as pressure or shear. Such methods can be chosen so that the cells 100 also exhibit little to no damage due to the particular process.

In an example embodiment, the hollow shell particles 10 contains bonds that are broken when exposed to a certain level of physical pressure or shear. An example of applying physical pressure includes pressing a flat surface (microscope slide, piece of metal, 3D-printed object) onto hollow shell particles 10 that are settled on another flat surface. In some embodiments, the flat surface compressing the hollow shell particles 10 has ridges or other protuberances to maintain a minimal distance with the second flat surface in order to minimize damage to cells during the mechanical rupture of the hollow shell particles 10. Ridges or protuberances are generally taller than the diameter of individual cells 100, such as >5 micrometers or >15 micrometers. In addition, or instead, the flat surface compressing the hollow shell particles 10 may have pores or holes to allow fluid to flow through the surface while the two flat surfaces are brought together. Pore size of the holes may be smaller than the diameter of hollow shell particles 10 to prevent their loss through the pores during compression. In another example, hollow shell particles 10 are placed on top of mesh that has pores smaller than the diameter of the desired hollow shell particles 10 (e.g., cell strainer) and pressed down upon by a solid object (e.g., a pestle) to apply a shear stress that opens the hollow shell particles 10 and allow cells 100 to be released. In one example, hollow shell particles 10 are on the bottom of a microtiter plate and are exposed to a shearing stress via a solid object (e.g., 3-D printed piston, pestle, etc.). Shear stresses can also be exerted via vortexing or pipetting of the hollow shell particles 10.

Hollow shell particles 10 can be broken down by changing the pH of the solution that they are suspended in. The parameters of the initial pH and final pH must be chosen to be within a range that does not damage the cells 100 or the time that the cells 100 are exposed to the negatively impactful pH is short enough that enough cells 100 do not have detrimental long-term effects. Such a mechanism of breakdown may be necessary for some applications where the cell media (e.g., thiols in media) or cells 100 naturally break down (e.g., enzymes such as MMP) other potential crosslinker candidates. Examples of linkages that can be formed or broken via a raise or lowering of pH include imines, hydrazones, oximes, and epoxides. In an example workflow, cells that are viable in wide pH ranges (e.g., *Euglena gracilis* which can survive between a pH of 4 and 8) and are encapsulated into hollow shell particles 10 containing structurally-important and cleavable imine motifs. Precursor reagents can be dissolved at a pH of 7-8 to initiate solidification/polymerization immediately after droplet formation.

Precursor reagents can also be dissolved at acidic pHs (4-6.5) such that solidification does not initiate immediately after droplet formation. Solidification in this circumstance can be induced post-droplet formation with the addition of an oil-soluble base (e.g., triethylamine) that increases the pH to 7-8. This may ensure that phase separation occurs completely before solidification. Hollow shell particles 10 are suspended in *Euglena* media (Koren-Hunter media or Cramer-Meyers medium) that is also at a pH between 7 and 8 following fabrication and cell encapsulation. Hollow shell particles 10 are then allowed to stably incubate within this media for several days (2-10 days) to allow for *Euglena* biomass accumulation. Following screening, analysis, and/or sorting of hollow shell particles 10, the hollow shell particles 10 are placed in an acidic solution (pH between 4 and 6.5) that induces the cleavage of the structurally important imine bonds within the particle's solid shell matrix, causing the hollow shell particle 10 to structurally destabilize and release enclosed cells 100 and/or other materials.

The solid phase of the hollow shell particles 10 can also be destabilized via exposure to light. The solid phase of the hollow shell particles 10 can contain bonds that can be broken via specific wavelengths of light (e.g., UV, infrared, visible, etc.) that also have little to no effect on the phenotypic or genotypic properties of the cells 100. Examples of such bonds include nitrobenzyls and nitrophenethyls. In an example workflow, cells 100 (e.g., certain populations of yeast, bacteria, etc.) that can survive and/or have tolerable damage for the purposes of the particular assay at low intensities of UV light (<1000 mW-s/cm$^2$) are encapsulated into hollow shell particles 10 that contain nitrobenzyl groups that are structurally important to particle stability. Cell-containing hollow shell particles 10 are incubated in low UV light conditions (<1 mW-s/cm$^2$) where hollow shell particles 10 can remain stable for several hours (1-24 h) or several days (1-10 days) and cells 100 are allowed to exhibit desired phenotypic properties (e.g., growth, bioproduct accumulation, bioproduct secretion, etc.). Hollow shell particles 10 can then be analyzed, screened, and/or selected for desired properties of enclosed cells 100. Desired hollow shell particles 10 can then be irradiated with UV light (250-400 nm wavelengths) at 1-100 mW-s/cm$^2$ light intensities for several seconds (1-60 s), minutes (1-60 min), hours (1-24 h), or days (1-2 d) to cleave nitrobenzyl groups in order to destabilize hollow shell particles 10 and release enclosed cells 100 and/or other biomaterials.

Transport of Reagents Through the Solid Polymer Matrix

Pores within the solid polymer matrix also allow for the addition of reagents relevant for various assays described herein. Stains (e.g., fluorescent/magnetically labeled antibodies, nuclear or DNA stains, enzyme cleavable stains, fluorescently/magnetically labeled aptamers) can diffuse through the pores of the particle matrix to label certain cells or release biomolecules within the hollow shell particle 10. Enzymes (e.g., HRP) can also diffuse through the pores of the particle matrix to catalyze reactions relevant to readout (e.g., oxidation of ABTS in response to the presence of a particular biomarker). Lytic agents or permeabilization agents (e.g., detergents, surfactants, pore-forming complexes, and cell wall degrading enzymes) can also transport through the pores that can lyse or selectively degrade cell membranes and/or cell walls of cells 100 within hollow shell particles 10. This feature or reagent transportation may be important for multi-step assays that require the ability to exchange different reagents that stimulate and/or modify cells 100 or are important for reading out the properties of the cells 100. Premature or improper addition of these reagents may interfere with cell behavior or negatively impact proper readout. FIG. 11A illustrates the results of a FITC dextran diffusion study showing in one embodiment, a molecular weight cut-off between 70 kDa and 500 kDa for transport across the polymer shell of the hollow shell particle 10.

In one embodiment, labels can be added to certain cellular components. For example, labels can attach to certain organelles such as the nucleus (e.g., via hoescht, Cell Tracker nuclear stains, DNA intercalating dyes), mitochondria (e.g., BioTracker mitochondrial dyes, MitoView), lysosomes (e.g., BioTracher lysosome dyes, LysoView), endoplasmic reticulum (e.g., ER Tracer, CellLight ER), Golgi apparatus (e.g., CellLight Golgi), actin (e.g., phalloidin, ActinBlue, ActinRed, etc.), cytoplasm (e.g., CFSE), and others. In another embodiment, stains can characterize certain cellular activity.

For example, many assays require the use of stains (e.g., fluorescent/magnetically labeled antibodies, nuclear or DNA stains, enzyme cleavable stains) to characterize particular phenotypic properties. Such stains can be co-encapsulated within aqueous droplets. However, background stain remains entrapped and therefore it is difficult to adjust the stain concentration to reduce the signal-to-background ratio required to effectively recognize particular phenotypic traits during the screening process. This is particularly important for magnetic labeling and screening. Other assays require the addition of enzymes (e.g., HRP) to the compartment that catalyzes the production of a signal (e.g., fluorescent signal resulting from oxidation of ABTS, AmplexRed, etc.).

Premature addition of these enzymes may affect the phenotypic properties of the enclosed cells 100, so it may be important to add enzymes after some incubation time length. An assay may involve the addition of a biofactor that stimulates or inhibits some phenotypic trait of the enclosed cell 100 after the hollow shell particle 10 is transferred. For example, one may want to add protein (e.g., antibody, growth factor) to the cells 100 that stimulate a biological process (e.g., secretion, growth, etc.) mid-incubation. A user may also want to lyse the cells 100 post-incubation or post-screening/selection to capture or expose to reagents important internal components (e.g., genetic materials, proteins, etc.). So, lytic agents or buffers can be added to the solution, diffuse through the solid matrix, and reach the cells 100 to induce release or access to those cell-internal components.

Pore Size Parameters of Solid Phase

The optimal pore size range of the solid polymer matrix of the hollow shell particle 10 depends on a number of factors related to both fabrication as well as the specific applications. The pore size should be large enough such that inert material used for ATPS (e.g., dextran) can leak out but cells 100 remain within the hollow shell particles 10 (see FIG. 11B leakage study for 20 kDa dextran). So, the lower limit of the pore size is preferably around 5 nm (10 kDa materials have a hydraulic diameter of ~5 nm). The upper limit of the pore size is around 200 nm (largest reasonable size where particles can still be structurally stable). The pore size should also be large enough for relevant nutrients (e.g., glucose, vitamins, minerals) and proteins (e.g., antibodies, growth factors, enzymes) to be transported in and out of the solid matrix. Such materials range from 0.001-500 kDa in size and the pore sizes can range from 5 nm-200 nm. The pore size may also be tuned to allow for certain labels, stains, and other reagents to diffuse through the matrix. Examples of fluorescent, metallic, and magnetic labels can be around 50-800 Da on the lower end (e.g., stains such as BODIPY or Calcein AM) or 150-500 kDa on the upper end (e.g., antibodies, large protein). Magnetic particles used for labeling can also range from 10 nm to 200 nm in size. Methods to modify pore size are described in 'Methods of physical modification.'

Different Types of Labels

Fluorescently, magnetically, or metallically labeled molecules may be added to the compartment in order to characterize particular properties of the enclosed/captured biomaterials. Examples of fluorescent tags included but are not limited to FITC, TRITC, DAPI, Cy5, PE, Alexa Fluors, and DyLight. Magnetic tags generally include magnetic nanoparticles within the (10 to 200 nm range) covalently bound to an affinity molecule (e.g., antibody, etc.) or magnetic beads that are coated with functional groups (e.g., biotin, streptavidin, carboxylic acids, amines, thiols, antibodies, proteins). Examples of metal isotopes include $^{89}$Y, $^{141}$P, $^{159}$Tb, $^{165}$Ho, $^{169}$Tm, $^{209}$Bi, and others currently available or developed in the future.

In one embodiment, released biomolecules from cells 100 (e.g., secretions, intracellular recombinant proteins, genetic materials) captured within the compartment (via capture agents or size exclusion) are tagged with the addition of fluorescently/magnetically/metallically labeled molecules. For example, secretions (e.g., cytokines, antibodies) can be labeled with antibodies or antigens specific to the secretion of interest. Any unbound labels can be removed from the solution and hollow shell particles 10 by removing and replacing the surrounding solution. In another example, genetic material is retained within the hollow shell particle 10 due to size exclusion and labeled via a short nucleotide sequence that can hybridize with a particular region on the genetic material of interest. The pore size is fine-tuned such that the target genetic material is too large to exit the inner cavity 14 but the nucleotide label is small enough to pass freely in and out of the compartment. The short nucleotide sequence may comprise a molecular beacon, hairpin loop oligonucleotide with fluorophore and quencher, or fluorescently labeled oligonucleotide sequence with complementarity to a sequence of interest within the hollow shell particle 10.

In another embodiment, external or internal components of the enclosed cell(s) 100 are fluorescently, metallically, or magnetically labeled. The pore size of the particle's solid polymer matrix is adjusted such that the label is able to enter in and out of the inner cavity 14 but the cell(s) 100 of interest remain enclosed prior to particle degradation. In one example, an antibody with a fluorescent or magnetic label binds to specific components on the cell's membrane (e.g., protein receptors). A biomolecule (e.g., FSL, cholesterol, PEG-lipid conjugates) may also embed itself directly into the cell membrane. This biomolecule may have an already conjugated magnetic or fluorescent label or may contain an affinity agent (e.g., biotin) that later allows for the binding of such labels. In another example, dyes (BioTrackers, actin stains, etc.) can stain intracellular components (e.g., organelles, actin, non-secreted proteins) or stimulate intracellular fluorescence via an enzymatic reaction (e.g., calcein AM, Fluo-8 AM). In particular, internal genetic material can be stained with various types of nucleic acid stains: hoechst, cell trackers, propidium iodide.

Lytic Agents

Cells 100 may be lysed with reagents (e.g., enzymes, non-ionic detergents such as Triton X-100, Tween 20, etc. or ionic detergents such as sodium dodecyl sulfate, Sarkosyl, etc.) that can pass through the solid polymer matrix and enter the inner cavity 14. This is importantly used for applications where one wishes to analyze or sequence nucleic acids from cells 100 or internal non-secreted proteins or other biomolecules produced within cells 100. In one embodiment, hollow shell particles 10 containing cells 100 that have been selected based on the cell's phenotypic characteristics (e.g., B-cells that secrete antibodies towards a desired target) are mixed with lytic agents that can diffuse through the particle matrix. These lytic agents induce the lysis of enclosed cells 100 and the release of intracellular components. Desired released intracellular components are captured within the hollow shell particle 10. In one example, desired components (e.g., accumulated proteins) are retained within the hollow shell particle 10 due to the pore size of the particle's solid matrix being smaller than that of the desired protein. In another example, the particle matrix is modified to contain capture agents (e.g., nucleic acid sequences, primers, antibodies, aptamers, peptides) that can capture desired released targets (e.g., RNA, DNA, proteins, organelles, etc.). In a third example, the desired components (e.g., accumulated proteins) are retained within the hollow shell particle 10 by binding to an aggregating agent that increases the effective size of an aggregate of desired components such that it is larger than the pore sizes of the particle's solid matrix. The aggregating agent is preferably multivalent (e.g., bivalent, trivalent, or tetravalent) in order to facilitate the formation of aggregates and bridges of the desired components. For example, IgG antibodies, IgM antibodies, streptavidin-based affinity tetramers may be used as an aggregating agent. The aggregating agent may also be fluorescently labeled to enable analysis of the presence of the cell-released desired components.

Co-Encapsulated Beads or Cells

Beads that can capture/bind biomolecules released from cells 100 can also be encapsulated in the hollow shell particles 10. These beads/cells can either be free-floating in suspension within the inner cavity 14, bound on the surface of the particle's solid polymer matrix, or embedded within the particle's solid polymer matrix. The addition of beads allows for multiplexing capabilities that were not possible by direct modification of the particle's solid polymer matrix. For example, beads containing different binding motifs (e.g., secretion capture sites, genetic sequences) may be distinguished via different colors, sizes, and/or shapes. In one embodiment, T-cells 100 that secrete multiple types of cytokines (e.g., IL-8, IL-6) are encapsulated into hollow shell particles 10 that also contain multiple types of beads that are distinguished by color and/or shape and are coated with different antibodies specific to different cytokines. The secretion profile of the enclosed T-cells 100 can be characterized by allowing their secretions to bind to different beads, fluorescently labeling bound cytokines, and using screening/sorting tools to determine which cytokines were secreted within each hollow shell particle 10. Screening/sorting tools that can characterize the spatial location of such labels and objects such high-throughput imaging or image cytometry may be used for this assay. In another example, beads that can capture genetic material are barcoded via color, shape, and/or size and are co-encapsulated with one or more cells 100 of interest. The cells 100 are then lysed or porated to release genetic material that is selectively captured by the beads. The beads containing attached genetic material can then be used for amplification (RT-PCR, PCR, LAMP) and/or sequencing (Next-Gen sequencing, etc.). These processes can occur either while the hollow shell particle 10 is still intact or after degradation.

Multiple different types of cells 100 can be encapsulated within the same hollow shell particles 10 and can interact via direct binding or released biofactors. This allows one to characterize how a cell's phenotypic properties can influence another's behavior. In one embodiment, two or more cells 100 bind directly together, via the interaction of cell receptors, stimulating a response (e.g., apoptosis, secretion, intracellular trafficking) in one or both cells 100. In one example, binding of one or more T-cells 100 to a target cell line may induce secreted products that bind to the target cell 100 and induce cell death. In another example, a cell 100 may bind to another, stimulating pathways in one or both cells 100 that result in changes of intracellular processes (e.g., spatial location or size of organelles, accumulation of protein or genetic material). An encapsulated cell 100 may also have been genetically modified pre-encapsulation such that binding of a cell 100 or secretion results in the generation of fluorescent signals by the cell 100 (e.g., from internal production of GFP, RFP, etc.). This may allow a user to determine which particular pathway(s) are being stimulated. In another embodiment, secretions from one or more cells 100 bind to surface markers on other cells 100 that are co-encapsulated within the hollow shell particle 10. This is particularly useful to determine whether or not a secretion will bind to a target when it is embedded within a target cell 100 versus when the target is floating in free solution. For example, one can characterize the ability of antibodies secreted from a hybridoma or B-cell to bind to a particular antigen that is embedded within a target cell membrane.

Screening/Sorting of Desired Cell-Containing Particles

One key aspect is that the hollow shell particles 10 can be screened and/or sorted via a variety of commonly used high-throughput screening systems including: FACS, image activated cell sorting (IACS), microscopy, physical filters, and magnetic tools. This allows for a user to characterize the distribution of a population's phenotypic properties and/or select out particular cells 100 or growing colonies of interest. Hollow shell particles 10 can be screened/selected based on its fluorescence profile (via FACS, fluorescence microscopy) and/or spatial location of internal components (via IACS, microscopy) that can be differentiated by biological processes that previously occurred within the particle and/or labeling mechanisms. The hollow shell particles 10 can also be selected based on the presence of magnetic materials within the hollow shell particle 10. Such magnetic material may have resulted from magnetic labeling of cells 100 or secretions or may have resulted from the natural presence of magnetic material within the cells 100 (e.g., magnetotactic bacteria).

Flow/Mass Cytometry

Cell-laden hollow shell particles 10 that have been fluorescently labelled are able to be screened and sorted using automated high-throughput sorting systems such as flow cytometry (FC), FACS, mass cytometry (MC), and CyTOF. Fluorescent and metal isotope labeling of released biomolecules or cells 100 allows for cell-laden hollow shell particles 10 to be characterized by these systems, as discussed previously. Current flow cytometers such as BD FACSAria or Sony SH800 can sort and screen particles ranging from 10-100 μm in diameter at throughputs ranging from 1000-10,000 events/s. The On-Chip Sorter can sort and screen particles 10-150 μm in diameter at throughputs of 100-1,000 events/s. The BioSorter can sort and screen particles 50-500 μm in diameter at throughputs of 10-100 events/s. Mass cytometry systems such as Helios can screen particles 10-70 μm in diameter at throughputs of 100-2,000 events/s. However, mass spectrometry systems are not capable of sorting desired particles since current technologies significantly damage or kill cells.

In one embodiment, hollow shell particles 10 are sorted based on the presence and/or quantity of a single fluorescent marker. The signal may be the result of a fluorescent stain or some autofluorescence (e.g., chlorophyll) that is present in a cell 100 within the hollow shell particle 10. For example, hollow shell particles 10 that have retained microalgae (e.g., *Chlorella, Euglena, Chlamydomonas*) for several days are screened and sorted via a flow cytometer based on biomass accumulation of chlorophyll. Such accumulation is characterized by the amount of chlorophyll, which fluoresces in the Cy5 channel and roughly corresponds to the amount of algae biomass within the system. Variations within the population result in a distribution of microalgae with different growth rates, resulting in a distribution of fluorescence for each clonal colony within hollow shell particles that can be recognized by the flow cytometer (e.g., FACS). Cells 100 that have accumulated the most biomass during the incubation time can be selected using flow sorters or other means (e.g., filtration or size separation). Hollow shell particles 10 containing growing colonies of cells 100 can also be sorted by gating on forward and/or side scatter signal such as the area, height, and/or width of forward and/or side scatter signal. A larger forward and side scatter width is associated with a hollow shell particle 10 with a growing colony within. Once sorted by the FACS device, individual hollow shell particles 10 can then be loaded into separate volumes (e.g., wells of a multi-well plate) using index sorting functions on the instruments for further downstream analysis. In this regard, initial screening is performed using FACS sorting and is based, for example, on one property of the cell 100 contained in the hollow shell particle 10 (e.g., growth rate). These sorted hollow shell particles 10 can then be analyzed based on another property such as, for example, enzyme activity, secretion of a bio-product, or properties of a biosensor.

In a related embodiment, hollow shell particles 10 can be used for colony picking of bacterial, yeast, microalgae or other cells 100 at high-throughputs exceeding what is possible using standard automated colony picking tools from petri dishes or other 2D inoculation surfaces. Hollow shell particles 10 are loaded with a transformed population of yeast cells 100 following Poisson loading statistics to obtain a majority of cell-loaded hollow shell particles 10 containing single cells. The plasmid used to transform the yeast population also comprises a resistance gene or selective growth gene which enables selective growth of cells 100 which have taken up and are transcribing plasmid genes. For yeast, LEU2 gene is incorporated in the plasmid and cells 100 (BY4742 base) grown in Minimal SD base (Clontech 630411) with Dropout Supplement (-Leu). Hollow shell particles 10 are incubated to enable colony growth of only the transformed single yeast cells 100 which can be sorted by FACS based on forward and/or side scatter signal such as width of forward and/or side scatter signal to isolate hollow shell particles 10 containing growing single-cell derived colonies. The transformed cells 100 can be selected using standard antibiotics including bacterial beta-lactamase gene or eukaryotic antibiotic resistance gene aminoglycoside 3'-phosphotransferase to e.g., Carbenicillin or G418, respectively. Other selection strategies such as the removal of essential nutrients like amino acids like 1-tryptophane for the selection of yeast carrying e.g., a 1-tryptophane synthase are also possible. Growing single-cell derived colonies have increased scatter and can fill up hollow shell particles 10 leading to increased scatter width or scatter area signals. FACS sorting of single colonies into each well of a multi-well plate is performed where colonies can grow up for further downstream analysis and screening of recombinant products produced internally or secreted by the colony, using a variety well-plate enabled assays (e.g., fluorescence or colorimetric assays). One exemplary assay is an assay for recombinant enzyme turnover of a fluorogenic substrate in the well plate format (e.g., peptidases, lipases, or carboxylesterases). In these assays, fluorogenic substrate reagents are added to the wells and the reaction of the enzyme with the fluorogenic substrate is observed with fluorescence plate readers. Reactions are read at one end time point or time-dependent turnover can also be used as a metric. Results are normalized per cell concentration by also obtaining e.g., optical density readings using the plate reader or by imaging. Based on the output of the enzymatic assay a colony can be selected for further development and use. Throughput for colony picking can exceed previous approaches since >100 hollow shell particles 10 can be analyzed per second. Rare transformants can also be sorted more easily instead of having to streak multiple petri dishes or trays to assay a larger population.

Enrichment of Yeast Populations. In an exemplary embodiment, hollow shell particles 10 are used to enrich yeast cell 100 populations relevant for protein production based on desired phenotypic properties. For a fungal strain to be relevant for scaled-up biomanufacturing, it must exhibit specific properties: overproduction of desired protein or biomolecule, maintenance of modified gene(s), and increased biomass accumulation. Facile development of such strains has, as of yet, eluded large-scale manufacturers because of limitations with current selection systems. Specifically, currently, transformed colony picking is reliant on visually inspecting agar plates and inoculating individual colonies based on size after a given time. The throughput of this method is limited by the need to individually scrape or otherwise sample colonies off of an agar plate, as well as the amount of distinct colonies that can physically fit on a two-dimensional plate. This method is also limited in scope by its reliance on growth-rate alone as an indicator of colony viability. In many instances, faster-growing mutants are not the mutants that produce the most protein of interest, and may in fact end up outgrowing the cells that focus their metabolism on protein production rather than dividing. To remedy this, the ability to select particular clones based on multiple phenotypes (for example growth rate and protein production) in conjunction would be desired. Another issue one runs into when using the agar plate selection method of colony picking/sorting is the growth environment changing upon scale-up from plate to suspension bioreactor. Fungal cells that are grown on a plate are subject to a nutrient gradient that exists and changes in the agar media immediately surrounding the cell or colony. When the cells are moved to a bioreactor in suspension media, they may behave differently. As such, it is beneficial for fungal colonies be grown and selected for in a production-relevant environment.

Encapsulation. In this embodiment, eukaryotic fungal cells 100 such as *Saccharomyces cerevisiae* are encapsulated in hollow shell particles 10 that allow for the generation of yeast populations that accumulate biomass at a higher rate or overproduce a protein of interest. Other yeast species such as *Pichia pastoris* can also be encapsulated in such hollow shell particles 10, however, *S. cerevisiae* was chosen due to its ubiquity in fermentation and biomanufacturing processes. These yeast cells 100 are encapsulated into uniform hollow shell particles 10 using microfluidic droplet generators 200 as described herein. For this embodiment, one mixes the pre-polymer (20 kDa 4-arm PEG orthopyridyl disulfide), biocompatible inert material (40 kDa dextran), and crosslinker (DTT) within uniform droplets emulsified in Novec™ 7500 with 0.1% Pico-Surf™ surfactant at in-droplet concentrations of 3.25% w/w, 20% w/w, and 2.19 mg/mL respectively. The reagents are dissolved in PBS with a pH of 6.4, allowing disulfide crosslinking. The microfluidic channel heights and reagent flow rates can be adjusted to modulate the cavity size and outer diameter of the hollow shell particles 10. In this embodiment, hollow shell particles 10 are made with an outer diameter of ~45 μm and inner cavity that is ~40 μm in diameter. Cells 100 are prepared to an OD600 or about 3 million cells/mL of dextran solution. Following manufacture of the hollow shell particles 10, they are transferred to standard yeast-culturing media (YPD) or a dropout media to select for successful auxotrophic transformants at a concentration of 10,000-50,000 particles/μL. The solution is then placed in a shake incubator at 30° C. and 300 rpm.

Enrichment of Cell-containing Hollow Shell Particles. Cell-containing hollow shell particles 10 may be separated from empty hollow shell particles 10 prior to allowing yeast to accumulate biomass and intracellular protein. This may be useful in concentrating the cell-containing hollow shell particles 10 to enhance cell-cell communication and/or quorum sensing and/or reduce the amount of time it will take to sort out hollow shell particles 10 containing hyperproducing colonies following the incubation period. Optionally, fluorescence of produced GFP (or mCherry, or other engineered fluorescent protein or protein with an introduced tag that may be labeled, etc.) is used as the mechanism to distinguish hollow shell particles 10 containing yeast from empty hollow shell particles 10. Unsorted particle populations can be injected into a fluorescence-based flow sorter (nozzle size, channel, and/or tubing sizes ranging between 65 and 200 μm) and be sorted at a rate of 100 to 50,000 particles/s. Hollow shell particles 10 that produce a recognizable signal in the FITC channel due to GFP fluorescence can be selected/sorted and separated from non-cell containing hollow shell particles 10 that do not produce an observable signal. The sorted population may contain a 90-100% purity of yeast-containing hollow shell particles 10. Optionally, one can use the forward (FSC) and/or side scatter (SSC) produced by cells in flow cytometers to select hollow shell particles 10 with large amounts of cells 100. More cells 100 in a hollow shell particle 10 results in higher forward and side scatter, which can then be used as a growth rate-based sorting metric.

Incubation. The conditions that the particle-enclosed yeast cells are incubated in for biomass and protein accumulation is critical for proper selection. Ideally, the yeast-containing hollow shell particles 10 are incubated in physiologically or production relevant environments. Deviation from these environments may result in undesired selection pressures that result in the selection of strains with undesired phenotypes.

Optionally, yeast-containing hollow shell particles 10 are incubated under conditions that are generally used for the standard culture of yeast for a 1-2 day incubation period. In particular, particles containing *S. cerevisiae* are placed in yeast synthetic media (either complete or drop out). The particle-containing solution is placed within a container (e.g., culture flask, tube, etc.) that allows for diffusion of gases (e.g., oxygen, carbon dioxide, etc.). To incubate for the assay, the particle-containing solution is placed on a shaker, rotator, etc. that moves, shakes, rotates at 300 rpm at a temperature between 25° C. and 30° C. (ideally 30° C.).

Final Sort and Cell Release. A Sony SH800 cell sorter was used for the selection of desired colony-containing hollow shell particles 10. A 130 μm chip size was used to select the hollow shell particles 10 sized from 45-60 μm depending on the number of cells 100 contained within them. Hollow shell particles 10 were run through the sorter at a rate between 100 and 500 events/second. Drop delay needed to be adjusted to account for the larger size of the particles compared to standard single cells. The sorter was equipped with a 488 nm excitation laser and FITC (510/23 nm) bandpass filter which was used to quantify the amount of expressed GFP within the particle 10. Forward scatter (FSC) was used to quantify the number of fungal cells 100 within the hollow shell particles 10.

Yeast-containing hollow shell particles 10 coupled with the highest 0.1-1% FSC signal and highest 0.1-1% FITC signal as quantified with the flow sorter were sorted. A Drop Delay of −0.5 to −5 ms was used for sorting. In one example, all target hollow shell particles 10 were sorted into a single 1 mL microtube, 1.5 mL Eppendorf tube, 12×75-mm tube, or 15 mL conical tube. In another example, individual full hollow shell particles 10 were sorted into separate wells of a 96-well plate. In each example, collection tubes/wells contain culture medium prior to sorting. Post-sorting, yeast cells 100 are released from hollow shell particles 10 with the addition of 20 mM DTT and washed with media to remove free polymer from solution.

As another example, *Chlorella* colonies seeded and cultured in hollow shell particles 10 were selected based on biomass accumulation rate using a FACS instrument. The colony's chlorophyll autofluorescence was used, appearing in the Cy5 channel (ex:620, em:647), as a metric for biomass accumulation (FIG. 23A). Generally, colonies containing greater numbers of cells 100 also contain higher amounts of chlorophyll, generating higher Cy5 fluorescence readouts. Lipids could also be stained through the hollow shell particles 10 by mixing BODIPY with the colony-containing hollow shell particles 10 (FIG. 23B). However, to simplify the study design to focus on improving the engineering aspects of the workflow, clonal colonies were sorted only based on biomass accumulation rate of chlorophyll and not lipid productivity. *Chlorella* was encapsulated at an average loading density, lambda of 0.1, which resulted in 91.7% of cell-containing hollow shell particles 10 with no more than a single cell 100.

Following culture for 48 hours, hollow shell particles 10 containing *Chlorella* colonies were sorted using the On-Chip Sort at an average event rate of 100-200 events/sec. Three distinct populations were observed in the forward scatter height [FSC(H)] vs side scatter height [SSC(H)] plot: one from colony-containing hollow shell particles 10, one from empty hollow shell particles 10, and one from debris (FIG. 23C). The debris population was confirmed to be from particulates naturally present in *Chlorella* media. If the media is filtered, a greatly reduced fraction of debris events is observed. As expected, ~85.7% of detected hollow shell particles 10 do not contain cells 100 due to the lambda=0.1 that was used. In agreement with contrast observed in brightfield microscopy, hollow shell particles 10 that contain microalgal colonies generally have increased forward and side scatter intensities. It was verified that most of the colony-containing hollow shell particles 10 are within this high FSC/SSC gate by demonstrating that events in this gate also contained the highest Cy5 fluorescence (i.e., chlorophyll autofluorescence). A selected sample based on this gate had 94.0% purity of colony containing hollow shell particles 10.

Using the On-Chip Sort, hollow shell particles 10 with the fastest growing colonies were sorted out by gating on chlorophyll autofluorescence. When selected hollow shell particles 10 from different regions of the Cy5 distribution of colony-containing particles, differing numbers of microalgae 100 were observed in the sorted colonies (FIG. 23D). Hollow shell particles 10 gated on the lowest 50% in the Cy5 channel and within the high scatter gate possessed on average 9.2±3.7 cells 100. This was statistically different from colonies recovered when gating the highest 50% (19.5±7.1 cells 100, $P<0.0001$) and highest 15% (27.0±7.2 cells 100) (FIG. 23E). Before sorting, colony-containing hollow shell particles 10 contained on average 13.0±7.7 cells 100. Overall, higher Cy5 fluorescence intensities corresponded to hollow shell particles 10 with a greater number of cells 100 and given the loading conditions favoring single cell-derived colonies, it is likely these hollow shell particles 10 contained microalgae sub-populations that have faster doubling times and/or biomass accumulation rates (FIG. 23E).

The workflow used to select *Chlorella* colonies based on Cy5 fluorescence was used for selection and regrowth of hyper-performing *Chlorella* subpopulations. Here, colonies were released from the hollow shell particles 10, re-cultured, and verified after re-culture that the selected sub-population accumulated biomass faster than an un-selected population (FIG. 24A). For these studies, hollow shell particles 10 with more than one cell 100 initially was minimized by loaded by using lambda=0.05, resulting in 3.2% of all particles containing colonies and ~98.3% of cell-loaded particles containing no more than one cell 100. Following 48 h of growth in hollow shell particles 10 immersed in *Chlorella* native media, colony-containing hollow shell particles 10 were sorted by gating those hollow shell particles 10 to have the highest 11.1% of Cy5 fluorescence (425 events were selected from a population of 3839 colony-containing hollow shell particles 10).

Selected colonies were released from hollow shell particles 10 by applying mechanical shearing stress onto the hollow shell particles 10, causing them to rupture. Hollow shell particles 10 were disrupted with mechanical shear and released cells 100 were re-cultured in a flask (FIG. 24C). The biomass accumulation rate of the selected sub-population of cells 100 during re-culture was compared to an un-selected population of cells 100 by seeding each population at the same concentrations and tracking their cell concentrations over a 4-day period (FIG. 24C). It was observed that the selected sub-population of cells 100 had an ~8% faster growth rate than the un-selected population (doubling times of 10.2 h and 11.2 h respectively, $P<0.01$) for the first 48 h of growth after seeding. This resulted in a 40% difference in the cell concentrations 48 h after seeding that can be visibly seen in the culture flask (FIG. 24D). The difference in accumulated biomass at this time point was also evaluated by measuring the total chlorophyll autofluorescence within well-mixed aliquots from each culture at this time point (FIG. 24E), resulting in 27.6% increase in chlorophyll autofluorescence for the selected sub-population of cells 100. As expected, the differences in cell number and overall chlorophyll biomass between the two populations diminished after 48 h as the cultures reach carrying capacity.

In another particular example, B-cells 100 or hybridomas 100 are screened based on antigen specificity for monoclonal antibody drug discovery. Following the injection of an animal with a target antigen, a rare number of the animal's B-cells, plasmablasts, plasma B-cells 100 (~0.1% of the population) secrete antibodies specific towards the particular antigen that need to be separated from the other non-specific cells. After extracting B-cells from the animal, the cells 100 can be encapsulated into hollow shell particles 10 that capture all secreted antibodies via capture sites in the solid polymer matrix or co-encapsulated beads or aggregating agents as described above. The cells 100 can also be immortalized to form hybridomas before this step. Following incubation of the cells 100 within the hollow shell particles 10, the hollow shell particles 10 can be mixed with a fluorescently labeled target antigen. These target antigens are able to diffuse through the matrix and only bind to antibodies specific to respective antigen. Unbound labels can then be washed away such that only those hollow shell particles 10 containing cells 100 that secrete antibodies towards the target antigen contain a fluorescent or metallic signal. These cell laden hollow shell particles 10 can then be flowed through a flow sorter that can sort hollow shell particles 10 based on the presence of a fluorescent signal, effectively allowing the automated isolation of desired antibody secreting cell lines.

In another embodiment, cells 100 are screened or sorted based on the quantitative fluorescence intensity of each of the particle's bound fluorescent labels. This effectively allows for the quantification of the released biomolecules. For example, CHO cells 100 with a high secretion or accumulation rate of therapeutic proteins can be selected in order to reduce costs of therapeutic protein development. In one particular aspect, CHO cells 100 can be transfected with plasmid(s) encoding for a recombinant antibody. The transfected cells 100 can then be encapsulated into hollow shell particles 10 containing antibodies specific to the heavy chain fragment of the therapeutic antibody (e.g., anti-human Fc IgG). The cell-laden hollow shell particles 10 can then be labeled with a fluorescent stain that binds to region(s) on the light chain fragment of the respective antibody (e.g., antigen, anti-human light chain IgG). Unbound labels can then be washed away. Only those hollow shell particles 10 containing cells 100 that secreted both the appropriate heavy and light chain fragments will have a fluorescent or metallic signal, allowing one to remove CHO cells 100 that cannot form both fragments of the therapeutic protein via flow sorting. During sorting, one can also sort out hollow shell particles 10 with the highest fluorescence or metal intensities (e.g., top 5-10%) that correlate to greater amounts of secreted antibody within the hollow shell particle 10 and thereby contain the faster secreting cells 100. The sorted cells 100 can then be re-cultured, re-encapsulated, and re-screened to test the stability of the sorted population. For example, stable cell lines will have a narrow fluorescence or metal distribution and will exhibit a similar fluorescence or metal intensity as the initially sorted cell after the same incubation time. Unstable cell lines will have a broader fluorescence intensity distribution.

In another embodiment, hollow shell particles 10 are sorted based on the presence and/or quantity of two or more fluorescent signals. This effectively allows a user to multiplex and screen/sort based on multiple phenotypic properties. In one example, microalgae cells 100 are sorted based on both biomass and lipid accumulation. After microalgae are encapsulated into hollow shell particles 10 and allowed to accumulate biomass over a period of time, their lipids are fluorescently stained (e.g., BODIPY) with a label that can be fluorescently distinguished from the chlorophyll (e.g., FITC, TRITC). As a result, the cell-laden hollow shell particle 10 may contain two distinguishable fluorescent signals that characterize two different phenotypic traits: chlorophyll biomass and lipid accumulation. In flow, hollow shell particles 10 that have both the highest chlorophyll fluorescence and highest stained-lipid fluorescence are sorted. In another example, hollow shell particles 10 containing secreting cells 100 can be sorted based on both secretion rate and biomass accumulation. After secreting cells 100 are allowed to accumulate captured secretions and grow within the hollow shell particle 10 for an incubation time, both the secretions and nuclei are stained using previously discussed methods. Ideally, the stains do not have too much overlap in their excitation/emission spectra so that they can be distinguished in flow. Using a flow sorter, hollow shell particles 10 containing cells 100 with high growth and secretion rates can be selected.

In another embodiment, the hollow shell particles 10 are used for library generation. Here, FACS selected cells 100 (i.e., clones) are sorted into an arrayed format for further screening. This enables the generation of high-quality arrayed libraries that only contain productive clones, i.e., clones that e.g., express a protein of a desired property such as binding to a protein or basal enzymatic activity. The advantage of this technology is that clones without activity or protein expression can be eliminated upfront which reduces downstream costs by orders of magnitudes and enables rapid quantitative determination of expression levels and activity levels which are required for downstream applications such as antibody production. Using imaging flow cytometry (or other sorting techniques), this platform may also be used to satisfy the FDA requirement for clonal selection of antibody producing clones for the development of therapeutic antibodies.

Imaging Techniques

Hollow shell particles 10 can also be screened using various imaging techniques. Unlike FC and MC systems that only allow for the quantity of fluorescent and metallic signal(s) respectively, imaging techniques can characterize the localization of fluorescent labels or other materials within the hollow shell particles 10 and/or within cells 100. In one embodiment, hollow shell particles 10 are imaged using microscopy techniques. Hollow shell particles 10 can be placed within compartments (e.g., wells, capillaries, micropins, etc.) that can be imaged. Desired hollow shell particles 10 can be removed with techniques such as manual/robotic pipetting, optoelectronic tweezers, light-displacement, acoustic trapping or manipulation, or other volume displacing techniques. In another embodiment, hollow shell particles 10 are imaged using image-activated cell sorting (IACS) devices and may be selected based on flow sorting techniques (e.g., pressure or flow pulse, droplet-in-air, dielectrophoretic). Both imaging techniques may include confocal or light sheet imaging techniques that allow for appropriate focusing of necessary elements that may be located within different imaging planes within the hollow shell particle 10.

In one example application, hollow shell particles 10 contain a cell 100 of interest and co-encapsulated cell(s)/bead(s) that can capture released biomolecules from the cell 100 of interest. For example, the cell 100 of interest can be a secreting cell 100 (e.g., hybridoma, B-cell, T-cell) that is co-encapsulated with other cells 100 or beads that capture released secretions (e.g., antibodies, cytokines). Co-encapsulated beads can be coated with secretion targeting materials (e.g., antibodies, aptamers, peptides) or antigen that can capture desired secretions. Multiple types of beads with different binding motifs can be enclosed within the hollow shell particle 10 and distinguished via fluorescence, metallic labels, size, or shape. Such a system makes it possible to perform assays involving multiplexing of multiple secretions. Co-encapsulated cells 100 can contain surface markers that secretions can bind to (e.g., antigens, etc.). Co-encapsulated cells 100 can also lack surface markers that desired secretions can bind to and serve as a control. Multiple cell types within the hollow shell particles 10 can be distinguished with fluorescent or metallic labels/stains. Cells 100 may be suspended freely within the inner cavity 14. Cells 100 may also be attached to or embedded within the solid matrix of the hollow shell particle 10. Fluorescent or metallic labels can then be used to label desired secretions and the localization of the secretions relative to co-encapsulated beads and/or cells 100 can be determined using previously mentioned imaging techniques.

In another example application, imaging techniques can be used to determine biomass accumulation within the hollow shell particles 10. When the hollow shell particles 10 are used for such applications with fluorescent/metallic techniques, the cells 100 either need to be fluorescently/metallically labeled or comprise autofluorescent molecules. In circumstances where the cells 100 do not contain autofluorescence, fluorescent/metallic labels used to characterize biomass accumulation may change cell behavior following such labeling. For example, nuclear stains may induce genetic alterations that affect a cell's properties post-staining. The amount of biomass accumulation within hollow shell particles 10 are characterized using brightfield imaging techniques, eliminating the need for labels that may alter cell behavior. Colonies containing biomass accumulation desired properties (e.g., those that grow faster) are then selected using techniques as discussed herein.

In one application, imaging techniques can be used to determine the location of cells 100 within the hollow shell particle 10. For example, these techniques are used to determine the degree of adherence of cell lines to motifs within the outer solid polymer matrix. In one example, binary characterization of the cell binding/adherence to the solid polymer matrix is determined. This can be used to select out only those hollow shell particles 10 containing cells 100 that bind/adhere to the solid polymer matrix. In another example, the motifs are antibodies, peptides, aptamers or other elements that are used for an affinity maturation process. The specificity of these motifs are characterized based on the percentage of cells 100 within the hollow shell particle 10 that attach to the motifs within or on the solid phase.

In another embodiment, the cells 100 used in this technology express a surface tag that bind to a peptide sequence that is incorporated into the material/matrix of the shell 12 thus enabling the binding of cells 100 such as suspension cells 100 that otherwise do not bind to the shell material. The advantage being that in the absence of the peptide, the cells 100 can be used for suspension culture again without any further changes needed.

In another application, imaging techniques are used to determine the spatial location of co-encapsulated cells 100 relative to each other. For example, a user can characterize the ability of two or more cells 100 to bind to each other due to particular motifs on their surface and/or particular conditions surrounding the cells 100. In one particular example, imaging techniques and hollow shell particles 10 are used to select out T-cells 100 that secrete cytokines that bind to one or more target cells 100 and/or directly bind via surface elements to one or more target cells 100. In one embodiment, T-cells 100 and target cells 100 (e.g., cancer cells, other immune cells) are encapsulated into peptide linked hollow shell particles 10 with an outer diameter ranging from 50 to 120 μm and an inner diameter ranging from 40 to 115 μm using techniques previously described. Prior to encapsulation, cells are stained with different fluorescence markers so that they can be distinguished during selection. In one embodiment, the nuclei of the different cells 100 are stained with dyes with different fluorescence markers. For example, T-cells 100 can be stained with CellTracker Blue, Target Cell 1 can be stained with CellTracker Red, Target Cell 2 can be stained with CellTracker Deep Red, etc. In another embodiment, surface markers specific to the cell type are fluorescently labeled. For example, CD8+ T-cells 100 may be labeled with fluorescently tagged anti-CD8 antibodies. If target cell lines are adherent, the particle's solid matrix can contain binding motifs (RGD, antibodies, fibronectin, etc.) that enable adherence of such target cells 100 to the inner cavity 14. Methods and techniques for fluorescently labeling secretions and cells 100 have been previously discussed.

The cell-containing hollow shell particles 10 may be incubated in a variety of conditions for 0.5-12 h or 1-2 days while co-encapsulated cells 100 interact with each other directly or through secretions. In one embodiment, the cell-containing hollow shell particles 10 are placed into standard culture medium for T-cells (e.g., RPMI with FBS, other trace elements, antibiotics) and incubated at standard cell culture conditions (e.g., 35-40° C., 3-10% $CO_2$, 80%+ humidity). In another embodiment, hollow shell particles 10 are placed in blood plasma and incubated at standard cell culture conditions. The blood plasma may also contain un-encapsulated cells (Red Blood cells, NK cells, etc.) that directly (via secretions) or indirectly (via modifications to particle-containing solution) interact with cells 100 within hollow shell particles 10.

Several types of T-cell/target cell interaction assays can be characterized using this workflow. Hollow shell particles 10 containing cells 100 exhibiting desired secretion/binding properties are screened and sorted using image activated cell sorting. Such tools are capable of spatially locating fluorescently labeled secretions and cells 100 in respect to each other and are able to determine which cells 100 fluorescently labeled secretions are bound to and whether or not cells 100 are in contact with one another which likely indicates binding. In one embodiment, the target cell 100 contains a surface marker that cytokines from the T-cell can specifically bind to. Another cell line that is the same as the target cell but without the particular surface marker of interest (removed via CRISPR knockout, etc.) can be co-encapsulated to serve as a control. Only those hollow shell particles 10 containing fluorescently labeled cytokine secretions located on the target cell 100 with the target receptor but not on the cell 100 without the target receptor are selected. In another embodiment, functionality of a T-cell surface binding agent (e.g., CAR or TCR receptor) is characterized by co-encapsulating desired T-cells 100 with target cell(s) 100 with the target surface markers. Those hollow shell particles 10 containing T-cells 100 that appear spatially connected to the target cell 100 are selected. Hollow shell particles 10 may also contain a control cell 100 that does not contain the desired surface maker. In a final embodiment, hollow shell particles 10 are selected based on a combination of secretion and cell binding properties. For example, only hollow shell particles 10 that contain T-cell 100 that bind to target cells 100 (e.g., cancerous cell line) and secrete cytokines that bind to immune effector cells (e.g., NK cells, helper T-cells, etc.) are selected. Following selection, hollow shell particles 10 are broken down or opened to release cells 100 using previously discussed techniques.

Magnetic Separation of Desired Cell-Containing Particles

Advantages of Magnetic Separation

Previous studies have shown the selection of cells 100 based on the fluorescent labelling of cell secretions in fully solid spherical particles without a hollow inner cavity. In these studies, particles of interest were selected via FACS only. FACS systems require large and expensive equipment for the appropriate optical configurations and flow tools to perform such high throughput operations, and throughput of large particle sorters is still limited. Magnetic sorting systems do not require such optical and flow equipment, reducing the size and cost of the sorting tool. Magnetic sorting is also a parallel process compared to FACS which is a serial process, leading to higher throughput of sorting with magnetic approaches. As a result, more researchers and developers will be able to perform high throughput screening based on cell phenotypes with cheap and easy to use equipment, ultimately accelerating the development of cell-derived therapies and products. Also, the majority of standard FACS systems have a limited particle size (~55 μm) that can be flowed through the sorter. Other fluorescence sorting systems such as Union Biometrica's BioSorter and On-Chip Biotechnologies On-Chip Sort are compatible with particles in a larger size range but they do not have the same widespread placement as FACS. The magnetic tools described below can easily be designed to be compatible with larger particle sizes, making it easier to generate cell associated particles.

Standard Magnet Sorting

In one embodiment, hollow shell particles 10 are placed adjacently to a magnetic field gradient generator that attracts hollow shell particles 10 that have a magnetic label 16 (FIG. 27). Hollow shell particles 10 that are magnetically labeled can either be placed in tubes (e.g., microcentrifuge, conical), microtiter plates (384 well plates, 96 well plates), or dishes that contain aqueous solution. The magnetic field can be applied via the presence of a solid magnet 18 (as illustrated) or a magnetic coil. Un-labelled hollow shell particles 10 can then be separated from labelled hollow shell particles 10 via washing (e.g., centrifugation, pipetting, pouring) or labelled hollow shell particles 10 can be isolated by moving the magnet field generator to move the labelled hollow shell particles 10 into a new compartment (e.g., tube, well) or a different region of the tube, plate, dish or other holder of hollow shell particles 10.

Magnetic Column Sorting

With reference to FIG. 28, a separate mechanism involves running the hollow shell particles 10 through a magnetic column composed of paramagnetic microspheres 20 magnetized with an external magnetic field (e.g., magnet). The microspheres 20 are appropriately sized such that the spacing between the spheres 20 serve as pores that hollow shell particles 10 can pass through. Hollow shell particles 10 can pass through the column either by gravitational forces or flow/pressure-based systems. Hollow shell particles 10 that are not magnetically labelled will pass easily through the pores of the magnetic column and into a collection compartment (e.g., tube, well). Hollow shell particles 10 that are magnetically labelled will be attracted to the temporarily magnetized paramagnetic microsphere(s) 20 on the magnetic column due to attractive magnetic forces. In a related aspect, the microspheres 20 can be ferromagnetic such that the column consists of a continuous magnetic field. Magnetically labelled hollow shell particles 10 that have been magnetically separated from non-magnetically labelled hollow shell particles 10 via an elution buffer, enhanced flow, release of the external magnetic field. In another aspect, the microspheres 20 are formed from of a paramagnetic material that only becomes magnetized in the presence of a magnetic field. During hollow shell particles 10 separation, a magnetic field can be placed adjacent to the column, effectively magnetizing the microspheres, allowing them to magnetically attract magnetically labelled hollow shell particles 10. Upon removal of unbound hollow shell particles 10, the source of the magnetic field can be removed away from the column, thereby demagnetizing the column. Thus, magnetically labelled hollow shell particles 10 are no longer attracted to the column, can flow freely, and can be isolated via elution.

Magnetic Ratcheting

The separation of magnetically labelled cells 100 using a continuous flow, quantitative platform called the magnetic ratcheting technology has been demonstrated. The magnetic ratcheting approach can achieve quantitative separations based on the amount of magnetic content of a particle. In the magnetic ratcheting system, arrays of magnetic micro-pillars combined with a directionally cycled magnetic field create dynamic potential energy wells that trap and manipulate magnetic particles in a magnetic-content and particle-size dependent manner. Using 1:1 aspect ratio permalloy micro-pillar arrays the magnetophoretic force envelope has been increased some 10-fold compared to thin film ratcheting systems. Increased force not only decreases processing time but enables the use of small particles which are advantageous due to their increased labeling efficiency attributed to large diffusion lengths, and the ability to have a larger number of quantized labeling levels compared to larger particles. Furthermore, by designing an array of ferromagnetic elements with a gradient in pitch in the row or column direction, particles or cells with varying magnetic contents will equilibrate in different spatial locations and be separated from each other; as particles or cells with higher magnetic content will have higher critical pitches. Furthermore, particles or cells with similar magnetic content will concentrate into quantized bands at the critical pitch under a given driving frequency. As mentioned, the ratcheting system is an effective tool to capture and quantitatively separate rare cell types in both laboratory and clinical settings. Particularly, the system addresses the major challenge of purity that has plagued traditional MACS based systems. Therefore, the magnetic ratcheting system is one of the ideal tools for separation and can be used for the differential sorting of particles based on the amount of magnetic content in a quantitative fashion. An example of a magnetic ratcheting system may be found in U.S. Pat. No. 10,144,911, which is incorporated by reference herein.

Microfluidic Flow

In another embodiment, hollow shell particles 10 are flowed in solution through a microchannel exposed to a magnetic force. Following inertial focusing of the hollow shell particles 10, a magnetic force can be applied to the channel such that magnetically labelled hollow shell particles 10 will be deflected and can be captured in a separate flow stream and downstream outlet channel.

Enrichment of Algae Populations

In an exemplary embodiment, hollow shell particles 10 are used to enrich microalgae cell 100 populations relevant for biofuel production based on desired phenotypic properties. For a particular hyper-producing algae strain to be relevant for scaled up production, it must exhibit the following properties: overproduce high-energy lipids, hyperperform in biomass accumulation rate, and have relatively small photosynthetic antenna sizes that limit shading in production environments. Unfortunately, developing such a strain has been elusive because of limitations in the tools to select for such algae. Specifically, algae populations that overperform in lipid production rate have been developed using FACS-based selection. However, these populations underperform in biomass accumulation rate and cannot be improved using FACS-based selection because standard flow cytometry systems only characterize single cells and cannot characterize growth rate on its own. Turbidostats or other bioreactors are common tools used to select cells with higher growth rates. However, turbidostats and other bioreactors take a very long time (months) to generate overperforming populations with the growth rates and population sizes that are required. Also, these culture enrichments can very easily select for undesired phenotypes such as cells that stick to the vessel walls or to each other. Importantly, the high cell densities required for effective use of turbidostats and other bioreactors limits the amount of light available to cells, resulting in the undesired selection of algae with oversized photosynthetic antennae size. So, it is important to use a high throughput screening tool that can select for the combined traits of high biomass accumulation rate, high lipid production rate, and small photosynthetic antenna size. Also given the high sensitivity of microalgae (and other cells) to selective pressures, it is critical that algae are selected based on their performance in a production-relevant environment.

Encapsulation

In this embodiment, marine microalgae cells 100 such as *Chlorella vulgaris* are encapsulated in hollow shell particles 10 that enable for the generation of microalgal populations that overproduce lipids, overperform in biomass accumulation rate, and/or have relatively small antenna sizes. Other microalgae species such as *Euglena gracilis* and *Chlamydomonas reinhardtii* can also be encapsulated into such hollow shell particles 10. However, *Chlorella* and *Nannochloropsis* gaditana are specifically chosen because they can be cultured in marine environments, making large-scale cultures of such algae non-competitive for freshwater sources that are important to agriculture, and have a history of being researched for the production of high energy lipids such as triacylglycerols (TAGs) that are precursors for biofuels/biodiesels. These microalgae strains are encapsulated into uniform hollow shell particles 10 using droplet generators, previously described. For this embodiment, one mixes the biocompatible pre-polymer (20 kDa 4-arm PEG maleimide), biocompatible inert material (10 kDa dextran), and biocompatible crosslinker (di-cysteine TEV-degradable peptide, COOH-GCENLYFQGCG-$NH_2$, [SEQ ID NO: 2]) within uniform droplets emulsified in Novec™ 7500 with 0.25% Pico-Surf™ surfactant at in-droplet concentrations of 3.25% w/w, 12% w/w, and 3.45 mg/mL respectively. Each of the reagents are dissolved in marine media at a pH of 6.5, a pH that allows for crosslinking between 4-arm PEG maleimide and di-cysteine TEV-degradable peptide at an appropriate speed. The flow rates and channel geometries can be adjusted (as previously discussed) to fabricate hollow shell particles 10 that are ~60 μm in diameter and have an inner cavity 14 size of ~55 μm. The hollow shell particle 10 diameters and cavity sizes have a CV of less than 5%. Cells 100 are encapsulated at a concentration of 1.5 million cells/mL in the initial dextran solution (to ensure that ~90% of cell-containing particles have no more than one cell, as can be estimated using Poisson statistics). Approximately 80% of hollow shell particles 10 contain no cells 100. When transferred from oil to aqueous solution, the hollow shell particles 10 are suspended in marine media at a pH 7 and a particle concentration of 100-30,000 particles/μL. The particle concentration is chosen such that cell-containing hollow shell particles 10 are concentrated enough such that cells 100 in adjacent hollow shell particles 10 can interact via cell-cell communication and/or quorum sensing factors but dilute enough such that there is a normal diffusion of gases and nutrients and hollow shell particles 10 can move when the solution that they are suspended in is agitated within a shaker flask that is continuously agitated at 25 to 300 RPM (ideally 120 RPM).

Enrichment of Cell-Containing Particles

Cell-containing hollow shell particles 10 may be separated from empty hollow shell particles 10 prior to allowing algae to accumulate biomass and lipid. This may be useful in concentrating the cell-containing hollow shell particles 10 to enhance cell-cell communication and/or quorum sensing and/or reduce the amount of time it will take to sort out hollow shell particles 10 containing hyperproducing colonies following the incubation period.

Optionally, autofluorescence of chlorophyll (e.g., can be observed in the Cy5 channel) is used as the mechanism to distinguish hollow shell particles 10 containing algae from those that don't contain algae. Unsorted particle populations can be injected into a fluorescence-based flow sorter (nozzle size, channel, and/or tubing sizes ranging between 65 and 200 pin) at a throughput ranging from 10 to 50,000 particles/s. Hollow shell particles 10 that produce a recognizable signal in the Cy5 channel due to chlorophyll autofluorescence can be selected/sorted and separated from non-cell containing hollow shell particles 10 that do not produce an observable signal. The sorted population may contain a 50-100% purity of algae-containing hollow shell particles 10.

Optionally, one can use the forward (FSC) and/or side scatter (SSC) produced by cells 100 in flow cytometers to produce particle populations with a larger percentage of cell-containing hollow shell particles 10. PEG-based hollow shell particles 10 were shown to produce significantly lower FSC and SSC than cells 100 (algae and mammalian cells) in flow cytometers. Therefore, one can distinguish between those hollow shell particles 10 containing cells 100 and those without cells 100 in flow and sort only those hollow shell particles 10 containing cells 100. One can also adjust gating such that only hollow shell particles 10 that produce the top 70-95% FSC and/or SSC readouts are selected to reduce the number of false positives due to debris, deformed particles, mechanical errors, etc.

Optionally, hollow shell particles 10 containing algae cells 100 with small photosynthetic antennae (or chlorophyll) can also be selected using this approach. The intensity of a single microalgae in the Cy5 channel is directly proportional to the amount (both in terms of number and size) of photosynthetic antennae present within that cell 100. So, algae selected with lower Cy5 fluorescence will generally have a smaller amount of photosynthetic antenna. In one example, a subpopulation of hollow shell particles 10 within the population of hollow shell particles 10 that contain algae can be selected. Of those hollow shell particles 10 triggering an observable chlorophyll fluorescence, algae-containing hollow shell particles 10 containing the lowest 0.1-40% of chlorophyll fluorescence can be selected from those algae-containing hollow shell particles 10 with higher chlorophyll fluorescence, resulting in a sorted population of hollow shell particles 10 that contain algae with a lower amount of photosynthetic antenna than an unsorted population. Sorting based on low levels of chlorophyll autofluorescence can also reduce the number of hollow shell particles 10 that contained more than one cell 100 during loading, improving the accuracy of later selection steps.

Incubation

The conditions that the particle-enclosed algae cells 100 are incubated in for biomass and lipid accumulation is critical for proper selection. Ideally, the algae-containing hollow shell particles 10 are incubated in physiologically or production relevant environments. Deviation from such environments may result in undesired selection pressures that result in the selection of strains that have undesired properties or do not exhibit the same desired properties when placed in such physiologically or production relevant environments.

Optionally, algae-containing hollow shell particles 10 are incubated under conditions that are generally used for the standard culture of algae for a 3-10 day incubation period. In particular, particles containing *Chlorella* are placed in marine media with a standard/normal composition at a particle concentration of 100-30,000 particles/μL. The particle-containing solution is contained within a container (e.g., culture flask, tube, etc.) that allows for diffusion of gases (e.g., oxygen, carbon dioxide, etc.) and has some degree of transparency such that the solution can be exposed to light. To incubate for the assay, the particle-containing solution is placed on a shaker, rotator, etc. that moves, shakes, rotates between 25 and 300 RPM (ideally 120 RPM) at a temperature between 20° C. and 40° C. (ideally 30° C.) with 0-3% atmospheric $CO_2$ (ideally 1%) and 50-500 μE light (ideally 150 μE).

Optionally, algae-containing hollow shell particles 10 are incubated in scaled-up production environments or within particular devices relevant for analysis or scale up of algal strains. In one example, algae-containing hollow shell particles 10 can be placed within large aqueous environments (>5 L) at outdoor or indoor cultivation plants. Algae-containing hollow shell particles 10 may be kept within a particular subsection of the environment using solid barriers or mesh/netting that have pore sizes smaller than the particle diameters (pore sizes of 0.1-100 μm). The algae-containing hollow shell particles 10 may also be co-incubated with other non-encapsulated microorganisms such as other algae or bacteria. Hollow shell particles 10 cultured in such environments may be re-isolated from non-encapsulated cells 100, debris, or materials before further processing (e.g., sorting or screening) by passing particle-containing solution through a mesh/netting (e.g., cell strainer) that have pore sizes (e.g., 0.1-100 μm) smaller than the size of the desired hollow shell particles 10 but larger than undesired elements. Hollow shell particles 10 can be concentrated from large volume sizes via centrifugation, magnetic isolation via magnetic elements on or within particles, etc.

Final Sort and Cell Release

Algae containing hollow shell particles 10 that contain *Chlorella* colonies with the coupled overperformance in biomass accumulation rate, overproduction of lipids, and limited photosynthetic antennae (chlorophyll) size and amount are selected using a flow sorter. Following the incubation period and before sorting, the lipids of encapsulated *Chlorella vulgaris* are stained by adding 1-10 μg/mL BODIPY 505/515 to the particle-containing solution at room temperature and in the dark for 0.5-2 h. Unbound BODIPY is then removed from the solution via a series of centrifugation/washing steps using marine culture media or DPBS. Before injection into the flow sorter, hollow shell particles 10 are suspended into DPBS at a concentration of 50,000-500,000 particles/mL. Optionally, 0.1-0.5% (w/v) pluronic F68 or pluronic F127 is added to the particle solution before injection to reduce the number of hollow shell particles 10 that stick to the sorter's tubing/machinery.

A BD FACSAria was used for the selection of desired hollow shell particles 10. A 85 μm, 100 μm, or 130 μm nozzle size was used and hollow shell particles 10 were injected at a throughput rate between 200 and 5000 events/s. Drop delay is adjusted to account for the larger size of the hollow shell particles 10 compared to normal cells. To screen/quantify chlorophyll autofluorescence within each hollow shell particle 10, the flow sorter is equipped with a 561 nm excitation laser and PE-Cy5 (698/70 nm) bandpass filter. To screen/quantify the amount of lipid within each particle (via BODIPY 505/515), the flow sorter is equipped with a 488 nm excitation laser and FITC (510/23 nm) bandpass filter. Forward scatter (FSC) is used to quantify the number of algal cells within each hollow shell particles 10.

Algae-containing hollow shell particles 10 coupled with the highest 0.1-1% FSC signal, highest 0.1-1% FITC signal, and lowest 0.1-1% Cy5 signal as quantified within the flow sorter were sorted. A Drop Delay of −0.5 to −5 ms was used for sorting. In one example, all hollow shell particles 10 were sorted into a single 1 mL microtube, 1.5 mL Eppendorf tube, 12×75-mm tube, or 15 mL conical tube. In another example, individual hollow shell particles 10 were sorted into separate wells of a 96- or 384-well plate. In each example, collection tubes/wells contain culture medium prior to sorting. Post-sorting, algal cells 100 are released from hollow shell particles 10 with the addition of TEV-protease at a concentration of 0.1-1 units/μL for 0.5-2 h at 30° C. and a 7-8 pH.

Enrichment of Hyperproducing CHO Cells

In one embodiment, hollow shell particles 10 are used to select ExpiCHO cells 100 transfected with a humanized antibody that have both the highest secretion and growth rates. CHO cells 100 are encapsulated into hollow shell particles 10 with an outer diameter of 60 μm and an inner diameter of 55 μm using techniques previously described. The hollow shell particles 10 are made using a 3-inlet flow focusing droplet generator injected with biocompatible pre-polymer (4-arm PEG-maleimide), biocompatible inert material (10 kDa dextran), and biocompatible crosslinker (di-cysteine modified MMP-degradable peptide (Ac-GCRDGPQGIWGQDRCG-$NH_2$, [SEQ ID NO: 1]). Dextran and di-cysteine modified MMP-degradable peptide are injected at in-droplet concentrations of 12% w/w and 1.21 mg/mL respectively in ExpiCHO cell expression culture medium at a pH of 6.5. The pre-polymer phase contains 75% 4-arm PEG-maleimide and 25% chemically inert 4-arm PEG such that the pore size of the particle's solid phase is large enough to allow un-captured antibodies and labeling antibodies to pass freely in and out of the inner cavity 14. Final total PEG in-droplet concentration is 3.25% w/w in ExpiCHO cell expression culture medium at a pH of 6.5. Final in-droplet concentrations of 4-arm PEG maleimide and chemically inert 4-arm PEG are 2.4375% w/w and 0.8125% w/w respectively. Free thiol-containing anti-human Fc antibodies are placed in the crosslinker phase at a concentration of 50-1000 μg/mL and conjugated to the particle's solid polymer matrix during particle formation. These anti-human Fc antibodies will capture humanized antibodies secreted from CHO cells 100 during incubation.

CHO-cell containing hollow shell particles 10 are placed into a batch reactor or bioreactor that is commonly used for scaled-up CHO cell recombinant protein production (e.g., HyPerforma Bioreactor) for a 1-3 day period to allow encapsulated cells 100 to grow and secrete. Culture conditions are 37° C., pH 7, 50-120 RPM impeller speed, and 20-40% dissolved oxygen. The solution that the cell-containing hollow shell particles 10 are suspended in may or may not contain non-encapsulated cells 100 that can directly (via cell-cell communication) or indirectly (via alteration of solution) interact with particle-encapsulated cells 100. Hollow shell particles 10 are isolated post-incubation using size-exclusion techniques previously described.

Secretions are labeled with antigen that the secreted antibody is specific to that is tagged with Alexa Fluor 488. To stain, hollow shell particles 10 are placed into DPBS at a concentration of 500,000-1,000,000 particles/mL and with 1-500 nmol antigen for 0.5-2 h at 37° C. (ideally in an incubator with 8% atmospheric $CO_2$ and 90% humidity). Optionally, the nuclei of the CHO cells 100 are simultaneously stained with the hollow shell particles 10 being stained with fluorescent antigen by including 5-25 μM CellTracker DeepRed in the particle-containing solution at the same incubation conditions. Unbound stain(s) are removed from the solution via a series of centrifugation/washing steps. Hollow shell particles 10 are suspended in DPBS at a concentration of 50,000-500,000 particles/mL prior to sorting.

A BD FACSAria II is used for the selection of desired hollow shell particles 10. A 85 μm, 100 μm, or 130 μm nozzle size is used and particles are injected at a throughput rate between 200 and 5000 events/s. To screen/quantify the amount of fluorescently labeled antibody secretions, the flow sorter is equipped with a 488 nm excitation laser and FITC (510/23 nm) bandpass filter. The number of cells 100 in each hollow shell particles 10 was quantified either using FSC or CellTracker DeepRed fluorescence. In the circumstance that CellTracker DeepRed fluorescence was used to quantify the number of cells 100 in each hollow shell particles 10, the flow sorter is equipped with a 633 nm excitation laser and a Cy5 (670/30) bandpass filter. Hollow shell particles 10 containing CHO cell colonies with both the highest 0.1-1% amount of secretion (as quantified by the FITC channel) and greatest 0.1-1% number of cells (as quantified via FSC or the Cy5 channel) were selected. A Drop Delay of −0.5 to −5 ms was used for sorting. In one example, all hollow shell particles 10 are sorted into a single 1 mL microtube, 1.5 mL Eppendorf tube, 12×75-mm tube, or 15 mL conical tube. In another example, individual hollow shell particles 10 are sorted into separate wells of a 96- or 384-well plate. In each example, collection tubes/wells contain culture medium prior to sorting.

Post-sorting, CHO cells 100 are released from hollow shell particles 10 with the addition of trypsin at a concentration of 0.01-0.05% (w/v) at 37° C. for 1-15 min. Trypsin activity is then inhibited with 1-20% (w/v) FBS and trypsin is separated from the released cells via a series of centrifugation/washing steps.

Selection of Hybridomas Based on Secretion Affinity to Target Cells

In one embodiment, hybridomas 100 formed from immortalized B-cells extracted from an antigen immunized mouse are selected based on their secreted antibody's ability to bind to a particular antigen located on the surface of a target cell. Prior to encapsulation, three cell types (hybridomas, target cell with target antigen on surface, and control cell without target antigen on surface) were stained with different CellTracker dyes comprising distinguishable emission spectra. Each type of cell 100 is stained in different batches by placing the cells 100 in DPBS at a cell concentration of 200,000-500,000 cells/mL with 5-25 μM of the respective CellTracker dye for 0.5-2 h at 37° C. Unbound dye is removed via a series of centrifugation/washing steps. In this embodiment, hybridomas are stained with CellTracker Blue, target cells with target antigen on surface are stained with CellTracker Green, and control cells without target antigen on the surface are stained with CellTracker DeepRed. Control cells are the same base-cell type as the target cell 100 are made by using CRISPR knockout techniques to remove genetic sequences encoding for the surface antigen of interest.

The three cell types are simultaneously encapsulated into hollow shell particles 10 crosslinked with di-cysteine modified MMP-degradable peptide using techniques previously described. The average hollow shell particle 10 diameter is ~60 μm and the average cavity size is ~55 μm. Pore size of the outer solid shell is increased by including chemically inert 4-arm PEG in the pre-polymer phase, as previously discussed. Cells 100 are placed in the inert material, dextran, phase so that they are encapsulated into the hollow shell particles 10. Hybridomas 100 are encapsulated at a concentration of 1.5 million cells/mL in the initial dextran solution to ensure that ~90% of Hybridoma-containing hollow shell particles 10 have no more than one cell 100 and ~80% of hollow shell particles 10 contain no hybridomas. To ensure that 90% of hollow shell particles 10 contain at least one target cell 100 and one control cell, target cells 100 and control cells are each placed at a concentration of 25,000,000 million cells/mL in the dextran phase prior to encapsulation. Over 80% of target cell- and control cell-containing hollow shell particles 10 have more than one of the respective cell type.

Following particle formation, the cell-containing hollow shell particles 10 were incubated for a 0.5-2 h period to allow secretions to be released from hybridomas and potentially bind to the other cell types. Hollow shell particles 10 were incubated in DMEM supplemented with 10% FBS, 50-100 IU/mL Penicillin, and 50-100 μg/mL Streptomycin at 37° C., 5% $CO_2$ concentration, pH 7.0, and 90% humidity. The particle concentration is kept between 100 and 30,000 particles/mL.

Following incubation, the culture media is replaced with DPBS via a series of centrifugation/washing steps to remove unbound secretions and bound secretions are fluorescently stained with anti-mouse antibodies conjugated with Alexa Fluor 555. To stain, hollow shell particles 10 are placed into DPBS at a concentration of 500,000-1,000,000 particles/mL and with 10-100 μg/mL anti-mouse antibodies for 0.5-1 h at 37° C. (ideally in an incubator with 5% atmospheric $CO_2$ and 90% humidity). Unbound fluorescent antibodies are removed via a series of washing/centrifugation steps. Prior to sorting, hollow shell particles 10 were placed in DPBS at a concentration of 50,000-500,000 particles/mL Image Activated Cell Sorting (IACS) is used to select out hybridomas 100 that secrete antibodies that specifically bind to the target antigen on the target cell 100 and not the control cell. A 85 μm, 100 μm, or 130 μm nozzle size was used and hollow shell particles 10 were injected at a throughput rate between 50 and 2000 events/s. The image sorter was able to detect and spatially recognize the following fluorescent markers within hollow shell particles 10: CellTracker Blue (B-cells) via a 355 nm excitation laser and a DAPI (420/20 nm) bandpass filter, CellTracker Green (target cells) via a 488 nm excitation laser and a FITC (530/30 nm) bandpass filter, CellTracker DeepRed (control cells) via a 633 nm excitation laser and a Cy5 (670/30 nm) bandpass filter, and Alexa Flour 555 (secretion label) via a 561 nm excitation laser and a PE (586/15) bandpass filter. Using high-throughput imaging analysis software, only those hollow shell particles 10 with spatial overlap between Alexa Fluor 555

(secretion label) and CellTracker Green (target cells) but no spatial overlap between Alexa Fluor 555 and CellTracker DeepRed (control cells) are selected using the system. Hollow shell particles 10 that contained no Alexa Fluor 555 fluorescence or have Alexa Fluor 555 fluorescence that spatial overlaps with both CellTracker Green and CellTracker DeepRed are not sorted by the system. Selected particles are placed into separate, individual wells on a 384- or 96-well plate. Post-sorting, cells 100 are released from hollow shell particles 10 with the addition of trypsin at a concentration of 0.01-0.05% (w/v) at 37° C. for 1-15 min. Trypsin activity is then inhibited with 1-20% (w/v) FBS and trypsin is separated from the hollow shell particles 10 via a series of centrifugation/washing steps. The mRNA of the selected hybridomas are sequenced via RNA reverse transcription, cDNA amplification, and sequencing tools to obtain the sequences for the $V_H$ and $V_L$ regions of the selected cell's antibodies.

Sorting and Analysis of Protein Accumulation in Yeast

In one embodiment, hollow shell particles 10 are used to select yeast colonies that over-accumulate a desired recombinant protein within production-relevant environments. Yeast cells 100 are encapsulated into MMP-degradable hollow shell particles 10 with a 40 μm outer diameter and 35 μm cavity diameter using previously detailed methods. Yeast are placed in the inert material phase (dextran phase) at a concentration of 1.5 million cells/mL to ensure that ~90% of yeast-containing particles have no more than one cell 100.

Yeast are incubated for 1-3 days following encapsulation to allow yeast to grow and accumulate protein within the hollow shell particles 10. Optionally, these yeast-containing hollow shell particles 10 are placed into standard yeast cultures (yeast broth rotating at 300 RPM at 30° C.) at a particle concentration of 100-30,000 particles/mL. Optionally, yeast-containing particles are placed into a bioreactor containing yeast broth at 37° C., pH 7, 300 RPM impeller speed, and 20-40% dissolved oxygen.

Following the incubation period, pores are generated in the yeast cell membrane using electroporation (1.0-1.5 kV, 400-600 V/cm) such that accumulated protein is released from the cells 100 while maintaining cell viability. The pore size of the particle's solid matrix is smaller than the size of the desired protein, causing such proteins to be physically retained within the particle's inner cavity 14. The hollow shell particles 10 were placed in 0.02% v/v SYPRO Red Protein stain for 0.5-1 h at room temperature to label released proteins. The stain is small enough such that it can pass through the pore matrix of the particle's solid phase and reach the proteins. Unbound stain is washed away via a series of centrifugation/washing steps and the hollow shell particles 10 were placed into DPBS at a concentration of 50,000-500,000 particles/mL prior to sorting.

Particles containing yeast colonies that over-accumulate protein are selected using a FACSAria II. The flow sorter is equipped with a 488 nm excitation laser and a PerCP-Cy5.5 (695/40) bandpass filter to detect SYPRO Red Protein stain. A 85 μm, 100 μm, or 130 μm nozzle size was used and hollow shell particles 10 are injected at a throughput rate between 200 and 5000 events/s. Hollow shell particles 10 that produce the highest 0.1-1% PerCP-Cy5.5 fluorescence are sorted into a single 1 mL microtube, 1.5 mL Eppendorf tube, 12×75-mm tube, or 15 mL conical tube pre-filled with yeast broth.

Following sorting, yeast cells 100 are released from hollow shell particles 10 with the addition of trypsin at a concentration of 0.01-0.05% (w/v) at 37° C. for 1-15 min. Trypsin activity is then inhibited with 1-20% (w/v) FBS and trypsin is separated from the released cells 100 via a series of centrifugation/washing steps. Released cells 100 are then re-cultured for further selection and/or analysis.

As explained herein, a variety of crosslinking modalities may be used to generate the hollow shell particles 10. These include, for example, crosslinking using radiation such as ultraviolet light or via pH mediated crosslinking. Likewise, various release mechanisms are available to release the contents of the hollow shell particles 10. These include sodium periodate ($NaIO_4$), use of MMP enzymes, trypsin, DTT or TCEP. Table 1 below illustrates a summary of various hollow shell particle 10 variations as well as their advantages and disadvantages.

TABLE 1

| | Throughput (Particles/hour) | Chemical Release Mechanism | Primary Advantage | Primary Disadvantage |
|---|---|---|---|---|
| DTT-crosslinked via UV | 2.5 million | Sodium periodate | High fabrication throughput | Unclear how UV light will affect cells |
| DTT-crosslinked via pH | 1.3 million | Sodium periodate | Compatible with most growth assays | Limited to mechanical degradation to viably release cells |
| Peptide-crosslinked via pH | 1.3 million | MMPs or Trypsin | Cells can be chemically released | Cells may prematurely release themselves via secretions |
| Disulfide-crosslinked via pH | 1.3 million | DTT or TCEP | Can be chemically released | Only compatible with robust cell types such as yeast and bacteria |

Hollow shell particles 10 can be placed and remain stable in more production-relevant environments (e.g., a shaking culture flask, bioreactor, outdoor cultivation farms) that are not possible with other high-throughput selection technologies (e.g., droplet technology, microwells, etc.). The porous outer shell 12 enables solution exchange with the external environment, allowing replenishment of nutrients, diffusive transport and dilution of cytotoxic cellular waste, access to quorum sensing factors from external cells/colonies, and exposure to natural concentration, temperature, light, or physical gradients in the culture environment. As a result, hollow shell particles 10 can enable cell line developers and researchers to select cells 100 based on their behavior in production-relevant environments, making it much more likely that selected populations will exhibit the desired phenotypic properties when scaled up for real-world applications.

Size-Based Sorting of Yeast Subpopulations by Growth Rate

In one embodiment, a cell strainer or similar size-based filter is used to select yeast mutant cells 100 based on growth rate. *Saccharomyces cerevisiae* is encapsulated into chemically-degradable hollow shell particles 10 as described herein, with one out of every ten hollow shell particle 10 containing a single yeast cell 100. Hollow shell particles 10 are cultured for an amount of time commensurate with doubling time. Optionally, these yeast-containing hollow shell particles 10 are placed into standard yeast cultures (e.g., yeast broth rotating at 300 RPM at 30° C.) at a particle concentration of 100-30,000 particles/mL. Optionally, yeast-containing hollow shell particles 10 are placed into a bioreactor containing yeast broth at 37° C., pH 7, 300 RPM impeller speed, and 20-40% dissolved oxygen.

The hollow shell particles 10 expand as they are filled with yeast cells 100, and can then be sorted based on diameter with the use of physical strainers or other filters. This is illustrated in FIGS. 20A-20B. Of course, FACS may also be used to sort colonies such as the workflow illustrated in FIGS. 21A-21B. Optionally, the fastest growing subpopulations can be sorted out with a single strainer with pores smaller than the desired particle size resulting from yeast cell growth but larger than the non-expanded hollow shell particles 10. This may be done in order to isolate the fastest growing subpopulations or to remove the fastest growing subpopulations in order to maintain a population that divides more slowly. Optionally, a set of cell strainers or other size-based filters may be used in succession in order to isolate subpopulations within a desired band of growth rates. Following sorting, yeast cells 100 are released with the addition of a reducing agent, chemically degrading the hollow shell particle 10, or through mechanical disruption such as by allowing the growing yeast to stretch and rupture the hollow shell particles 10. The cells 100 are then pelleted and transferred into media for re-culturing.

Materials and Methods—Selection of Microalgae Based on Biomass Accumulation Rates in Hollow Shell Particles Bulk Culture of Cells

*Chlorella* cells 100 (CCMP1124 from National Center for Marine Algae and Microbiota) used in the study were provided by Synthetic Genomics, Inc. *Chlorella* populations were cultured in 500 mL Erlenmeyer flasks containing seawater-based medium with added vitamins, trace metals, nitrate, phosphate, and sodium bicarbonate (SM-NO3 medium). SM-NO3 medium was also supplemented with penicillin-streptomycin (P/S, Thermo Fisher Scientific, 15140122). *Chlamydomonas* reinhardii (STR CC-4568) and *Euglena gracilis* Z (NIES-48) procured from Microbial Culture Collection at National Institute for Environmental Studies (NIES) Japan were cultured in 500 mL using Tris-acetate-phosphate medium and Koren-Hunter (KH) medium at a pH of 5.5 respectively. Flasks containing algae cultures were shaken continuously at 120 RPM with constant 150 μE light at room temperature. Algae cultures were kept at a concentration of 2-10 million cells/mL. Strains of *Saccharomyces Cerevisiae* were obtained from Sigma-Aldrich (STR YSC1). The yeasts were grown in yeast extract (1%, w/v) peptone (2%, w/v) glucose (2%, w/v) (YPD) media supplemented with 50 mg/L ampicillin (Sigma-Aldrich, 69534). The strains were grown in 250 mL Erlenmeyer flasks containing 100 mL of YPD, under aerobic conditions at 30° C. with agitation (300 rpm). Adherent CHO DP-12 cells (ATCC CRL-12445) were cultured in media containing DMEM (Invitrogen) supplemented with 10% FBS, 1% P/S, 0.002 mg/mL recombinant human insulin (Sigma), 0.1% Trace Elements A (Fisher Scientific), 0.1% Trace Elements B (Fisher Scientific), and 200 nM Methotrexate (MTX, SIGMA). CHO DP-12 cells 100 were also cultured in incubators at 37° C. and 5% $CO_2$.

Hollow Shell Particle Fabrication

Mechanically-degradable hollow shell particles 10 demonstrated throughout the majority of the study were fabricated forming uniform water-in-oil droplet emulsions containing in-droplet concentrations of 5% (w/w) 10 kDa 4-arm PEG-maleimide (4-arm PEG-MAL, Laysan Bio), 11% (w/w) 10 kDa dextran (Sigma Aldrich, D9260), and 1.54 mg/mL dithiothreitol (DTT, Sigma Aldrich, 10197777001). Reagents were dissolved into SM-NO3 medium, YB, TAP, or KH medium for the encapsulation of *Chlorella, S. cerevisiae, C. reinhardtii*, or *E. gracilis* cells 100 respectively (each at a pH of 6.25). Novec™ 7500 Engineered fluid (3M™, 297730-92-9) with 0.5% Pico-Surf™ (Sphere Fluidics, C024) acting as surfactant was used as the continuous, oil phase. Droplet emulsions were formed using a 4-inlet microfluidic channel fabricated with polydimethylsiloxane (PDMS) using standard soft-lithography techniques. Reagents were loaded into separate syringes and pushed through the PDMS droplet generator 200 using syringe pumps (Harvard Apparatus, MA, USA). In order to reduce the effects of functionalized PEG and crosslinker on cell growth during encapsulation in the hollow shell particles 10, cells 100 were suspended in the dextran phase such that the cells 100 only interact with the PEG and DTT reagents for a short period of time. In-droplet concentrations of 3.25% (w/w) 20 kDa 4-arm PEG Ortho-Pyridyldisulfide (4-arm PEG-OPSS, Creative PEGWorks, PSB-459), 10% (w/w) 10 kDa dextran, and 0.80 mg/mL DTT were used to form di-sulfide linked hollow shell particles 10. In-droplet concentrations of 5% (w/w) 10 kDa 4-arm PEG-MAL, 11% (w/w) 10 kDa dextran, and 14.1 mg/mL di-cysteine modified Matrix Metallo-protease (MMP) (Ac-GCRDGPQGIWGQDRCG-$NH_2$, [SEQ ID NO: 1]) (Genscript) peptide substrate were used to form MMP-degradable hollow shell particles 10.

Following droplet generation, emulsions were stored at room temperature for 1 h to allow the hollow shell particles 10 to fully solidify. The hollow shell particles 10 were de-emulsified by adding Pico-Break™ (Sphere Fluidics, C081) at a 1:1 volume ratio on top of the hollow shell particles 10. Once Pico-Break™ had passed through all the hollow shell particles 10, the hollow shell particles 10 were transferred into aqueous solution (DPBS or cell media) containing 10 μM N-ethylmaleimide (NEM, Sigma-Aldrich, E3876) at a pH of 6.5. The hollow shell particles 10 were kept in NEM solution for 0.5 h to allow NEM to react to any free thiols on the particles to reduce clumping. hollow shell particles 10 were then passed through a 100 μM cell strainer to remove any oversized or clumped particles and a 40 μM cell strainer to remove any free cells 100 or small debris before being transferred into cell media to be used for the particular assay.

Hollow Shell Particle Versus Droplet Emulsion Growth Comparison

*Chlorella* and *S. cerevisiae* cells 100 from the same respective initial culture were separately encapsulated into mechanically-degradable hollow shell particles 10 and microfluidically-generated droplets in oil of approximately the same volume (155 pL) using the same droplet generator 200. Each cell type was encapsulated into hollow shell particles 10 and droplets within 2 h of each other. Hollow shell particles 10 and droplets containing *Chlorella* were incubated in Eppendorf tubes with constant 150 μE light at room temperature (no shaking). Compartments containing *S. cerevisiae* were incubated in Eppendorf tubes at 30° C. (no shaking). Both hollow shell particles 10 and droplets were not shaken since droplets tend to de-emulsify when shaken at speeds >100 RPM. Hollow shell particles 10 and droplets were imaged using an inverted microscope in BF and Cy5 (ex: 620 nm, em: 676 nm) fluorescence at equal time intervals over a multi-day period to track the growth of cells 100 in their respective compartments over time.

Staining of Intracellular Lipids

Following a 48 h culture of *Chlorella* in hollow shell particles 10, intracellular lipids were stained with $BODIPY^{505/515}$. Stock $BODIPY^{505/515}$ was prepared by dissolving 4-Difluoro-1,3,5,7-Tetramethyl-4-Bora-3a,4a-Diaza-s-Indacene (Life Technologies, D3921) powder into dimethyl sulfoxide (DMSO) at a concentration of 2.5 mg/mL and then diluted to 2.5 μg/mL using SM-NO3 media. Colony-containing hollow shell particles 10 were placed at a concentration of $2\times10^6$ particles/mL in SM-NO3 media before being mixed at a volume ratio of 1:1 with 2.5 μg/mL BODIPY$^{505/515}$ and incubated in the dark for 0.5 h. The hollow shell particles 10 were washed three times with SM-NO3 before being imaged in the FITC channel (ex: 488 nm/em: 543 nm) using a fluorescence microscope.

Incubation and Flow Cytometric Sorting of Hollow Shell Particles

*Chlorella* cells 100 were encapsulated into 90 μm diameter hollow shell particles 10 following Poisson loading with lambda=0.1 for the initial sort and lambda=0.05 for the full selection and placed into SM-NO3 medium at a particle to media volume ratio of 1:50. The particle-containing solution was then placed in a 250 mL Erlenmeyer flask shaking at 120 RPM and at room temperature under constant 150 μE light for 48 h to allow cells to accumulate biomass. Colony-containing hollow shell particles 10 were screened and sorted using an On Chip Sort (On Chip Biotechnologies, USA). The cytometer was equipped with both 488 nm and 561 nm excitation lasers and a PE-Cy5 (676/37 nm) filter. Events were triggered based on particle absorbance from the 488 nm laser. Hollow shell particles 10 were sorted based on their scatter readouts and thresholding desired intensity heights through the PE-Cy5 filter. Hollow shell particles 10 solutions were concentrated in fresh SM-NO3 media at a 1:10 particle to media volume ratio for screening and sorting. Hollow shell particles 10 within the selection gates were dispensed in a single collection reservoir. The sorted hollow shell particles 10 were then imaged using an inverted microscope and the number of cells 100 in each hollow shell particle 10 was counted using MATLAB code.

Release of Cells and Re-Culture of Selected Populations

Post-selection, *Chlorella*-containing hollow shell particles 10 were placed onto a 37 μm cell strainer and placed over a 15 mL conical tube containing fresh SM-NO3 media supplemented with P/S. The hollow shell particles 10 were then ruptured by 'grinding' the hollow shell particles 10 with a pestle and washing with SM-NO3 media for ~5 min, causing released cells 100 to fall through the pores of the cell strainer and into the fresh media. Despite being able to be ruptured by direct mechanical shearing pressure, hollow shell particles 10 remain stable in adverse indirect mechanical shearing pressures such as mixing, vigorous pipetting, and vortexing. The solution containing released cells 100 was then transferred into a 250 mL Erlenmeyer flask and put in standard bulk *Chlorella* culture conditions for 7 days to allow released cells 100 re-grow to a concentration of 15-20 million cells/mL.

To test for maintenance of an enhanced biomass accumulation phenotypes in the selected population, the selected population and an un-selected population were seeded into separate 250 mL Erlenmeyer flasks with SM-NO3 media supplemented with P/S at a concentration of 500,000 cells/mL. The flasks were placed side-by-side under standard *Chlorella* culturing conditions for 4 days. The cell concentration was measured using a hemocytometer every 12 h. At 48 h of growth, biomass accumulation was measured by aliquoting several fractions from the selected and un-selected sample into a well plate and measured the chlorophyll density (parameters) using a well plate reader at this time point.

Chemically-Induced Degradation of Hollow Shell Particles

To chemically degrade the various types of hollow shell particles 10, the hollow shell particles 10 were first diluted or concentrated to a concentration of $1\times10^6$ particles/mL and added the following reagents at the indicated final concentration to degrade each hollow shell particles 10 type: 10 μg/mL sodium periodate ($NaIO_4$, Fisher Scientific, P120504) for hollow shell particles 10 crosslinked with 4-arm PEG-MAL and DTT, 10 mg/mL DTT or 3 mg/mL Tris(2-carboxyethyl)phosphine (TCEP, Sigma-Aldrich, 646547) for hollow shell particles 10 crosslinked with 4-arm PEG-OPSS and DTT, and 0.0025% Trypsin with EDTA (Thermo Fisher Scientific, 25300120) for hollow shell particles 10 crosslinked with 4-arm PEG-MAL and di-cysteine modified MMP degradable peptide.

While embodiments of the present invention have been shown and described, various modifications may be made without departing from the scope of the present invention. The invention, therefore, should not be limited, except to the following claims, and their equivalents.

What is claimed is:

1. A method of using a particle system comprising a plurality of hollow shell particles formed from a biocompatible and chemically or physically degradable crosslinked hydrogel, each hollow shell particle having a void or cavity formed therein and surrounded by a shell of crosslinked hydrogel, and one or more live cells contained in the void or cavity, the method comprising incubating the plurality of hollow shell particles in a growth medium for a period of time to obtain multicellular colonies contained in at least some of the plurality of hollow shell particles followed by subjecting the plurality of hollow shell particles to sorting by flow cytometry, wherein the sorting operation sorts hollow shell particles based on accumulated biomass of the multicellular colonies contained in respective hollow shell particles using a forward and/or side scatter signal obtained during flow cytometry.

2. The method of claim 1, further comprising releasing the multicellular colonies from the plurality of hollow shell particles that are sorted.

3. The method of claim 2, wherein the releasing is performed by the presence of cleaving molecules generated by the multicellular colonies or cleaving molecules exposed to the plurality of hollow shell particles.

4. The method of claim 2, wherein the releasing is caused by exposing the plurality of hollow shell particles to an environmental stimulus.

5. The method of claim 2, wherein the releasing is caused by one of pressure, shear stress, or mechanical stretching.

6. A method of using a particle system comprising a plurality of hollow shell particles formed from a biocompatible and chemically or physically degradable crosslinked hydrogel, each hollow shell particle having a void or cavity formed therein and surrounded by a shell of crosslinked hydrogel, and one or more live cells contained in the void or cavity, the method, comprising:

incubating the plurality of hollow shell particles to grow the one or more cells contained therein, wherein at least some of the plurality of hollow shell particles expand in size in response to growing cell colonies within the respective hollow shell particles; and filtering the hollow shell particles with a physical strainer or filter based on a diameter of the plurality of hollow shell particles.

7. The method of using the particle system of claim 6, comprising exposing the incubated plurality of hollow shell particles to a new solution to exchange the new solution into the void or cavity of the plurality of hollow shell particles.

8. The method of using the particle system of claim 6, comprising exposing the incubated plurality of hollow shell particles to a stain or fluorescent reporter.

9. A method of using a particle system comprising:

providing plurality of hollow shell particles formed from a biocompatible and chemically or physically degradable crosslinked hydrogel, each hollow shell particle having a void or cavity formed therein and surrounded by a shell of crosslinked hydrogel and having a single cell contained in the void or cavity of at least some of the plurality of particles;

incubating the plurality of hollow shell particles in a growth medium for a time period to obtain multicellular colonies contained in the void or cavity of at least some of the plurality of hollow shell particles;

capturing secretions from the multicellular colonies within the hollow shell particles;

labeling the secretions with a fluorescent label or fluorogenic substrate; and passing the plurality of hollow shell particles through a fluorescence activated cell sorter and sorting hollow shell particles containing multicellular colonies and labelled secretions based on a fluorescence and/or scatter signal of each hollow shell particle.

10. The method of claim 9, further comprising loading the sorted hollow shell particles into a plurality of separate sample volumes, wherein each sample volume contains a single hollow shell particle.

11. The method of claim 10, further comprising exposing the sorted hollow shell particles in the separate sample volumes to one or more reagents.

12. The method of claim 11, wherein the one or more reagents comprise a fluorogenic substrate.

13. The method of claim 9, wherein the growth medium is a selective growth medium that enables growth of a target population of cells.

14. The method of claim 9, wherein the plurality of hollow shell particles comprises greater than 10,000 hollow shell particles.

* * * * *

SEQUENCE LISTING

```
<160> NUMBER OF SEQ ID NOS: 11

<210> SEQ ID NO 1
<211> LENGTH: 16
<212> TYPE: PRT
<213> ORGANISM: Artificial Sequence
<220> FEATURE:
<223> OTHER INFORMATION: matrix metalloprotease degradable crosslinker

<400> SEQUENCE: 1

Gly Cys Arg Asp Gly Pro Gln Gly Ile Trp Gly Gln Asp Arg Cys Gly
1               5                   10                  15


<210> SEQ ID NO 2
<211> LENGTH: 11
<212> TYPE: PRT
<213> ORGANISM: Artificial Sequence
<220> FEATURE:
<223> OTHER INFORMATION: crosslinker

<400> SEQUENCE: 2
```

Gly Cys Glu Asn Leu Tyr Phe Gln Gly Cys Gly
1 5 10

<210> SEQ ID NO 3
<211> LENGTH: 7
<212> TYPE: PRT
<213> ORGANISM: Artificial Sequence
<220> FEATURE:
<223> OTHER INFORMATION: peptide linker

<400> SEQUENCE: 3

Gly Asn Asn Gln Gln Asn Tyr
1 5

<210> SEQ ID NO 4
<211> LENGTH: 8
<212> TYPE: PRT
<213> ORGANISM: Artificial Sequence
<220> FEATURE:
<223> OTHER INFORMATION: peptide linker

<400> SEQUENCE: 4

Gly Pro Gln Gly Ile Ala Gly Gln
1 5

<210> SEQ ID NO 5
<211> LENGTH: 8
<212> TYPE: PRT
<213> ORGANISM: Artificial Sequence
<220> FEATURE:
<223> OTHER INFORMATION: peptide linker

<400> SEQUENCE: 5

Ile Pro Val Ser Leu Arg Ser Gly
1 5

<210> SEQ ID NO 6
<211> LENGTH: 7
<212> TYPE: PRT
<213> ORGANISM: Artificial Sequence
<220> FEATURE:
<223> OTHER INFORMATION: peptide linker

<400> SEQUENCE: 6

Gln Pro Gln Gly Leu Ala Lys
1 5

<210> SEQ ID NO 7
<211> LENGTH: 7
<212> TYPE: PRT
<213> ORGANISM: Artificial Sequence
<220> FEATURE:
<223> OTHER INFORMATION: peptide linker

<400> SEQUENCE: 7

Gly Pro Leu Ser Leu Gly Lys
1 5

<210> SEQ ID NO 8
<211> LENGTH: 8
<212> TYPE: PRT
<213> ORGANISM: Artificial Sequence
<220> FEATURE:
<223> OTHER INFORMATION: peptide linker

<400> SEQUENCE: 8

Gly Pro Leu Gly Met His Gly Lys

-continued

```
1               5


<210> SEQ ID NO 9
<211> LENGTH: 9
<212> TYPE: PRT
<213> ORGANISM: Artificial Sequence
<220> FEATURE:
<223> OTHER INFORMATION: peptide linker

<400> SEQUENCE: 9

Asp Gly Pro Gln Gly Ile Trp Gly Gln
1               5


<210> SEQ ID NO 10
<211> LENGTH: 7
<212> TYPE: PRT
<213> ORGANISM: Artificial Sequence
<220> FEATURE:
<223> OTHER INFORMATION: peptide linker

<400> SEQUENCE: 10

Glu Asn Leu Tyr Phe Gln Gly
1               5


<210> SEQ ID NO 11
<211> LENGTH: 7
<212> TYPE: PRT
<213> ORGANISM: Artificial Sequence
<220> FEATURE:
<223> OTHER INFORMATION: peptide linker

<400> SEQUENCE: 11

Glu Asn Leu Tyr Phe Gln Ser
1               5
```